US010542751B2

(12) United States Patent
Li et al.

(10) Patent No.: US 10,542,751 B2
(45) Date of Patent: *Jan. 28, 2020

(54) GENERATION OF PEROXYFORMIC ACID THROUGH POLYHYDRIC ALCOHOL FORMATE

(71) Applicant: ECOLAB USA INC, Saint Paul, MN (US)

(72) Inventors: Junzhong Li, Saint Paul, MN (US); Allison Brewster, Saint Paul, MN (US); Richard Staub, Saint Paul, MN (US); Steven J. Lange, Saint Paul, MN (US); Taz Cheritu, Saint Paul, MN (US); Jonathan P. Fast, Saint Paul, MN (US); Catherine Hanson, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/967,077

(22) Filed: Apr. 30, 2018

(65) Prior Publication Data
US 2018/0242578 A1 Aug. 30, 2018

Related U.S. Application Data

(63) Continuation of application No. 15/433,218, filed on Feb. 15, 2017, which is a continuation of application No. 15/345,263, filed on Nov. 7, 2016, now Pat. No. 10,433,547, which is a continuation of application No. 14/973,389, filed on Dec. 17, 2015, now Pat. No. 9,518,013.

(60) Provisional application No. 62/094,048, filed on Dec. 18, 2014.

(51) Int. Cl.
A01N 37/16 (2006.01)
C07C 407/00 (2006.01)
C11D 3/00 (2006.01)
C12P 7/40 (2006.01)
C11D 3/39 (2006.01)
C11D 3/48 (2006.01)
C07C 409/24 (2006.01)
A01N 37/00 (2006.01)
A61L 2/00 (2006.01)
A61L 2/16 (2006.01)
A61K 8/38 (2006.01)
A61Q 17/00 (2006.01)

(52) U.S. Cl.
CPC ............ A01N 37/16 (2013.01); A01N 37/00 (2013.01); A61K 8/38 (2013.01); A61L 2/00 (2013.01); A61L 2/16 (2013.01); A61Q 17/005 (2013.01); C07C 407/00 (2013.01); C07C 409/24 (2013.01); C11D 3/00 (2013.01); C11D 3/3947 (2013.01); C11D 3/48 (2013.01); C12P 7/40 (2013.01)

(58) Field of Classification Search
CPC .... A01N 37/16; C07C 407/00; A61Q 17/005; A61K 8/38
See application file for complete search history.

(56) References Cited

U.S. PATENT DOCUMENTS

| 2,448,252 | A | 8/1948 | Cornthwaite |
| 2,955,905 | A | 10/1960 | Davies et al. |
| 2,995,524 | A | 8/1961 | Wylie et al. |
| 3,169,986 | A | 2/1965 | Webb |
| 3,256,198 | A | 6/1966 | Matzner et al. |
| 3,272,750 | A | 9/1966 | Chase et al. |
| 3,432,546 | A | 3/1969 | Oringer et al. |
| 3,847,830 | A | 11/1974 | Williams et al. |
| 3,925,234 | A | 12/1975 | Hachmann et al. |
| 4,003,841 | A | 1/1977 | Hachmann et al. |
| 4,051,058 | A | 9/1977 | Bowing et al. |
| 4,126,573 | A | 11/1978 | Johnston |
| 4,170,453 | A | 10/1979 | Kitko |
| 4,233,235 | A | 11/1980 | Camden et al. |
| 4,370,251 | A | 1/1983 | Liao et al. |
| 4,412,934 | A | 11/1983 | Chung et al. |
| 4,483,778 | A | 11/1984 | Thompson et al. |
| 4,486,327 | A | 12/1984 | Murphy et al. |
| 4,617,090 | A | 10/1986 | Chum et al. |

(Continued)

FOREIGN PATENT DOCUMENTS

| CA | 2266523 A1 | 9/1999 |
| CA | 2475361 A1 | 8/2003 |

(Continued)

OTHER PUBLICATIONS

Carboni-Oerlemans, et al., "Hyrolase-Catalysed Synthesis of Peroxycarboxylic Acids: Biocatalytic Promiscuity for Practical Applications", ScienceDirect, Journal of Biotechnology 126, pp. 140-151. Apr. 7, 2006.

(Continued)

Primary Examiner — Robert S Cabral
(74) Attorney, Agent, or Firm — McKee, Voorhess & Sease, PLC

(57) ABSTRACT

The present invention relates generally to peroxyformic acid forming compositions, methods for forming peroxyformic acid, preferably in situ, using the peroxyformic acid forming compositions. The present invention also relates to the peroxyformic acid formed by the above compositions and methods. The present invention further relates to the uses of the peroxyformic acid, preferably in situ, for treating a surface or a target. The present invention further relates to methods for treating a biofilm using peroxyformic acid, including peroxyformic acid generated in situ.

20 Claims, 28 Drawing Sheets

(56) References Cited

U.S. PATENT DOCUMENTS

| | | |
|---|---|---|
| 4,655,781 A | 4/1987 | Hsieh et al. |
| 4,778,618 A | 10/1988 | Fong et al. |
| 4,964,870 A | 10/1990 | Fong et al. |
| 5,030,240 A | 7/1991 | Wiersema et al. |
| 5,143,641 A | 9/1992 | Nunn |
| 5,200,189 A | 4/1993 | Oakes et al. |
| 5,246,620 A | 9/1993 | Gethoffer et al. |
| 5,266,587 A | 11/1993 | Sankey et al. |
| 5,314,687 A | 5/1994 | Oakes et al. |
| 5,391,324 A | 2/1995 | Reinhardt et al. |
| 5,422,028 A | 6/1995 | Oakes et al. |
| 5,431,849 A | 7/1995 | Damhus et al. |
| 5,463,112 A | 10/1995 | Sankey et al. |
| 5,466,825 A | 11/1995 | Carr et al. |
| 5,503,765 A | 4/1996 | Schepers et al. |
| 5,505,740 A | 4/1996 | Kong et al. |
| 5,576,282 A | 11/1996 | Miracle et al. |
| 5,589,507 A | 12/1996 | Hall, II et al. |
| 5,616,281 A | 4/1997 | Hardy et al. |
| 5,616,335 A | 4/1997 | Nicolle et al. |
| 5,635,195 A | 6/1997 | Hall, II et al. |
| 5,637,755 A | 6/1997 | Nagumo et al. |
| 5,681,805 A | 10/1997 | Scheuing et al. |
| 5,716,923 A | 2/1998 | MacBeath et al. |
| 5,718,910 A | 2/1998 | Oakes et al. |
| 5,817,614 A | 10/1998 | Miracle et al. |
| 5,827,447 A | 10/1998 | Tamura et al. |
| 5,827,808 A | 10/1998 | Appleby et al. |
| 5,840,343 A | 11/1998 | Hall, II et al. |
| 5,914,303 A | 6/1999 | Sankey et al. |
| 5,928,382 A | 7/1999 | Reinhardt et al. |
| 5,977,403 A | 11/1999 | Byers |
| 5,998,350 A | 12/1999 | Burns et al. |
| 6,022,381 A | 2/2000 | Dias et al. |
| 6,068,815 A | 5/2000 | Oberleitner et al. |
| 6,156,156 A | 12/2000 | Rousu et al. |
| 6,177,393 B1 | 1/2001 | McGregor et al. |
| 6,207,632 B1 | 3/2001 | Brooker et al. |
| 6,211,237 B1 | 4/2001 | Huss et al. |
| 6,221,341 B1 | 4/2001 | Montgomery |
| 6,262,013 B1 | 7/2001 | Smith et al. |
| 6,274,542 B1 | 8/2001 | Carr et al. |
| 6,284,719 B1 | 9/2001 | Simms |
| 6,284,793 B1 | 9/2001 | Fuchs et al. |
| 6,399,564 B1 | 6/2002 | Speed et al. |
| 6,537,958 B1 | 3/2003 | Di Capua et al. |
| 6,548,467 B2 | 4/2003 | Baker et al. |
| 6,548,470 B1 | 4/2003 | de Buzzaccarini et al. |
| 6,569,286 B1 | 5/2003 | Withenshaw et al. |
| 6,585,934 B1 | 7/2003 | Oberleitner et al. |
| 6,599,871 B2 | 7/2003 | Smith |
| 6,602,845 B2 | 8/2003 | Connor et al. |
| 6,649,140 B2 | 11/2003 | Paparatto et al. |
| 6,689,732 B1 | 2/2004 | Guedira et al. |
| 6,693,069 B2 | 2/2004 | Korber et al. |
| 6,841,090 B1 | 1/2005 | Serego Allighieri et al. |
| 7,012,154 B2 | 3/2006 | Vineyard et al. |
| 7,061,597 B2 | 6/2006 | Oberleitner et al. |
| 7,189,385 B2 | 3/2007 | Montgomery |
| 7,217,295 B2 | 5/2007 | Samain et al. |
| 7,494,963 B2 | 2/2009 | Ahmed et al. |
| 7,550,420 B2 | 6/2009 | DiCosimo et al. |
| 7,569,232 B2 | 8/2009 | Man et al. |
| 7,598,218 B2 | 10/2009 | Stolte et al. |
| 7,612,030 B2 | 11/2009 | DiCosimo et al. |
| 7,682,403 B2 | 3/2010 | Gohl et al. |
| 7,723,083 B2 | 5/2010 | DiCosimo et al. |
| 7,754,460 B2 | 7/2010 | Amin et al. |
| 7,807,425 B2 | 10/2010 | DiCosimo et al. |
| 7,829,315 B2 | 11/2010 | DiCosimo et al. |
| 7,915,445 B2 | 3/2011 | Maatta et al. |
| 7,919,122 B2 | 4/2011 | Okano et al. |
| 7,951,566 B2 | 5/2011 | DiCosimo et al. |
| 7,964,378 B2 | 6/2011 | DiCosimo et al. |
| 8,110,603 B2 | 2/2012 | Kawabata et al. |
| 8,129,153 B2 | 3/2012 | DiCosimo et al. |
| 8,168,676 B2 | 5/2012 | DiCosimo et al. |
| 8,178,581 B2 | 5/2012 | DiCosimo et al. |
| 8,293,792 B2 | 10/2012 | DiCosimo et al. |
| 8,367,728 B2 | 2/2013 | DiCosimo et al. |
| 8,389,575 B2 | 3/2013 | DiCosimo et al. |
| 8,426,634 B2 | 4/2013 | Neas et al. |
| 8,486,679 B2 | 7/2013 | DiCosimo et al. |
| 8,518,675 B2 | 8/2013 | DiCosimo et al. |
| 8,729,296 B2 | 5/2014 | Fast et al. |
| 8,802,061 B2 | 8/2014 | Tichy et al. |
| 8,841,098 B2 | 9/2014 | Payne et al. |
| 8,865,436 B2 | 10/2014 | Payne et al. |
| 8,877,354 B2 | 11/2014 | Horiuchi et al. |
| 8,883,485 B2 | 11/2014 | Barnett et al. |
| 9,012,504 B2 | 4/2015 | Olson et al. |
| 9,034,390 B2 | 5/2015 | Kielbania, Jr. |
| 9,044,403 B2 | 6/2015 | Schultz |
| 9,192,909 B2 | 11/2015 | Kraus et al. |
| 9,282,746 B2 | 3/2016 | Amin et al. |
| 9,288,992 B2 | 3/2016 | Li et al. |
| 9,321,664 B2 | 4/2016 | Li et al. |
| 9,518,013 B2 | 12/2016 | Li |
| 9,585,397 B2 | 3/2017 | Li et al. |
| 9,676,711 B2 | 6/2017 | Junzhong et al. |
| 9,701,931 B2 | 7/2017 | Moore |
| 9,752,105 B2 | 9/2017 | Stokes et al. |
| 2002/0161258 A1 | 10/2002 | Miracle et al. |
| 2003/0100469 A1 | 5/2003 | Connor et al. |
| 2004/0035537 A1 | 2/2004 | Delmas et al. |
| 2004/0097410 A1 | 5/2004 | Zheng et al. |
| 2005/0008526 A1 | 1/2005 | Bianchetti et al. |
| 2005/0109981 A1 | 5/2005 | Tucker et al. |
| 2006/0177518 A1 | 8/2006 | Stevenson et al. |
| 2007/0082832 A1 | 4/2007 | DiCosimo et al. |
| 2007/0093407 A1 | 4/2007 | Bianchetti et al. |
| 2007/0100204 A1 | 5/2007 | Feld et al. |
| 2007/0184999 A1 | 8/2007 | DiCosimo et al. |
| 2007/0249712 A1 | 10/2007 | Dee et al. |
| 2007/0274857 A1 | 11/2007 | Okano et al. |
| 2008/0029130 A1 | 2/2008 | Concar et al. |
| 2008/0088873 A1 | 7/2008 | Chihara |
| 2008/0176299 A1 | 7/2008 | DiCosimo et al. |
| 2008/0176784 A1 | 7/2008 | Clowes et al. |
| 2008/0275132 A1 | 11/2008 | McSherry |
| 2009/0018049 A1 | 1/2009 | Stolte et al. |
| 2009/0221704 A1 | 9/2009 | Aksela |
| 2010/0048448 A1 | 2/2010 | DiCosimo et al. |
| 2010/0084603 A1 | 4/2010 | Narayan et al. |
| 2010/0159028 A1 | 6/2010 | Shultz |
| 2010/0189707 A1 | 7/2010 | Barnett |
| 2010/0286017 A1 | 11/2010 | Righetto |
| 2011/0081693 A1 | 4/2011 | DiCosimo et al. |
| 2011/0136907 A1 | 6/2011 | DiCosimo et al. |
| 2011/0136908 A1 | 6/2011 | DiCosimo et al. |
| 2011/0152368 A1 | 6/2011 | DiCosimo et al. |
| 2011/0152369 A1 | 6/2011 | DiCosimo et al. |
| 2011/0152370 A1 | 6/2011 | DiCosimo et al. |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. et al. |
| 2011/0177148 A1 | 7/2011 | DiCosimo et al. |
| 2011/0236335 A1 | 9/2011 | DiCosimo et al. |
| 2011/0236336 A1 | 9/2011 | DiCosimo et al. |
| 2011/0236337 A1 | 9/2011 | DiCosimo et al. |
| 2011/0236338 A1 | 9/2011 | DiCosimo et al. |
| 2011/0236339 A1 | 9/2011 | DiCosimo et al. |
| 2011/0300201 A1 | 12/2011 | Becker et al. |
| 2012/0021486 A1 | 1/2012 | Dinu et al. |
| 2012/0036649 A1 | 2/2012 | Auterinen et al. |
| 2012/0136588 A1 | 5/2012 | Kubach |
| 2012/0156155 A1 | 6/2012 | DiCosimo et al. |
| 2012/0156156 A1 | 6/2012 | DiCosimo et al. |
| 2012/0156157 A1 | 6/2012 | DiCosimo et al. |
| 2012/0156158 A1 | 6/2012 | DiCosimo et al. |
| 2012/0156159 A1 | 6/2012 | DiCosimo et al. |
| 2012/0164236 A1 | 6/2012 | Iwasa et al. |

(56) References Cited

U.S. PATENT DOCUMENTS

| | | |
|---|---|---|
| 2012/0172441 A1 | 7/2012 | Li et al. |
| 2013/0111674 A1 | 5/2013 | Yoon |
| 2013/0158117 A1 | 6/2013 | DiCosimo et al. |
| 2013/0171217 A1 | 7/2013 | Chisholm et al. |
| 2013/0203849 A1 | 8/2013 | Ben Yehuda |
| 2013/0247308 A1 | 9/2013 | Duerrschmidt et al. |
| 2013/0261182 A1 | 10/2013 | Payne et al. |
| 2013/0289113 A1 | 10/2013 | Payne |
| 2013/0289114 A1 | 10/2013 | Payne et al. |
| 2013/0289115 A1 | 10/2013 | Payne et al. |
| 2013/0303844 A1 | 11/2013 | Grudo et al. |
| 2014/0113966 A1 | 4/2014 | DiCosimo et al. |
| 2014/0120179 A1 | 5/2014 | Smith et al. |
| 2014/0121272 A1 | 5/2014 | Smith et al. |
| 2014/0314829 A1 | 10/2014 | Boyd et al. |
| 2014/0338688 A1 | 11/2014 | Boyd et al. |
| 2015/0018319 A1 | 1/2015 | Larson et al. |
| 2015/0118167 A1 | 4/2015 | Boyd et al. |
| 2015/0265511 A1 | 9/2015 | Boyd et al. |
| 2016/0205946 A1 | 7/2016 | Stauffer et al. |
| 2017/0020130 A1 | 1/2017 | Buschmann et al. |
| 2017/0064949 A1 | 3/2017 | Kraus et al. |
| 2017/0081617 A1 | 3/2017 | Allesen-Holm |
| 2017/0118989 A1 | 5/2017 | Oppong et al. |
| 2017/0156321 A1 | 6/2017 | Li |

FOREIGN PATENT DOCUMENTS

| | | |
|---|---|---|
| DE | 201510209819 A1 | 12/2016 |
| EP | 0125781 A1 | 11/1984 |
| EP | 0231632 A2 | 8/1987 |
| EP | 0233731 A1 | 8/1987 |
| EP | 0267047 A2 | 5/1988 |
| EP | 0863098 B1 | 2/1998 |
| EP | 1022946 B1 | 9/1998 |
| EP | 0751933 B1 | 6/1999 |
| EP | 1131016 B1 | 6/1999 |
| EP | 1125497 B1 | 6/2003 |
| EP | 1618786 A1 | 4/2004 |
| EP | 1114137 B1 | 7/2004 |
| EP | 1129171 B1 | 8/2005 |
| EP | 2064385 B1 | 9/2007 |
| EP | 1926808 B1 | 7/2011 |
| EP | 2470666 B1 | 7/2014 |
| EP | 2471941 B1 | 9/2015 |
| EP | 2714877 B1 | 7/2017 |
| EP | 2566943 B1 | 9/2017 |
| JP | 62155203 | 7/1987 |
| JP | 6305920 | 11/1994 |
| JP | 5186989 B2 | 4/2013 |
| WO | 9115474 A1 | 10/1991 |
| WO | 9403395 A1 | 2/1994 |
| WO | 9424869 | 11/1994 |
| WO | 9504128 A1 | 2/1995 |
| WO | 9524388 A1 | 9/1995 |
| WO | 9532625 A1 | 12/1995 |
| WO | 9533816 A1 | 12/1995 |
| WO | 9614384 A1 | 5/1996 |
| WO | 9616148 A1 | 5/1996 |
| WO | 9719594 A1 | 6/1997 |
| WO | 9803513 A1 | 1/1998 |
| WO | 9804659 A3 | 2/1998 |
| WO | 1999031215 A1 | 6/1999 |
| WO | 0018228 A1 | 4/2000 |
| WO | 0018521 A1 | 4/2000 |
| WO | 0045639 A1 | 8/2000 |
| WO | 2007031596 A2 | 3/2007 |
| WO | 2010050634 A1 | 5/2010 |
| WO | 2011089313 A2 | 7/2011 |
| WO | 2011090980 A1 | 7/2011 |
| WO | 2012037294 A2 | 3/2012 |
| WO | 2012084426 A1 | 6/2012 |
| WO | 2015118357 A2 | 8/2015 |
| WO | 2015181287 A1 | 12/2015 |
| WO | 2016100694 A1 | 6/2016 |
| WO | 2016100700 A1 | 6/2016 |
| WO | 2016135351 A1 | 9/2016 |
| WO | 2017007416 A1 | 1/2017 |
| WO | 2017044806 A1 | 3/2017 |

OTHER PUBLICATIONS

Dannacher, Josef J., "Catalytic Bleach: Most Valuable Applications for Smart Oxidation Chemistry", Journal of Molecular Catalysis A: Chemical 251, pp. 159-176. Mar. 20, 2006.

Effkemann, et al., "Peroxide Analysis in Laundry Detergents Using Liquid Chromatography", Analytica Chimica Acta 363, pp. 97-103. Jan. 2, 1998.

Leveneur, et al., "Synthesis of Peroxypropionic Acid From Propionic Acid and Hydrogen Peroxide over Hetrogeneous Catalysts", Chemical Engineering Journal 147, pp. 323-329. Dec. 31, 2009.

Maeda, et al., "Assessment of Acyl Groups and Reaction Conditions in the Competition between Perhydrolysis and Hydrolysis of Acyl Resorufins for Developing an Indicator REaction for Fluorometric Analysis of Hydrogen Peroxide". Feb. 28, 2002.

Muurinen, et al., "Organosolv Pulping: A review and distillation study related to peroxyacid pulping", Department of Process Engineering, University of Oulu, 75 pages. May 16, 2000.

Ogata, et al., "The Formation of Peracids by the Perhydrolysis with Alkaline Hydrogen Peroxide", Tetrochem, vol. 23, pp. 3327-3332. Dec. 31, 1967.

Rusch, et al., "Biocatalytic Peroxy Acid Formation for Disinfection", Journal of Molecular Catalysis B: Enzymatic 19-20, pp. 499-505. May 16, 2002.

Rusch, et al., "Lipase-Catalyzed Conversions of Trimethylsilyl Ethers: Deprotection, Acetylation, Epoxidation and One-Pot-Multi-Step Reactions", Journal of Molecular Catalysis B: Enzymatic 7, pp. 283-289. Feb. 26, 1999.

Rusch, et al., "Lipase-Catalyzed Preparation of Peroxy Acids and their use for Epoxidation", Journal of Molecular Catalysis A: Chemical 117, pp. 311-319. Dec. 31, 1997.

Tsunokawa et al., "A Versatile Method for Preparation of O-Alkylperoxycarbonic Acids: Epoxidation with Alkyloxycarbonylimidazoles and Hydrogen Peroxide", Tetrahedron Letters, vol. 23, No. 20, pp. 2113-2116. Dec. 31, 1982.

Yin, et al., "Switching Catalysis From Hydrolysis to Perhydrolysis in Pseudomonas Fluorescnes Esterase", Biochemistry, 49, pp. 1931-1942. Dec. 31, 2010.

Ecolab USA, Inc., PCT/IB2011/055830 filed Dec. 20, 2011, "The International Search Report and the Written Opinion of the International Searching Authority, of the Declaration". dated Aug. 24, 2012.

Ecolab USA Inc., PCT/IB2011/055832 filed Dec. 20, 2011, "The International Search Report and the Written Opinion of the International Searching Authority, or the Declaration". dated Aug. 14, 2012.

International Searching Authority, "Written Opinion of the International Searching Authority", Issued in connection to International Application No. PCT/US2015/066427, 8 pages. dated Apr. 19, 2016.

Klenk, "Peroxy Compounds, Organic", Ullmann's Encyclopedia of Industrial Chemistry, 2012, pp. 325-360.

Kesla Ag, "Upersan Dip", Product Information, 2 pages. 2016.

Israel Patent Office, "Written Opinion of the International Searching Authority", issued in connection to International Application No. PCT/US2015/066427, filed Dec. 17, 2015, dated Apr. 19, 2016, 8 pages.

Tao, Weiyi et al., "Efficient Production of Peracetic Acid in Aqueous Solution with Cephalosporin-Deacetylating Acetyl Xylan Esterase from Bacillus Subtilis", Process Biochemistry 50 (2015) pp. 2121-2127 available online.

Yin (Tyler) DeLu et al., "New Structural Motif for Carboxylic Acid Perhydrolases", National Institute of Health, pp. 3037-3046, manuscript available Feb. 25, 2014.

Jakob, "Peroxo Compounds, Inorganic", Ullmann's Encyclopedia of Industrial Chemistry, 2007, pp. 293-324.

(56) References Cited

OTHER PUBLICATIONS

Ullman's, "Peroxy Compounds, Organic", Ullmannn's Encyclopedia of Industrial Chemistry, 2018, pp. 325-354.
Hilal, S.H., "Estimation of Hydrolysis Rate Constants of Carboxylic Acid Ester and Phosphate Ester Compounds in Aqueous Systems from Molecular Structure by SPARC", EPA Research and Development, 113 pages, Sep. 2006.
Safety Data Sheet, "Glyceryl triacetate", Santa Cruz Biotechnology, Inc., 6 pages, Nov. 6, 2018.
Safety Data Sheet, "Glycerol Triformate, Technical Grade" Santa Cruz Biotechnology, Inc., 5 pages, Jul. 24, 2017.
Humphreys et al., "Rate Measurements on Fast Reactions in the Stirred Flow Reactor; the Alkaline Hydrolysis of Methyl and Ethyl Formate", Contribution from the Department of Chemistry, Columbia University, 4 pages, Aug. 29, 1955.

GENERATION OF PEROXYFORMIC ACID THROUGH POLYHYDRIC ALCOHOL FORMATE

CROSS-REFERENCE TO RELATED APPLICATIONS

This application is a Continuation application of U.S. Ser. No. 15/433,218, filed Feb. 15, 2017, which is a Continuation application of U.S. Ser. No. 15/345,263 filed Nov. 7, 2016, which is a Continuation application of U.S. Ser. No. 14/973,389 filed Dec. 17, 2015, now U.S. Pat. No. 9,518,013 issued Dec. 13, 2016, which claims priority under 35 U.S.C. § 119 to provisional application U.S. Ser. No. 62/094,048 filed Dec. 18, 2014, herein incorporated by reference in its entirety. The entire contents of these patent applications are hereby expressly incorporated herein by reference including, without limitation, the specification, claims, and abstract, as well as any figures, tables, or drawings thereof.

FIELD OF THE INVENTION

The present invention relates generally to peroxyformic acid forming compositions, methods for forming peroxyformic acid, preferably in situ, using the peroxyformic acid forming compositions. The present invention also relates to peroxyformic acid formed by the above compositions and methods. The present invention further relates to the uses of peroxyformic acid, preferably in situ, for treating a surface or a target. The present invention further relates to methods for treating a biofilm using peroxyformic acid, including peroxyformic acid generated in situ.

BACKGROUND OF THE INVENTION

Among various biocides known, peroxycarboxylic acids are increasingly used as antimicrobials and bleaching agents in many applications, owing to their high efficacy against a broad spectrum of microorganisms, color safe property, low residues and nontoxic nature of their decomposition products. Peracetic acid is the most commonly used peroxycarboxylic acid and has been shown to be a good biocide, but only at relatively high concentrations (generally greater than 80 part per million). Similarly, peroxyfatty acids have also been shown to be biocidal, but only at high concentrations (greater than 200 ppm), such as in the composition disclosed in European Patent Application No. 233,731. In contrast, peroxyformic acid has an advantageous degree and range of microcidal properties compared to other peroxycarboxylic acids, such as peracetic and perproprionic acids, as disclosed by V. Merka et al in J. Hyg. Epidem. Microbiol. Immunol, 1965 (IX) 220, as well as in European Patent Application No. 863,098,96.

Peroxycarboxylic acid compositions are generally made through an acid catalyzed equilibrium reaction. Most often, the peroxycarboxylic acids are generated in a chemical plant, and then shipped to customers for on-site use. Due to the limited storage stability of peroxycarboxylic acids, the peroxycarboxylic acids must be packed in special containers and shipped under strict Department of Transportation (DOT) guidelines. Further, excess amounts of reagents (e.g., acids, oxidizing agents, and stabilizers) are present in the compositions during shipping to prevent decomposition. For peroxyformic acid, however, the inherent instability of the substance relative to the higher alkyl peracid, and the explosive nature of the substance at the concentrate make it an even more significant challenge to be manufactured, stored and transported before dilution prior to use, in the similar way like higher alkyl peracid. Thus, there are needs for the on-site generation of peroxycarboxylic acids, especially peroxyformic acid.

It is known in the art that peroxycarboxylic acids could be alternatively generated in situ through the perhydrolysis of the higher alkyl carboxylic acid esters of polyhydric alcohol, as disclosed in the Patent Application No. WO2012/090124 and U.S. Pat. No. 7,919,122. The perhydrolysis reaction, however, has to be carried out under strong alkaline conditions, for example at pH greater than 12, or at least keeping the pH of the solution between 10 to 12 during the perhydrolysis reaction. As a result, the solution has to be acidified after the perhydrolysis reaction in order to bring the generated peroxycarboxylic acid in the form to be efficient as biocide. One approach to increase the perhydrolysis reactivity of the esters is using perhydrolysis enzyme, such as disclosed in U.S. Pat. No. 8,865,436. With the help of the enzyme, the reaction could be carried out in close to neutral pH conditions, and thus avoid the acid neutralization process. However, the enzyme itself is expensive, and including the enzyme in the system will also increase the delivery complexity.

There is a need to seek alternative ways to generate peroxycarboxylic acids, namely peroxyformic acids. The present disclosure addresses this and the related needs using, inter alia, performic acid.

BRIEF SUMMARY OF THE INVENTION

The present invention relates generally to peroxyformic acid forming compositions, methods for forming peroxyformic acid, preferably in situ, using the peroxyformic acid forming compositions, the peroxyformic acid formed by the above compositions and methods, and the uses of the peroxyformic acid, preferably in situ, for treating a surface or a target. The present invention further relates to methods for treating a biofilm using peroxyformic acid, including peroxyformic acid generated in situ.

In one aspect, the present invention is directed to a peroxyformic acid forming composition comprising: a) a first reagent that comprises an ester of a polyhydric alcohol and formic acid, and b) a second reagent that comprises hydrogen peroxide or that comprises a substance that generates hydrogen peroxide when in contact with a liquid, wherein 1) said first reagent and said second reagent are kept separately prior to use, and when it is time to generate peroxyformic acid, said first reagent and said second reagent are configured to be contacted with each other to form a liquid that comprises peroxyformic acid and has a pH below about 11, and pH of the formed liquid becomes about 8 or lower within about 1 minute after the contact between said first reagent and said second reagent; or 2) said second reagent comprises a substance that generates hydrogen peroxide when in contact with a liquid, said first reagent and said second reagent are comprised in a solid composition, and when it is time to generate peroxyformic acid, said solid composition is configured to be contacted with a liquid to form a liquid that comprises peroxyformic acid and has a pH below about 11, and pH of the formed liquid becomes about 8 or lower within about 1 minute after the contact between said solid composition and said liquid.

In another aspect, the present invention is directed to a method for forming peroxyformic acid comprising: a) contacting a first reagent that comprises an ester of a polyhydric alcohol and formic acid, and a second reagent that comprises hydrogen peroxide or that comprises a substance that generates hydrogen peroxide when in contact with a liquid to form a liquid that comprises peroxyformic acid and has a pH below about 11, wherein said first reagent and said second reagent are kept separately prior to said contacting and pH of said formed liquid becomes about 8 or lower within about 1 minute after the contact between said first reagent and said second reagent; or b) contacting a solid composition that comprises a first reagent that comprises an ester of a polyhydric alcohol and formic acid, and a second reagent that comprises a substance that generates hydrogen peroxide when in contact with a liquid with a liquid to form a liquid that comprises peroxyformic acid and has a pH below about 11, and pH of said formed liquid becomes about 8 or lower within about 1 minute after the contact between said solid composition and said liquid.

In some embodiments, the use of the above peroxyformic acid forming compositions and the above methods for forming peroxyformic acid are at least based on the surprising finding that the formic acid esters of polyhydric alcohol, such as glycerol formates, can quickly or instantly generate peroxyformic acid in the presence of $H_2O_2$ under very mild pH conditions in the absence of an enzyme. Furthermore, the pH of the solution quickly or instantly moved significantly lower after the mixing of the esters and $H_2O_2$ solution, thus eliminating the need for adjusting pH of the formed liquid.

In another aspect, the present invention is directed to peroxyformic acid formed using the above method.

In still another aspect, the present invention is directed to a method for treating a surface or a target, which method comprises a step of contacting a surface or a target with an effective amount of peroxyformic acid formed using the above methods, preferably in situ, to form a treated target composition, wherein said treated target composition comprises from about 0.1 ppm to about 10,000 ppm of said peroxyformic acid, and said contacting step lasts for sufficient time to stabilize or reduce microbial population in and/or on said surface or target or said treated target composition.

In yet another aspect, the present invention is directed to a method for treating a biofilm, which method comprises contacting a biofilm on a surface with an effective amount of peroxyformic acid for a sufficient time to stabilize, reduce and/or remove microbial population in and/or on said treated biofilm, or to stabilize, reduce and/or remove said biofilm on said surface.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
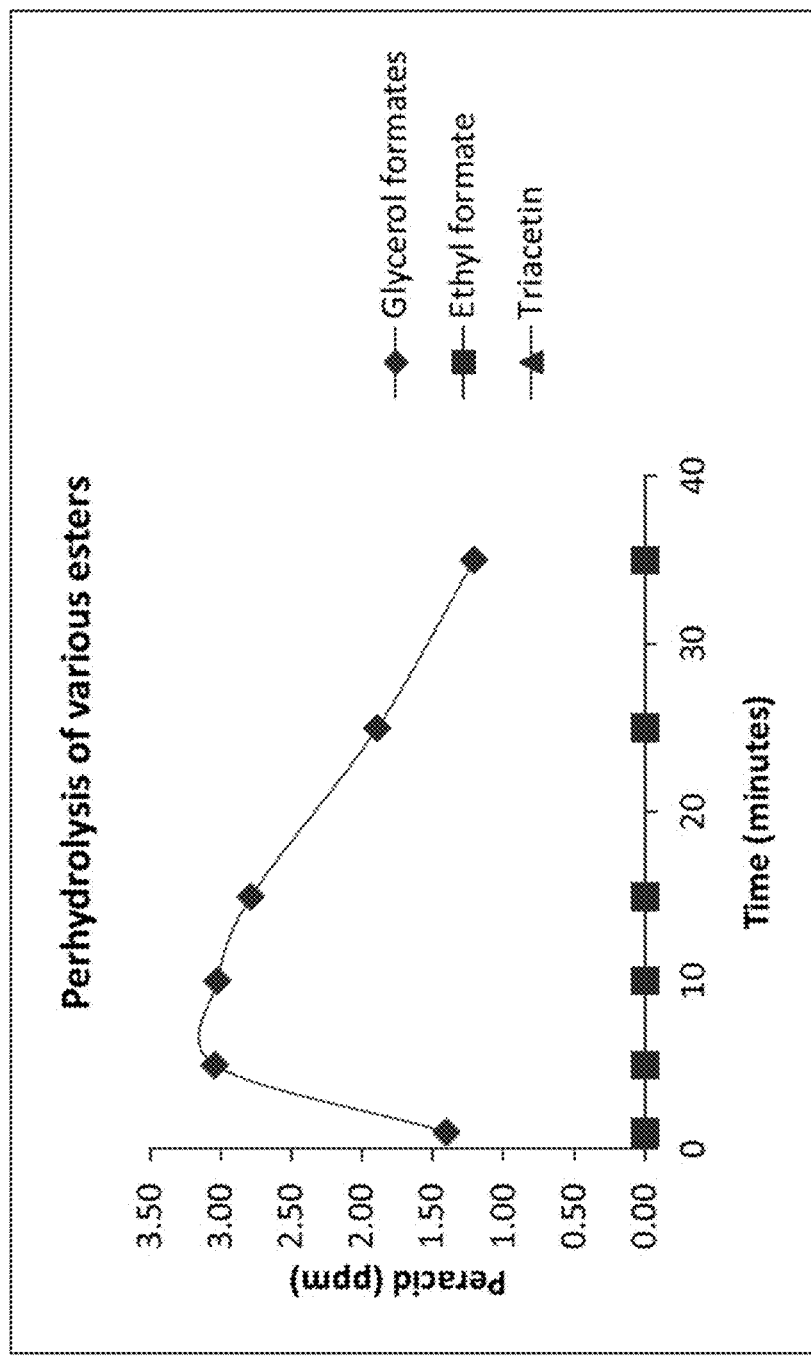
FIG. 1 illustrates perhydrolysis of various esters according to embodiments of the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The embodiments of this invention are not limited to particular peroxyformic acid forming compositions, methods for forming peroxyformic acid, the formed peroxyformic acid and methods for using the same, which can vary and are understood by skilled artisans. It is further to be understood that all terminology used herein is for the purpose of describing particular embodiments only, and is not intended to be limiting in any manner or scope. For example, all units, prefixes, and symbols may be denoted in its SI accepted form. Numeric ranges recited within the specification are inclusive of the numbers defining the range and include each integer within the defined range.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference. So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, "consisting essentially of" means that the methods and compositions may include additional steps, components, ingredients or the like, but only if the additional steps, components and/or ingredients do not materially alter the basic and novel characteristics of the claimed methods and compositions.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food or beverage processing, preparation, or storage activity. Food processing surface is intended to encompass all surfaces used in brewing (including beer brewing and preparation of liquors and spirits) and winemaking processes (e.g., bright beer tanks and lines, fermentation vessels, mash tuns, bottling equipment, pipes, and storage vessels). Examples of food processing surfaces include surfaces of food processing or preparation equipment (e.g., boiling, fermenting, slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food antispoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the term "free," "no," "substantially no" or "substantially free" refers to a composition, mixture, or ingredient that does not contain a particular compound or to which a particular compound or a particular compound-containing compound has not been added. In some embodiments, the reduction and/or elimination of hydrogen peroxide according to embodiments provide hydrogen peroxide-free or substantially-free compositions. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention. As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, the term "laundry" refers to items or articles that are cleaned in a laundry washing machine. In general, laundry refers to any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated. Exemplary treated fibers include those treated for flame retardancy. It should be understood that the term "linen" is often used to describe certain types of laundry items including bed sheets, pillow cases, towels, table linen, table cloth, bar mops and uniforms.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, the term "water" for treatment according to the invention includes a variety of sources, such as freshwater, pond water, sea water, salt water or brine source, brackish water, recycled water, or the like. Waters are also understood to optionally include both fresh and recycled water sources (e.g. "produced waters"), as well as any combination of waters for treatment according to the invention. In some embodiments, produced water (or reuse water) refers to a mixture of water that comprises both water recycled from previous or concurrent oil- and gas-field operations, e.g., fracking, and water that has not been used in oil- and gas-field operations, e.g., fresh water, pond water, sea water, etc.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%/o," and the like are intended to be synonymous with "weight percent," "wt-%," etc.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

Peroxyformic Acid Forming Compositions

The present invention relates to peroxyformic acid forming compositions and uses thereof. In one aspect, the present invention is directed to a peroxyformic acid forming composition comprising: a) a first reagent that comprises an ester of a polyhydric alcohol and formic acid, and b) a second reagent that comprises hydrogen peroxide or that comprises a substance that generates hydrogen peroxide when in contact with a liquid, wherein 1) said first reagent and said second reagent are kept separately prior to use, and when it is time to generate peroxyformic acid, said first reagent and said second reagent are configured to be contacted with each other to form a liquid that comprises peroxyformic acid and has a pH below about 11, and pH of the formed liquid becomes about 8 or lower within about 1 minute after the contact between said first reagent and said second reagent; or 2) said second reagent comprises a substance that generates hydrogen peroxide when in contact with a liquid, said first reagent and said second reagent are comprised in a solid composition, and when it is time to generate peroxyformic acid, said solid composition is configured to be contacted with a liquid to form a liquid that comprises peroxyformic acid and has a pH below about 11, and pH of the formed liquid becomes about 8 or lower within about 1 minute after the contact between said solid composition and said liquid.

In some embodiments, the present peroxyformic acid forming composition comprises a) a first reagent that comprises an ester of a polyhydric alcohol and formic acid, and b) a second reagent that comprises hydrogen peroxide or that comprises a substance that generates hydrogen peroxide when in contact with a liquid, wherein said first reagent and said second reagent are kept separately prior to use, and when it is time to generate peroxyformic acid, said first reagent and said second reagent are configured to be contacted with each other to form a liquid that comprises peroxyformic acid and has a pH below about 11, and pH of the formed liquid becomes about 8 or lower within about 1 minute after the contact between said first reagent and said second reagent. In other embodiments, the present peroxyformic acid forming composition comprises a) a first reagent that comprises an ester of a polyhydric alcohol and formic acid, and b) a second reagent that comprises a substance that generates hydrogen peroxide when in contact with a liquid, wherein said first reagent and said second reagent are comprised in a solid composition, and when it is time to generate peroxyformic acid, said solid composition is configured to be contacted with a liquid to form a liquid that comprises peroxyformic acid and has a pH below about 11, and pH of the formed liquid becomes about 8 or lower within about 1 minute after the contact between said solid composition and said liquid.

The present peroxyformic acid forming compositions can comprise any suitable ester of a polyhydric alcohol and formic acid. Typically, a polyhydric alcohol refers to a molecule with two or more hydroxyl (—OH) groups. An ester of a polyhydric alcohol and formic acid refers to an ester formed between a polyhydric alcohol and formic acid. Esters as referred to herein are considered 'water-less' systems as no additional water is added to the reaction. In some embodiments, the present peroxyformic acid forming compositions comprise glycerol formates, pentaerythritol formates, mannitol formates, propylene glycol formates, sorbitol formates and sugar formates. The present peroxyformic acid forming compositions can comprise any suitable sugar formates, e.g., sucrose formates, dextrin formates, maltodextrin formates, or starch formates.

In a preferred embodiment, a liquid reaction employs glycerol formates, pentaerythritol formates, mannitol formates, or propylene glycol formates. In a still further preferred embodiment, a liquid reaction employs glycerol formates. Beneficially, the glycerol formates rapidly undergo hydrolysis for peroxyformic acid generation according to the methods of the invention. In an aspect, the precursors provided do not include additional water added into the system which would negatively interfere with the kinetics of the reaction between the ester of a polyhydric alcohol and formic acid and hydrogen peroxide. In an aspect, the premixes and the peroxyformic acid forming composition do not add free water into the systems, which would negatively interfere with the ester, e.g. glycerol formates.

In a preferred embodiment, a solid reaction employs sugar formates e.g., sucrose formates, dextrin formates, maltodextrin formates, or starch formates. In a still further preferred embodiment, a solid reaction employs starch formates.

The present peroxyformic acid forming compositions can comprise a use solution or a concentrate of the ester of a polyhydric alcohol and formic acid. In some aspects, the methods of the invention generate a peroxyformic acid through a concentrate reaction of the ester of a polyhydric alcohol and formic acid. In other aspects, the methods of the invention generate a peroxyformic acid through a diluted use solution reaction of the ester of a polyhydric alcohol and formic acid.

The first or second reagent can have any suitable pH range in the present peroxyformic acid forming compositions. For example, the first or second reagent can have a pH below about 11, or from about −2 to about 11, or from about 0 to about 11, e.g., about −2 to about −1, −2 to about 0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11. In some embodiments, the first or second reagent has a pH ranging from about 5 to about 10, e.g., about 5-6, 5-7, 5-8, 5-9, 5-10, 6-7, 6-8, 6-9, 6-10, 7-8, 7-9, 7-10, 8-9, 8-10, or 9-10. In other embodiments, the first or second reagent has a pH at about 9.

The first reagent and the second reagent can be configured to be contacted with each other to form a liquid, e.g., a solution, that comprises peroxyformic acid and has any suitable pH, including a pH below about 11, or from about −2 to about 11, or from about 0 to about 11, e.g., about −2 to about −1, −2 to about 0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11. In some embodiments, the first reagent and the second reagent are configured to be contacted with each other to form a liquid, e.g., a solution, that comprises peroxyformic acid and has a pH ranging from about −2 to about 11, 0 to about 10, or 5 to about 10, e.g., about −2-0, 0-1, 1-2, 2-3, 3-4, 4-5, 5-6, 5-7, 5-8, 5-9, 5-10, 6-7, 6-8, 6-9, 6-10, 7-8, 7-9, 7-10, 8-9, 8-10, 9-10, or 10-11. In other embodiments, the first reagent and the second reagent are configured to be contacted with each other to form a liquid, e.g., a solution, that comprises peroxyformic acid and has a pH at about 9. In a preferred aspect, the formed liquid, e.g., a solution, that comprises peroxyformic acid and has a pH near neutral, from about 6-7.

The pH of the formed liquid can become about 8 or lower within about 1 minute after the contact between the first reagent and the second reagent or after the contact between the solid composition and the liquid. In some embodiments, the pH of the formed liquid can become about 8 or lower within about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds after the contact between the first reagent and the second reagent or after the contact between the solid composition and the liquid. In other embodiments, the pH of the formed liquid comprising peroxyformic acid becomes about 8 or lower within about 1 minute or less. In an aspect, the pH of the formed liquid comprising peroxyformic acid becomes about 8 or lower within about 45 seconds or less, 40 seconds or less, 35 seconds or less, 30 seconds or less, 25 seconds or less, 20 seconds or less, 15 seconds or less, 10 seconds or less, or 5 seconds or less. In an aspect, the pH of the formed liquid comprising peroxyformic acid becomes about 8 or lower near instantaneously. In other embodiments, the pH of the formed liquid can become about lower than −2, −1, 0, 1, 2, 3, 4, 5, 6, 7, or 8 within about 1 minute after the contact between the first reagent and the second reagent or after the contact between the solid composition and the liquid.

The liquid that comprises peroxyformic acid can maintain the pH ranging from about −2 to about 8, or from about 0 to about 8 for any suitable time after the contact between the first reagent and the second reagent, or after the contact between the composition and a liquid. In some embodiments, the liquid that comprises peroxyformic acid maintains the pH ranging from about −2 to about 8, or from about 0 to about 8 from about 1 second to about 10 hours after the contact between the first reagent and the second reagent or after the contact between the composition and a liquid. For example, the liquid that comprises peroxyformic acid can maintain the pH at about −2, −1, 0, 1, 2, 3, 4, 5, 6, 7, or 8 from about 1 second to about 10 hours after the contact between the first reagent and the second reagent or after the contact between the composition and a liquid. In another example, the liquid that comprises peroxyformic acid can maintain the pH ranging from about 0 to about 8 for about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In a preferred aspect, the formed liquid, e.g., a solution, that comprises peroxyformic acid and has a pH near neutral, from about 6-7 in a use solution.

In some embodiments, the first reagent and the second reagent are configured to be contacted with each other to form a solution that comprises peroxyformic acid and has a pH ranging from about 4 to about 8 or 9, e.g., about 4-5, 5-6, 6-7, 7-8, or 8-9. In a preferred aspect, the formed liquid, e.g., a solution, that comprises peroxyformic acid and has a pH near neutral, from about 6-7 in a use solution. In one example, the first reagent and the second reagent are configured to be contacted with each other to form a solution that comprises peroxyformic acid and has a pH ranging from about 6 to about 8 or 9. The first reagent and the second reagent can be configured to be contacted with each other to form a solution that comprises peroxyformic acid and has a pH ranging from about 4 to about 8 or 9, and the solution can maintain the pH range for any suitable amount of time, e.g., from about 1 minute to about 24 hours. For example, the solution can maintain the pH range from about 4 to about 8 or 9 for at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours.

In other embodiments, the solid composition is configured to be contacted with a liquid to form a solution that comprises peroxyformic acid and has a pH ranging from about 4 to about 8 or 9, e.g., about 4-5, 5-6, 6-7, 7-8, or 8-9. In one example, the solid composition is configured to be contacted with a liquid to form a solution that comprises peroxyformic acid and has a pH ranging from about 6 to about 8 or 9. The solid composition is configured to be contacted with a liquid to form a solution that comprises peroxyformic acid and has a pH ranging from about 4 to about 8 or 9, and the solution can maintain the pH range for any suitable amount of time, e.g., from about 1 minute to about 24 hours. For example, the solution can maintain the pH range from about 4 to about 8 or 9 for at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In a preferred aspect, the formed liquid, e.g., a solution, that comprises peroxyformic acid and has a pH near neutral, from about 6-7 in a use solution.

The first reagent and the second reagent can be configured to be contacted with each other to form a liquid, e.g., a solution, that comprises peroxyformic acid under any suitable conditions or temperature. In some embodiments, the first reagent and the second reagent are configured to be contacted with each other to form a liquid, e.g., a solution, that comprises peroxyformic acid under ambient conditions. In other embodiments, the first reagent and the second reagent are configured to be contacted with each other to form a liquid, e.g., a solution, that comprises peroxyformic acid at a temperature ranging from about $-2°$ C. to about $60°$ C., $0°$ C. to about $60°$ C., or $4°$ C. to about $60°$ C., e.g., about $-2°$ C.-$0°$ C., $0°$ C.-$4°$ C., $4°$ C.-$5°$ C., $4°$ C.-$5°$ C., $5°$ C.-$10°$ C., $10°$ C.-$15°$ C., $15°$ C.-$20°$ C., $20°$ C.-$25°$ C., $25°$ C.-$30°$ C., $30°$ C.-$35°$ C., $35°$ C.-$40°$ C., $40°$ C.-$45°$ C., $45°$ C.-$50°$ C., $50°$ C.-$55°$ C., or $55°$ C.-$60°$ C. In still other embodiments, the first reagent and the second reagent are configured to be contacted with each other to form a liquid, e.g., a solution, that comprises peroxyformic acid at a temperature at about $4°$ C. or lower than $4°$ C., e.g., at about $3°$ C., $2°$ C., $1°$ C., $0°$ C., or lower than $0°$ C.

The solid composition can be configured to be contacted with a liquid to form a liquid, e.g., a solution, that comprises peroxyformic acid under any suitable conditions or temperature. In some embodiments, the solid composition can be configured to be contacted with a liquid to form a liquid, e.g., a solution, that comprises peroxyformic acid under ambient conditions. In other embodiments, the solid composition can be configured to be contacted with a liquid to form a liquid, e.g., a solution, that comprises peroxyformic acid at a temperature ranging from about $-2°$ C. to about $60°$ C., $0°$ C. to about $60°$ C., or $4°$ C. to about $60°$ C., e.g., about $-2°$ C.-$0°$ C., $0°$ C.-$4°$ C., $4°$ C.-$5°$ C., $4°$ C.-$5°$ C., $5°$ C.-$10°$ C., $10°$ C.-$15°$ C., $15°$ C.-$20°$ C., $20°$ C.-$25°$ C., $25°$ C.-$30°$ C., $30°$ C.-$35°$ C., $35°$ C.-$40°$ C., $40°$ C.-$45°$ C., $45°$ C.-$50°$ C., $50°$ C.-$55°$ C., or $55°$ C.-$60°$ C. In still other embodiments, the solid composition can be configured to be contacted with a liquid to form a liquid, e.g., a solution, that comprises peroxyformic acid at a temperature at about $4°$ C. or lower than $4°$ C., e.g., at about $3°$ C., $2°$ C., $1°$ C., $0°$ C., or lower than $0°$ C.

The present peroxyformic acid forming compositions can further comprise a catalyst (e.g. mineral acid) or an enzyme that catalyzes formation of peroxyformic acid from the ester of a polyhydric alcohol and formic acid, and hydrogen peroxide. The present peroxyformic acid forming compositions can comprise any suitable catalyst, e.g., a strong mineral acid, or enzyme, e.g., a perhydrolytic enzyme, lipase, coronase, termanyl or esperease. The catalyst or an enzyme can be comprised in any suitable part of the present peroxyformic acid forming compositions. In some embodiments, the first reagent comprises the catalyst or enzyme. In other embodiments, the second reagent comprises the catalyst or enzyme. In still other embodiments, the present peroxyformic acid forming compositions can further comprise a third reagent that comprises the catalyst or enzyme. In yet other embodiments, the solid composition comprises the catalyst or enzyme.

The present peroxyformic acid forming compositions can further comprise a stabilizing agent for peroxyformic acid, a stabilizing agent for hydrogen peroxide, and/or a pH buffering agent. In an aspect the stabilizing agent(s) and/or pH buffering agents are useful in decreasing a pH of the compositions to neutral or lower pH. The present peroxyformic acid forming compositions can comprise any suitable stabilizing agent. Exemplary stabilizing agents include a phosphonate salt(s) and/or a heterocyclic dicarboxylic acid, e.g., dipicolinic acid. In some embodiments, the stabilizing agent is pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts. In other embodiments, the present peroxyformic acid forming compositions comprise two or more stabilizing agents, e.g., HEDP and 2,6-pyridinedicarboxylic acid (DPA).

The stabilizing agent(s) can be comprised in any suitable part of the present peroxyformic acid forming compositions. In some embodiments, the first reagent comprises a stabilizing agent for peroxyformic acid and/or a pH buffering agent. In other embodiments, the second reagent comprises a stabilizing agent for hydrogen peroxide. In still other embodiments, the present peroxyformic acid forming compositions can further comprise a third reagent that comprises a stabilizing agent for peroxyformic acid, a stabilizing agent for hydrogen peroxide, and/or a pH buffering agent. In yet other embodiments, the solid composition comprises a stabilizing agent for peroxyformic acid, a stabilizing agent for hydrogen peroxide, and/or a pH buffering agent.

The present peroxyformic acid forming compositions can comprise any suitable pH buffering agent. The pH buffer reagent can include any reagent that is compatible with the ester(s) in the present peroxyformic acid forming compositions. Exemplary buffer agents suitable for using with a liquid ester can be an organic amine, such as triethanol amine, imidazole, etc. Exemplary buffer agents suitable for using with a solid form of ester include a broader range of buffers, such as a carbonate salt, a phosphate salt, etc. The pH buffer reagent can be comprised in any suitable part of the present peroxyformic acid forming compositions. In some embodiments, the first reagent comprises a pH buffering agent. In other embodiments, the present peroxyformic acid forming compositions can further comprise a third reagent that comprises a pH buffering agent. In still other embodiments, the solid composition comprises a pH buffering agent.

The present peroxyformic acid forming compositions can comprise any suitable stabilizing agent for hydrogen peroxide. Exemplary stabilizing agents for hydrogen peroxide include phosphonates, heterocyclic carboxylic acids and the mixtures thereof. In some embodiments, stabilizing agents for hydrogen peroxide can be Dequest 2010, Dequest 2066, Dipicolinic acids, etc. The stabilizing agent for hydrogen peroxide can be comprised in any suitable part of the present peroxyformic acid forming compositions. In some embodiments, the second reagent comprises a stabilizing agent for hydrogen peroxide. In other embodiments, the present peroxyformic acid forming compositions can further comprise a third reagent that comprises a stabilizing agent for hydrogen peroxide. In still other embodiments, the solid composition comprises a stabilizing agent for hydrogen peroxide.

The present peroxyformic acid forming compositions can comprise any suitable number of dosage(s) of the first reagent that is kept separately prior to use, and is used to contact the second reagent that comprises hydrogen peroxide. For example, the present peroxyformic acid forming compositions can comprise a single dosage of the first reagent that is kept separately prior to use, and is used to contact the second reagent that comprises hydrogen peroxide. In another example, the present peroxyformic acid forming compositions can comprise multiple dosages of the first reagent that are kept separately prior to use, and are used to contact the second reagent that comprises hydrogen peroxide, either simultaneously or sequentially. The multiple dosages of the first reagent can comprise any suitable ester(s) of a polyhydric alcohol and formic acid. For example, the multiple dosages of the first reagent can comprise the same ester of a polyhydric alcohol and formic acid. In another example, the multiple dosages of the first reagent can comprise different esters of polyhydric alcohols and formic acid. The multiple dosages of the first reagent can comprise the same or different concentrations of ester(s) of a polyhydric alcohol and formic acid. In still another example, the present peroxyformic acid forming compositions can comprise multiple dosages of the solid composition that are kept separately prior to use.

The present peroxyformic acid forming compositions can comprise any suitable concentration of an ester of a polyhydric alcohol and formic acid. For example, the first reagent of the peroxyformic acid forming composition can comprise any suitable concentration of an ester of a polyhydric alcohol and formic acid. In some embodiments, the formed liquid is a concentrate and comprises the first reagent in an amount up to about 90% of an ester of a polyhydric alcohol and formic acid. In other embodiments, the formed liquid comprises the first reagent in an amount from about 1 ppm to about 500,000 ppm of an ester of a polyhydric alcohol and formic acid, or from about 10 ppm to about 500,000 ppm of an ester of a polyhydric alcohol and formic acid. For example, the first reagent in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm. In other embodiments, the first reagent in the formed liquid can comprise from about 50 ppm to about 40,000 ppm of an ester of a polyhydric alcohol and formic acid, e.g., 50-100, 50-500, 50-1,000, 50-1,500, 50-2,000, 50-2,500, 50-3,000, 50-3,500, 50-4,000, 50-4,500, 50-5,000, 50-10,000, 50-20,000, 50-30,000, or 50-40,000 ppm of an ester of a polyhydric alcohol and formic acid.

In another example, the solid composition of the peroxyformic acid forming composition can comprise any suitable concentration of an ester of a polyhydric alcohol and formic acid. In some embodiments, the solid composition can provide a concentrate formed liquid that comprises the first reagent in an amount up to about 90% of an ester of a polyhydric alcohol and formic acid. In other embodiments, the solid composition can provide for the formed liquid from about 10 ppm to about 500,000 ppm of an ester of a polyhydric alcohol and formic acid. For example, the solid composition can provide for the formed liquid the ester of a polyhydric alcohol and formic acid in amounts comprising from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm. In other embodiments, the solid composition can provide for the formed liquid from about 50 ppm to about 40,000 ppm of an ester of a polyhydric alcohol and formic acid, e.g., 50-100, 50-500, 50-1,000, 50-1,500, 50-2,000, 50-2,500, 50-3,000, 50-3,500, 50-4,000, 50-4,500, 50-5,000, 50-10,000, 50-20,000, 50-30,000, or 50-40,000 ppm of an ester of a polyhydric alcohol and formic acid.

The present peroxyformic acid forming compositions can comprise any suitable concentration of hydrogen peroxide or a substance that generates hydrogen peroxide upon contact with a liquid. For example, the second reagent of the peroxyformic acid forming composition can comprise any suitable concentration of hydrogen peroxide. In some embodiments, a concentrate formed liquid comprises the second reagent in an amount up to about 10% of hydrogen peroxide. In some embodiments, the formed liquid comprises the second reagent in an amount comprising about 0.1 ppm to about 100,000 ppm of hydrogen peroxide, or about 0.1 ppm to about 100,000 ppm of hydrogen peroxide. For example, the second reagent in the formed liquid can comprise from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm, 100,000-150,000 ppm, 150,000-200,000 ppm, 200,000-250,000 ppm, or 250,000-300,000 ppm hydrogen peroxide. In other embodiments, the second reagent in the formed liquid comprises from about 150 ppm to about 50,000 ppm of hydrogen peroxide, e.g., about 150-200, 150-300, 150-400, 150-500, 150-600, 150-700, 150-800, 150-900, 150-1,000, 150-1,500, 150-2,000, 150-2,500, 150-3,000, 150-3,500, 150-4,000, 150-4,500, 150-5,000, 150-10,000, 50-20,000, 50-30,000, 50-40,000 or 50-50,000 ppm of hydrogen peroxide.

In some embodiments, a concentrate formed liquid comprises the second reagent in an amount up to about 10% of hydrogen peroxide. In another example, the solid composition can comprise a substance at an amount or concentration that generates from about 0.1 ppm to about 100,000 ppm of hydrogen peroxide upon contact with a liquid in the formed liquid. For example, the solid composition can comprise a substance at an amount or concentration that generates from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm hydrogen peroxide.

The present peroxyformic acid forming compositions can be configured to form a liquid, e.g., a solution, that comprises any suitable concentration of peroxyformic acid. For example, the first reagent and the second reagent in the present peroxyformic acid forming compositions can be configured to be contacted with each other to form a liquid and/or solid, e.g., a solution, that comprises any suitable concentration of peroxyformic acid. In some embodiments, the first reagent and the second reagent can be configured to be contacted with each other to form a liquid, e.g., a solution, that comprises from about 0.1 ppm to about 100,000 ppm of peroxyformic acid, from about 0.1 ppm to about 10,000 ppm of peroxyformic acid, or from about 0.1 ppm to about 5,000 ppm of peroxyformic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm or greater of peroxyformic acid. In other embodiments, the first reagent and the second reagent can be configured to be contacted with each other to form a liquid, e.g., a solution, that comprises from about 1 ppm to about 500 ppm of peroxyformic acid, e.g., about 0.1-1 ppm, 0.1-10 ppm, 0.1-20 ppm, 0.1-30 ppm, 0.1-40 ppm, 0.1-50 ppm, 0.1-60 ppm, 0.1-70 ppm, 0.1-80 ppm, 0.1-90 ppm, 0.1-100 ppm, 0.1-150 ppm, 0.1-200 ppm, 0.1-250 ppm, 0.1-300 ppm, 0.1-350 ppm, 0.1-400 ppm, 0.1-450 ppm, 0.1-500 ppm of peroxyformic acid. In still other embodiments, the first reagent and the second reagent can be configured to be contacted with each other to form a liquid, e.g., a solution, that comprises from about 50 ppm to about 100 ppm of peroxyformic acid, e.g., about 50-60 ppm, 60-70 ppm, 70-80 ppm, 80-90 ppm or 90-100 ppm of peroxyformic acid. In yet other embodiments, the first reagent and the second reagent can be configured to be contacted with each other to form a liquid, e.g., a solution, that comprises from about 200 ppm to about 300 ppm of peroxyformic acid, e.g., about 200-210 ppm, 210-220 ppm, 220-230 ppm, 230-240 ppm, 240-250 ppm, 250-260 ppm, 260-270 ppm, 270-280 ppm, 280-290 ppm, 290-300 ppm of peroxyformic acid.

In another example, the solid composition can be configured to be contacted with a liquid to form a solution that comprises from about 0.1 ppm to about 100,000 ppm of peroxyformic acid, from about 0.1 ppm to about 10,000 ppm of peroxyformic acid, or from about 0.1 ppm to about 5,000 ppm of peroxyformic acid. In some embodiments, the solid composition can be configured to be contacted with a liquid to form a liquid, e.g., a solution, that comprises from about 0.1 ppm to about 5,000 ppm of peroxyformic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm or greater of peroxyformic acid.

The present peroxyformic acid forming compositions can be configured to form a liquid, e.g., a solution, that comprises any suitable concentration of peroxyformic acid within any suitable time. For example, the first reagent and the second reagent in the present peroxyformic acid forming compositions can be configured to be contacted with each other to form a liquid and/or solid, e.g., a solution, that comprises any suitable concentration of peroxyformic acid within any suitable time. In some embodiments, the first reagent and the second reagent can be configured to be contacted with each other to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm or greater of peroxyformic acid within 1 minute of the contact time.

In another example, the solid composition can be configured to be contacted with a liquid to form a liquid, e.g., a solution, that comprises any suitable concentration of peroxyformic acid within any suitable time. In some embodiments, the solid composition can be configured to be contacted with a liquid to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm or greater, of peroxyformic acid within 1 minute of the contact time.

In an aspect, at least about 1 ppm peroxyformic is generated within less than 1 minute of contacting the first reagent and the second reagent. In an aspect, at least about 1 ppm peroxyformic is generated within less than about 55 seconds, 50 seconds or less, 45 seconds or less, 40 seconds or less, 35 seconds or less, 30 seconds or less, 25 seconds or less, 20 seconds or less, 15 seconds or less, 10 seconds or less, or 5 seconds or less. In an aspect, the reaction to form a liquid comprising at least about 1 ppm peroxyformic acid is near instantaneous.

In an aspect, at least about 100 ppm or at least about 500 ppm peroxyformic is generated within about 5 minutes or less of contacting the first reagent and the second reagent. In an aspect, at least about 100 ppm or 500 ppm peroxyformic is generated within less than about 4 minutes, 3 minutes or less, 2 minutes or less, or 1 minute or less.

The present peroxyformic acid forming compositions can be configured to form a liquid, e.g., a solution, that comprises any suitable percentage of the peak concentration of peroxyformic acid within any suitable time. For example, the first reagent and the second reagent in the present peroxyformic acid forming compositions can be configured to be contacted with each other to form a liquid, e.g., a solution, that comprises any suitable percentage of the peak concentration of peroxyformic acid within any suitable time. In some embodiments, the first reagent and the second reagent are configured to be contacted with each other to form a liquid, e.g., a solution, that comprises at least about 80% of the peak concentration of peroxyformic acid within from about 5 minutes to about 15 minutes of the contact time. For example, the first reagent and the second reagent are configured to be contacted with each other to form a liquid, e.g., a solution, that comprises at least about 80%, 85%, 90%, 95%, 96%, 97%, 98%, 99% or 100% of the peak concentration of peroxyformic acid within from about 5 minutes to about 15 minutes of the contact time. In another example, the first reagent and the second reagent are configured to be contacted with each other to form a liquid, e.g., a solution, that comprises at least about 80% of the peak concentration of peroxyformic acid within from about 5, 6, 7, 8, 9, 10, 11, 12, 13, 14 or 15 minutes of the contact time.

In another example, the solid composition can be configured to be contacted with a liquid to form a liquid, e.g., a solution, that comprises any suitable percentage of the peak concentration of peroxyformic acid within any suitable time. In some embodiments, the solid composition can be configured to be contacted with a liquid to form a liquid, e.g., a solution, that comprises at least about 80% of the peak concentration of peroxyformic acid within from about 5 minutes to about 15 minutes of the contact time. For example, the solid composition can be configured to be contacted with a liquid to form a liquid, e.g., a solution, that comprises at least about 80%, 85%, 90%, 95%, 96%, 97%, 98%, 99% or 100% of the peak concentration of peroxyformic acid within from about 5 minutes to about 15 minutes of the contact time. In another example, the solid composition can be configured to be contacted with a liquid to form a liquid, e.g., a solution, that comprises at least about 80% of the peak concentration of peroxyformic acid within from about 5, 6, 7, 8, 9, 10, 11, 12, 13, 14 or 15 minutes of the contact time.

The formed peroxyformic acid can maintain any suitable percentage of the peak concentration of peroxyformic acid within any suitable time. In some embodiments, the formed peroxyformic acid can maintain at least about 50% of the peak concentration from about 5 minutes to about 25 minutes after the contact between the first reagent and the second reagent or after the contact between the solid composition and a liquid. For example, the formed peroxyformic acid can maintain at least about 50%, 55%, 60%, 65%, 70%, 75%, 80%, 85%, 90%, 95%, 96%, 97%, 98%, 99% or 100% of the peak concentration from about 5 minutes to about 25 minutes after the contact between the first reagent and the second reagent or after the contact between the solid composition and a liquid. In another example, the formed peroxyformic acid can maintain at least about 50% of the peak concentration from about 5-25 minutes, e.g., about 5, 6, 7, 8, 9, 10, 11, 12, 13, 14, 15, 16, 17, 18, 19, 20, 21, 22, 23, 24 or 25 minutes, after the contact between the first reagent and the second reagent or after the contact between the solid composition and a liquid.

In some embodiments, the first reagent and the second reagent of the present peroxyformic acid forming composition are configured to be contacted with each other to form a solution that comprises at least about 80% of the peak concentration of peroxyformic acid within from about 1 minute to about 15 minutes of the contact time. In other embodiments, the formed peroxyformic acid maintains at least about 50% of the peak concentration from about 1 minute to about 15 minutes after the contact between the first reagent and the second reagent. In still other embodiments, the solid composition can be configured to be contacted with a liquid to form a solution that comprises at least about 80% of the peak concentration of peroxyformic acid within from about 1 minute to about 15 minutes of the contact time. In other embodiments, the formed peroxyformic acid maintains at least about 50% of the peak concentration from about 1 minute to about 15 minutes after the contact between the solid composition and the liquid.

In preferred aspects of the invention the desired peak concentration of peroxyformic acid is 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, 5,000 ppm, 6,000 ppm, 7,000 ppm, 8,000 ppm, 9,000 ppm, 10,000 ppm or more (inclusive of any ranges therein).

The present peroxyformic acid forming compositions can further comprise a $C_2$-$C_{22}$ percarboxylic acid, and wherein the first reagent or the solid composition comprising the first reagent and the second reagent are kept separately from the $C_2$-$C_{22}$ percarboxylic acid prior to generate peroxyformic acid. The present peroxyformic acid forming compositions can comprise any suitable $C_2$-$C_{22}$ percarboxylic acid, e.g., peroxyacetic acid, peroxyoctanoic acid and/or peroxysulfonated oleic acid.

In some embodiments, the present peroxyformic acid forming compositions do not comprise a perhyrolysis enzyme. For example, in some cases, the present peroxyformic acid forming compositions do not comprise a member of family 7 of the carbohydrate esterases (CE-7) or a perhyrolysis enzyme that is disclosed in U.S. patent application 2013/0289113.

Methods for Forming Peroxyformic Acid

In another aspect, the present invention is directed to a method for forming peroxyformic acid comprising: a) contacting a first reagent that comprises an ester of a polyhydric alcohol and formic acid, and a second reagent that comprises hydrogen peroxide or that comprises a substance that generates hydrogen peroxide when in contact with a liquid to form a liquid that comprises peroxyformic acid and has a pH below about 11, or from −2 to about 11, or from 0 to about 11 (or any range therein), wherein said first reagent and said second reagent are kept separately prior to said contacting and pH of said formed liquid becomes about 8 or lower within about 1 minute after the contact between said first reagent and said second reagent; or b) contacting a solid composition that comprises a first reagent that comprises an ester of a polyhydric alcohol and formic acid, and a second reagent that comprises a substance that generates hydrogen peroxide when in contact with a liquid with a liquid to form a liquid that comprises peroxyformic acid and has a pH below about 11, or from −2 to about 11, or from 0 to about 11, and pH of said formed liquid becomes about 8 or lower within about 1 minute after the contact between said solid composition and said liquid.

In some embodiments, the present methods comprise contacting a first reagent that comprises an ester of a polyhydric alcohol and formic acid, and a second reagent that comprises hydrogen peroxide or that comprises a substance that generates hydrogen peroxide when in contact with a liquid to form a liquid that comprises peroxyformic acid and has a pH below about 11, or from −2 to about 11, or from 0 to about 11 (or any range therein), wherein said first reagent and said second reagent are kept separately prior to said contacting and pH of said formed liquid becomes about 8 or lower within about 1 minute after the contact between said first reagent and said second reagent. In other embodiments, the present methods comprise contacting a solid composition that comprises a first reagent that comprises an ester of a polyhydric alcohol and formic acid, and a second reagent that comprises a substance that generates hydrogen peroxide when in contact with a liquid with a liquid to form a liquid that comprises peroxyformic acid and has a pH below about 11, or from −2 to about 11, or from 0 to about 11, and pH of said formed liquid becomes about 8 or lower within about 1 minute after the contact between said solid composition and said liquid.

Any suitable ester of a polyhydric alcohol and formic acid can be used in the present methods. Typically, a polyhydric alcohol refers to a molecule with two or more hydroxyl (—OH) groups. An ester of a polyhydric alcohol and formic acid refers to an ester formed between a polyhydric alcohol and formic acid. In some embodiments, glycerol formates, pentaerythritol formates, mannitol formates, propylene glycol formates, sorbitol formates and sugar formates can be used in the present methods. Any suitable sugar formates can be used in the present methods, e.g., sucrose formates, dextrin formates, maltodextrin formates, or starch formates.

The first reagent or second reagent used in the present methods can have any suitable pH range. For example, the first reagent or second reagent can have a pH below about 11, or from −2 to about 11, or from about 0 to about 11, e.g., about −2 to about −1, −1-0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11. In some embodiments, the first reagent or second reagent has a pH ranging from about 5 to about 10, e.g., about 5-6, 5-7, 5-8, 5-9, 5-10, 6-7, 6-8, 6-9, 6-10, 7-8, 7-9, 7-10, 8-9, 8-10, or 9-10. In other embodiments, the first reagent or second reagent has a pH at about 9.

The first reagent and the second reagent can be contacted with each other to form a liquid, e.g., a solution, that comprises peroxyformic acid and has any suitable pH below about 11, or from −2 to about 11, or from about 0 to about 11, e.g., about −2 to about −1, −1-0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11.

In some embodiments, the first reagent and the second reagent are contacted with each other to form a liquid, e.g., a solution, that comprises peroxyformic acid and has a pH ranging from about 5 to about 10, e.g., about 5-6, 5-7, 5-8, 5-9, 5-10, 6-7, 6-8, 6-9, 6-10, 7-8, 7-9, 7-10, 8-9, 8-10, or 9-10. In other embodiments, the first reagent and the second reagent are contacted with each other to form a liquid, e.g., a solution, that comprises peroxyformic acid and has a pH at about 9. The a solid composition can be contacted with a liquid to form a liquid, e.g., a solution, that comprises peroxyformic acid and has any suitable pH below about 11, or from −2 to about 11, or from about 0 to about 11, e.g., about −2 to about −1, −1-0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11. The pH of the formed liquid can become about 8 or lower within about 1 minute after the contact between the first reagent and the second reagent or after the contact between the solid composition and the liquid. In some embodiments, the pH of the formed liquid can become about 8 or lower within about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds after the contact between the first reagent and the second reagent or after the contact between the solid composition and the liquid. In other embodiments, the pH of the formed liquid can become about lower than 0, 0, 1, 2, 3, 4, 5, 6, 7, 8 within about 1 minute after the contact between the first reagent and the second reagent or after the contact between the solid composition and the liquid. In an aspect, the pH of the formed liquid comprising peroxyformic acid becomes about 8 or lower within about 1 minute or less. In an aspect, the pH of the formed liquid comprising peroxyformic acid becomes about 8 or lower within about 45 seconds or less, 40 seconds or less, 35 seconds or less, 30 seconds or less, 25 seconds or less, 20 seconds or less, 15 seconds or less, 10 seconds or less, or 5 seconds or less. In an aspect, the pH of the formed liquid comprising peroxyformic acid becomes about 8 or lower near instantaneously.

The liquid that comprises peroxyformic acid can maintain the pH ranging from about 0 to about 8 for any suitable time after the contact between the first reagent and the second reagent, or after the contact between the composition and a liquid. In some embodiments, the liquid that comprises peroxyformic acid maintains the pH ranging from about −2 to about 11, about 0 to about 11, or 0 to about 8 from about 1 second to about 10 hours after the contact between the first reagent and the second reagent or after the contact between the composition and a liquid. For example, the liquid that comprises peroxyformic acid can maintain the pH at about −2, −1, 0, 1, 2, 3, 4, 5, 6, 7, or 8 from about 1 second to about 10 hours after the contact between the first reagent and the second reagent or after the contact between the composition and a liquid. In another example, the liquid that comprises peroxyformic acid can maintain the pH ranging from about 0 to about 8 for about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours.

In some embodiments, the first reagent and the second reagent can be contacted with each other to form a solution that comprises peroxyformic acid and has a pH ranging from about 4 to about 8 or 9, e.g., about 4-5, 5-6, 6-7, 7-8, or 8-9. In one example, the first reagent and the second reagent are contacted with each other to form a solution that comprises peroxyformic acid and has a pH ranging from about 6 to about 8 or 9. The first reagent and the second reagent can be contacted with each other to form a solution that comprises peroxyformic acid and has a pH ranging from about 4 to about 8 or 9, and the solution can maintain the pH range for any suitable amount of time, e.g., from about 1 minute to about 24 hours. For example, the solution can maintain the pH range from about 4 to about 8 or 9 for at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours.

In other embodiments, the solid composition can be contacted with a liquid to form a solution that comprises peroxyformic acid and has a pH ranging from about 4 to about 8 or 9, e.g., about 4-5, 5-6, 6-7, 7-8, or 8-9. In one example, the solid composition is contacted with a liquid to form a solution that comprises peroxyformic acid and has a pH ranging from about 6 to about 8 or 9. The solid composition can be contacted with a liquid to form a solution that comprises peroxyformic acid and has a pH ranging from about 4 to about 8 or 9, and the solution can maintain the pH range for any suitable amount of time, e.g., from about 1 minute to about 24 hours. For example, the solution can maintain the pH range from about 4 to about 8 or 9 for at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours.

The first reagent and the second reagent can be contacted with each other to form a liquid, e.g., a solution, that comprises peroxyformic acid under any suitable conditions or temperature. In some embodiments, the first reagent and the second reagent can be contacted with each other to form a liquid, e.g., a solution, that comprises peroxyformic acid under ambient conditions. In other embodiments, the first reagent and the second reagent can be contacted with each other to form a liquid, e.g., a solution, that comprises peroxyformic acid at a temperature ranging from about $-2°$ C. to about 60° C., 0° C. to about 60° C., or 4° C. to about 60° C., e.g., about $-2°$ C.-0° C., 0° C.-4° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C. In still other embodiments, the first reagent and the second reagent can be contacted with each other to form a liquid, e.g., a solution, that comprises peroxyformic acid at a temperature at about 4° C. or lower than 4° C., e.g., at about 3° C., 2° C., 1° C., 0° C., or lower than 0° C.

The solid composition can be contacted with a liquid to form a liquid, e.g., a solution, that comprises peroxyformic acid under any suitable conditions or temperature. In some embodiments, the solid composition can be contacted with a liquid to form a liquid, e.g., a solution, that comprises peroxyformic acid under ambient conditions. In other embodiments, the solid composition can be contacted with a liquid to form a liquid, e.g., a solution, that comprises peroxyformic acid at a temperature ranging from about $-2°$ C. to about 60° C., 0° C. to about 60° C., or 4° C. to about 60° C., e.g., about $-2°$ C.-0° C., 0° C.-4° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C. In still other embodiments, the solid composition can be contacted with a liquid to form a liquid, e.g., a solution, that comprises peroxyformic acid at a temperature at about 4° C. or lower than 4° C., e.g., at about 3° C., 2° C., 0° C., 0° C., or lower than 0° C.

The present methods can further comprise using a catalyst or an enzyme that catalyzes formation of peroxyformic acid from the ester of a polyhydric alcohol and formic acid, and hydrogen peroxide. The present methods can use any suitable catalyst or enzyme, e.g., a perhydrolytic enzyme, lipase, coronase, termanyl or esperease. The catalyst or an enzyme can be comprised in any suitable reagent. In some embodiments, the first reagent comprises the catalyst or enzyme. In other embodiments, the second reagent comprises the catalyst or enzyme. In still other embodiments, the present methods can further comprise using a third reagent that comprises the catalyst or enzyme. In yet other embodiments, the solid composition comprises the catalyst or enzyme.

The present methods can further comprise using a stabilizing agent for peroxyformic acid, a stabilizing agent for hydrogen peroxide, and/or a pH buffering agent. The present methods can use any suitable stabilizing agent. Exemplary stabilizing agents include a phosphonate salt(s) and/or a heterocyclic dicarboxylic acid, e.g., dipicolinic acid. In some embodiments, the stabilizing agent is pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts. In other embodiments, the present methods can use two or more stabilizing agents, e.g., HEDP and 2,6-pyridinedicarboxylic acid (DPA).

The stabilizing agent(s) can be comprised in any suitable reagent. In some embodiments, the first reagent comprises a stabilizing agent for peroxyformic acid and/or a pH buffering agent. In other embodiments, the second reagent comprises a stabilizing agent for hydrogen peroxide. In still other embodiments, the present methods can further comprise using a third reagent that comprises a stabilizing agent for peroxyformic acid, a stabilizing agent for hydrogen peroxide, and/or a pH buffering agent. In yet other embodiments, the solid composition comprises a stabilizing agent for peroxyformic acid, a stabilizing agent for hydrogen peroxide, and/or a pH buffering agent.

The present methods can use any suitable pH buffering agent. The pH buffer reagent can include any reagent that is compatible with the ester(s) used in the present methods. Exemplary buffer agents suitable for using with a liquid ester can be an organic amine, such as triethanol amine, imidazole, etc. Exemplary buffer agents suitable for using with a solid form of ester include a broader range of buffers, such as a carbonate salt, a phosphate salt, etc. The pH buffer reagent can be comprised in any suitable reagent. In some embodiments, the first reagent comprises a pH buffering agent. In other embodiments, the solid composition comprises a pH buffering agent.

The present methods can use any suitable stabilizing agent for hydrogen peroxide. Exemplary stabilizing agents for hydrogen peroxide include phosphonates, heterocyclic carboxylic acids and the mixtures thereof. In some embodiments, stabilizing agents for hydrogen peroxide can be Dequest 2010, Dequest 2066, Dipicolinic acids, etc. The stabilizing agent for hydrogen peroxide can be comprised in any suitable reagent. In some embodiments, the second reagent comprises a stabilizing agent for hydrogen peroxide. In other embodiments, the present methods can further comprise using a third reagent that comprises a stabilizing agent for hydrogen peroxide. In still other embodiments, the solid composition comprises a stabilizing agent for hydrogen peroxide.

The present methods can use any suitable number of dosage(s) of the first reagent that is kept separately prior to use, and is used to contact the second reagent that comprises hydrogen peroxide. For example, the present methods can use a single dosage of the first reagent that is kept separately prior to use, and is used to contact the second reagent that comprises hydrogen peroxide. In another example, the present methods can use multiple dosages of the first reagent that are kept separately prior to use, and are used to contact the second reagent that comprises hydrogen peroxide, either simultaneously or sequentially. The multiple dosages of the first reagent comprise any suitable ester(s) of a polyhydric alcohol and formic acid. For example, the multiple dosages of the first reagent can comprise the same ester of a polyhydric alcohol and formic acid. In another example, the multiple dosages of the first reagent can comprise different esters of polyhydric alcohols and formic acid. The multiple dosages of the first reagent can comprise the same or different concentrations of ester(s) of a polyhydric alcohol and formic acid. In still another example, the present methods can use multiple dosages of the solid composition that are kept separately prior to use.

The present methods can use any suitable concentration of an ester of a polyhydric alcohol and formic acid. For example, the first reagent of the peroxyformic acid forming composition can comprise any suitable concentration of an ester of a polyhydric alcohol and formic acid. In some embodiments, the formed liquid is a concentrate and comprises the first reagent in an amount up to about 90% of an ester of a polyhydric alcohol and formic acid to form the peroxyformic acid. In some embodiments, the amount of first reagent in the formed liquid to generate the peroxyformic acid can comprise from about 1 ppm to about 500,000 ppm of an ester of a polyhydric alcohol and formic acid, or from about 10 ppm to about 500,000 ppm of an ester of a polyhydric alcohol and formic acid. For example, the first reagent in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm. In other embodiments, the first reagent can comprise from about 50 ppm to about 40,000 ppm of an ester of a polyhydric alcohol and formic acid, e.g., 50-100, 50-500, 50-1,000, 50-1,500, 50-2,000, 50-2,500, 50-3,000, 50-3,500, 50-4,000, 50-4,500, 50-5,000, 50-10,000, 50-20,000, 50-30,000, or 50-40,000 ppm of an ester of a polyhydric alcohol and formic acid.

In another example, the solid composition of the peroxyformic acid forming composition can comprise any suitable concentration of an ester of a polyhydric alcohol and formic acid. In some embodiments, the solid composition can provide for the formed liquid a concentrate comprising up to about 90% of an ester of a polyhydric alcohol and formic acid to form the peroxyformic acid. In some embodiments, the solid composition can provide for the formed liquid amounts from about 1 ppm to about 500,000 ppm of an ester of a polyhydric alcohol and formic acid, or from about 10 ppm to about 500,000 ppm of an ester of a polyhydric alcohol and formic acid. For example, the solid composition can provide for the formed liquid amounts from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm. In other embodiments, the solid composition can comprise sufficient amount of the esters for the formed liquid to comprise from about 50 ppm to about 40,000 ppm of an ester of a polyhydric alcohol and formic acid, e.g., 50-100, 50-500, 50-1,000, 50-1,500, 50-2,000, 50-2,500, 50-3,000, 50-3,500, 50-4,000, 50-4,500, 50-5,000, 50-10,000, 50-20,000, 50-30,000, or 50-40,000 ppm of an ester of a polyhydric alcohol and formic acid.

The present methods can use any suitable concentration of hydrogen peroxide or a substance that generates hydrogen peroxide upon contact with a liquid. For example, the second reagent of the peroxyformic acid forming composition can comprise any suitable concentration of hydrogen peroxide. In some embodiments, the second reagent can provide for the formed liquid a concentrate comprising up to about 10% of the hydrogen peroxide. In some embodiments, the formed liquid can comprise the second reagent in amounts from about 0.1 ppm to about 100,000 ppm of hydrogen peroxide, or from about 1 ppm to about 100,000 ppm of hydrogen peroxide. For example, the second reagent in the formed liquid can comprise from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm hydrogen peroxide. In other embodiments, the second reagent in the formed liquid comprises from about 150 ppm to about 50,000 ppm of hydrogen peroxide, e.g., about 150-200, 150-300, 150-400, 150-500, 150-600, 150-700, 150-800, 150-900, 150-1,000, 150-1,500, 150-2,000, 150-2,500, 150-3,000, 150-3,500, 150-4,000, 150-4,500, 150-5,000, 150-10,000, 50-20,000, 50-30,000, 50-40,000 or 50-50,000 ppm of hydrogen peroxide.

In another example, the solid composition can comprise a substance at an amount or concentration that generates from about 0.1 ppm to about 100,000 ppm of hydrogen peroxide, or from about 1 ppm to about 100,000 ppm of hydrogen peroxide in the formed liquid. For example, the solid composition can comprise a substance at an amount or concentration that generates from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, or 250,000-300,000 ppm hydrogen peroxide in the formed liquid.

The present methods can be used to form a liquid, e.g., a solution, that comprises any suitable concentration of peroxyformic acid. For example, the first reagent and the second reagent can be contacted with each other to form a liquid, e.g., a solution, that comprises any suitable concentration of peroxyformic acid. In some embodiments, the first reagent and the second reagent can be contacted with each other to form a liquid, e.g., a solution, that comprises from about 0.1 ppm to about 100,000 ppm of peroxyformic acid, from about 0.1 ppm to about 10,000 ppm of peroxyformic acid or from about 0.1 ppm to about 5,000 ppm of peroxyformic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm or greater of peroxyformic acid. In other embodiments, the first reagent and the second reagent can be contacted with each other to form a liquid, e.g., a solution, that comprises from about 1 ppm to about 500 ppm of peroxyformic acid, e.g., about 0.1-1 ppm, 0.1-10 ppm, 0.1-20 ppm, 0.1-30 ppm, 0.1-40 ppm, 0.1-50 ppm, 0.1-60 ppm, 0.1-70 ppm, 0.1-80 ppm, 0.1-90 ppm, 0.1-100 ppm, 0.1-150 ppm, 0.1-200 ppm, 0.1-250 ppm, 0.1-300 ppm, 0.1-350 ppm, 0.1-400 ppm, 0.1-450 ppm, 0.1-500 ppm of peroxyformic acid. In still other embodiments, the first reagent and the second reagent can be contacted with each other to form a liquid, e.g., a solution, that comprises from about 50 ppm to about 100 ppm of peroxyformic acid, e.g., about 50-60 ppm, 60-70 ppm, 70-80 ppm, 80-90 ppm or 90-100 ppm of peroxyformic acid. In yet other embodiments, the first reagent and the second reagent can be contacted with each other to form a liquid, e.g., a solution, that comprises from about 200 ppm to about 300 ppm of peroxyformic acid, e.g., about 200-210 ppm, 210-220 ppm, 220-230 ppm, 230-240 ppm, 240-250 ppm, 250-260 ppm, 260-270 ppm, 270-280 ppm, 280-290 ppm, 290-300 ppm of peroxyformic acid.

In another example, the solid composition can be contacted with a liquid to form a solution that comprises from about 0.1 ppm to about 100,000 ppm of peroxyformic acid, from about 0.1 ppm to about 10,000 ppm of peroxyformic acid or from about 0.1 ppm to about 5,000 ppm of peroxyformic acid. In some embodiments, the solid composition can be contacted with a liquid to form a liquid, e.g., a solution, that comprises from about 0.1 ppm to about 5,000 ppm of peroxyformic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm or greater of peroxyformic acid.

The present methods can be used to form a liquid, e.g., a solution, that comprises any suitable concentration of peroxyformic acid within any suitable time. For example, the first reagent and the second reagent in the present peroxyformic acid forming compositions can be contacted with each other to form a liquid, e.g., a solution, that comprises any suitable concentration of peroxyformic acid within any suitable time. In some embodiments, the first reagent and the second reagent can be contacted with each other to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm or greater, of peroxyformic acid within 1 minute of the contact time.

In another example, the solid composition can be contacted with a liquid to form a liquid, e.g., a solution, that comprises any suitable concentration of peroxyformic acid within any suitable time. In some embodiments, the solid composition can be contacted with a liquid to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm or greater, of peroxyformic acid within 1 minute of the contact time.

In an aspect, at least about 1 ppm peroxyformic is generated within less than 1 minute of contacting the first reagent and the second reagent. In an aspect, at least about 1 ppm peroxyformic is generated within less than about 55 seconds, 50 seconds or less, 45 seconds or less, 40 seconds or less, 35 seconds or less, 30 seconds or less, 25 seconds or less, 20 seconds or less, 15 seconds or less, 10 seconds or less, or 5 seconds or less. In an aspect, the reaction to form a liquid comprising at least about 1 ppm peroxyformic acid is near instantaneous.

In an aspect, at least about 100 ppm or at least about 500 ppm peroxyformic is generated within about 5 minutes or less of contacting the first reagent and the second reagent. In an aspect, at least about 100 ppm or 500 ppm peroxyformic is generated within less than about 4 minutes, 3 minutes or less, 2 minutes or less, or 1 minute or less.

The present methods can be used to form a liquid, e.g., a solution, that comprises any suitable percentage of the peak concentration of peroxyformic acid within any suitable time. For example, the first reagent and the second reagent can be contacted with each other to form a liquid, e.g., a solution, that comprises any suitable percentage of the peak concentration of peroxyformic acid within any suitable time. In some embodiments, the first reagent and the second reagent are contacted with each other to form a liquid, e.g., a solution, that comprises at least about 80% of the peak concentration of peroxyformic acid within from about 5 minutes to about 15 minutes of the contact time. For example, the first reagent and the second reagent are contacted with each other to form a liquid, e.g., a solution, that comprises at least about 80%, 85%, 90%, 95%, 96%, 97%, 98%, 99% or 100% of the peak concentration of peroxyformic acid within from about 5 minutes to about 15 minutes of the contact time. In another example, the first reagent and the second reagent are contacted with each other to form a liquid, e.g., a solution, that comprises at least about 80% of the peak concentration of peroxyformic acid within from about 5, 6, 7, 8, 9, 10, 11, 12, 13, 14 or 15 minutes of the contact time.

In another example, the solid composition can be contacted with a liquid to form a liquid, e.g., a solution, that comprises any suitable percentage of the peak concentration of peroxyformic acid within any suitable time. In some embodiments, the solid composition can be contacted with a liquid to form a liquid, e.g., a solution, that comprises at least about 80% of the peak concentration of peroxyformic acid within from about 5 minutes to about 15 minutes of the contact time. For example, the solid composition can be contacted with a liquid to form a liquid, e.g., a solution, that comprises at least about 80%, 85%, 90%, 95%, 96%, 97%, 98%, 99% or 100% of the peak concentration of peroxyformic acid within from about 5 minutes to about 15 minutes of the contact time. In another example, the solid composition can be contacted with a liquid to form a liquid, e.g., a solution, that comprises at least about 80% of the peak concentration of peroxyformic acid within from about 5, 6, 7, 8, 9, 10, 11, 12, 13, 14 or 15 minutes of the contact time.

The formed peroxyformic acid can maintain any suitable percentage of the peak concentration of peroxyformic acid within any suitable time. In some embodiments, the formed peroxyformic acid can maintain at least about 50% of the peak concentration from about 5 minutes to about 25 minutes after the contact between the first reagent and the second reagent or after the contact between the solid composition and a liquid. For example, the formed peroxyformic acid can maintain at least about 50%, 55%, 60%, 65%, 70%, 75%, 80%, 85%, 90%, 95%, 96%, 97%, 98%, 99% or 100% of the peak concentration from about 5 minutes to about 25 minutes after the contact between the first reagent and the second reagent or after the contact between the solid composition and a liquid. In another example, the formed peroxyformic acid can maintain at least about 50% of the peak concentration from about 5-25 minutes, e.g., about 5, 6, 7, 8, 9, 10, 11, 12, 13, 14, 15, 16, 17, 18, 19, 20, 21, 22, 23, 24 or 25 minutes, after the contact between the first reagent and the second reagent or after the contact between the solid composition and a liquid.

In some embodiments, the first reagent and the second reagent used in the present methods can be contacted with each other to form a solution that comprises at least about 80% of the peak concentration of peroxyformic acid within from about 1 minute to about 15 minutes of the contact time. In other embodiments, the formed peroxyformic acid maintains at least about 50% of the peak concentration from about 1 minute to about 15 minutes after the contact between the first reagent and the second reagent. In still other embodiments, the solid composition can be contacted with a liquid to form a solution that comprises at least about 80% of the peak concentration of peroxyformic acid within from about 1 minute to about 15 minutes of the contact time. In other embodiments, the formed peroxyformic acid maintains at least about 50% of the peak concentration from about 1 minute to about 15 minutes after the contact between the solid composition and the liquid.

In preferred aspects of the invention the desired peak concentration of peroxyformic acid is 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, 5,000 ppm, 6,000 ppm, 7,000 ppm, 8,000 ppm, 9,000 ppm, 10,000 ppm or more (inclusive of any ranges therein).

The present methods can further comprise forming a $C_2$-$C_{22}$ percarboxylic acid in a liquid, e.g., a solution. The $C_2$-$C_{22}$ percarboxylic acid can be any suitable $C_2$-$C_{22}$ percarboxylic acid. Exemplary $C_2$-$C_{22}$ percarboxylic acid includes peroxyacetic acid, peroxyoctanoic acid and/or peroxysulfonated oleic acid. In some embodiments, the $C_2$-$C_{22}$ percarboxylic acid is peroxyacetic acid.

The present methods can be used to generate peroxyformic acid in any suitable manner or at any suitable location. In some embodiments, the present methods can be used to generate peroxyformic acid in situ for the application of the formed peroxyformic acid.

In some embodiments, the present methods do not comprise using a perhyrolysis enzyme. For example, in some cases, the present methods do not comprise using a member of family 7 of the carbohydrate esterases (CE-7) or a perhyrolysis enzyme that is disclosed in U.S. patent application 2013/0289113.

In another aspect, the present invention is directed to peroxyformic acid formed using the present methods, e.g., peroxyformic acid formed in situ for the application of the formed peroxyformic acid.

The peroxyformic acid formed using the present methods (present composition) can further comprise additional percarboxylic acids. Various embodiments of the invention referring to peroxyformic acid compositions and/or peroxyformic acid solutions are further understood to optionally comprise additional percarboxylic acids. As used herein, the term "peracid" may also be referred to as a "percarboxylic acid" or "peroxyacid." Sulfoperoxycarboxylic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Patent Publication Nos. 2010/0021557, 2010/0048730 and 2012/0052134 which are incorporated herein by reference in their entireties. A peracid refers to an acid having the hydrogen of the hydroxyl group in carboxylic acid replaced by a hydroxy group. Oxidizing peracids may also be referred to herein as peroxycarboxylic acids.

In some embodiments, peroxyformic acid with other peroxycarboxylic acids can be generated by mixing an ester of a polyhydric alcohol with a composition comprising peroxycaboxylic acid(s) and hydrogen peroxide to form a composition that comprises both peroxyformic acid and other peroxycarboxylic acids. Examples of compositions comprising both peroxycarboxylic acid and hydrogen peroxide include peroxyacetic acid compositions, peroxyoctanoic acid compositions, etc., all are commercially available from Ecolab Inc. In use, an ester of a polyhydric alcohol can be contacted, e.g., mixed, with Oxonia Active, Tsunami 100, Matrixx, TurboOxysan and Octave, etc., to form a composition that comprises both peroxyformic acid and other desired peroxycarboxylic acids.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" includes a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like. The term "alkyl" or "alkyl groups" also refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or 'carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

In some embodiments, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —SO$_3$H, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

In some embodiments, aryl and heteroaryl groups can be unsubstituted or substituted on the ring by, for example, aryl, heteroaryl, alkyl, alkenyl, alkoxy, amino, carboxy, halo, nitro, cyano, —SO$_3$H, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Peracids suitable for use include any peroxycarboxylic acids, including varying lengths of peroxycarboxylic and percarboxylic acids (e.g. C1-22) that can be prepared from the reaction of an ester of a polyhydric alcohol and formic acid with hydrogen peroxide as described herein. Additional suitable peracids include those of acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid hydride, carboxylic acid anhydride, or sodium alcoholate. Alternatively, peracids can be prepared through non-equilibrium reactions, which may be generated for use in situ, such as the methods disclosed in U.S. Pat. Nos. 8,846,107 and 8,877,254 each titled "In Situ Generation of Peroxycarboxylic Acids at Alkaline pH, and Methods of Use Thereof," which are incorporated herein by reference. Preferably a composition of the invention includes peroxyformic acid, peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyformic acid and/or peroxyacetic acid. In another embodiment, a peroxycarboxylic acid has R that is an alkyl of 1-22 carbon atoms substituted with hydroxy. Methods of preparing peroxyacetic acid are known to those of skill in the art including those disclosed in U.S. Pat. No. 2,833,813, which is herein incorporated herein by reference.

In another embodiment, a sulfoperoxycarboxylic acid has the following formula:

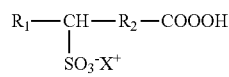

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In additional embodiments, a sulfoperoxycarboxylic acid is combined with a single or mixed peroxycarboxylic acid composition, such as a sulfoperoxycarboxylic acid with peroxyacetic acid and peroxyoctanoic acid (PSOA/POOA/POAA).

In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyformic acid, peroxyacetic acid and/or peroxyoctanoic acid. Other combinations of mixed peracids are well suited for use in the current invention.

Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example, peracetic acid (15%) available from Ecolab Inc. Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

Any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ percarboxylic acid comprises peroxyformic acid, peroxyacetic acid, peroxyoctanoic acid and/or peroxysulfonated oleic acid.

The $C_1$-$C_{22}$ percarboxylic acid can be used at any suitable concentration. In some embodiments, the $C_1$-$C_{22}$ percarboxylic acid has a concentration from about 1 wt-% to about 40 wt-%. In other embodiments, the $C_1$-$C_{22}$ percarboxylic acid has a concentration from about 1 wt-% to about 20 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. In yet other embodiments, the $C_1$-$C_{22}$ percarboxylic acid has a concentration from about 0.1 ppm to about 10,000 ppm, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-9,500 ppm, or 9,500-10,000 ppm.

Additional Optional Materials

The present compositions can optionally include additional ingredients to enhance the composition for treating various surfaces and targets according to the invention. Additional optional functional ingredients may include for example, peracid stabilizers, emulsifiers, corrosion inhibitors and/or descaling agents (i.e. scale inhibitors), surfactants and/or additional antimicrobial agents for enhanced efficacy (e.g. mixed peracids, biocides), antifoaming agents, anti-redeposition agents, bleaching agents, dispersants, solubility modifiers, wetting agents, metal protecting agents, sequestrants and/or chelating agents, fragrances and/or dyes, rheology modifiers, hydrotropes or couplers, buffers, solvents, acidulants and/or catalysts (e.g. strong mineral acids), additional carboxylic acids, and the like. In an embodiment, no additional functional ingredients are employed.

Friction Reducers

Friction reducers are used in water or other water-based fluids used in hydraulic fracturing treatments for subterranean well formations in order to improve permeability of the desired gas and/or oil being recovered from the fluid-conductive cracks or pathways created through the fracking process. The friction reducers allow the water to be pumped into the formations more quickly. Various polymer additives have been widely used as friction reducers to enhance or modify the characteristics of the aqueous fluids used in well drilling, recovery and production applications.

Examples of commonly used friction reducers include polyacrylamide polymers and copolymers. In an aspect, additional suitable friction reducers may include acrylamide-derived polymers and copolymers, such as polyacrylamide (sometime abbreviated as PAM), acrylamide-acrylate (acrylic acid) copolymers, acrylic acid-methacrylamide copolymers, partially hydrolyzed polyacrylamide copolymers (PHPA), partially hydrolyzed polymethacrylamide, acrylamide-methyl-propane sulfonate copolymers (AMPS) and the like. Various derivatives of such polymers and copolymers, e.g., quaternary amine salts, hydrolyzed versions, and the like, should be understood to be included with the polymers and copolymers described herein.

Friction reducers are combined with water and/or other aqueous fluids, which in combination are often referred to as "slick water" fluids. Slick water fluids have reduced frictional drag and beneficial flow characteristics which enable the pumping of the aqueous fluids into various gas- and/or oil-producing areas, including for example for fracturing.

In an aspect of the invention, a friction reducer is present in a use solution in an amount between about 1 ppm to 1,000 ppm, or from about 100 ppm to 1,000 ppm. In a further aspect, a friction reducer is present in a use solution in an amount of at least about 0.01 wt-% to about 10 wt-%, preferably at least about 0.01 wt-% to about 5 wt-%, preferably at least about 0.01 wt-% to about 1 wt-%, more preferably at least about 0.01 wt-% to about 0.5 wt-%, and still more preferably at least about 0.01 wt-% to about 0.1 wt-%. Beneficially, the compositions and methods of the invention do not negatively interfere with friction reducers included in an aqueous solution.

Viscosity Enhancers

Viscosity enhancers are additional polymers used in water or other water-based fluids used in hydraulic fracturing treatments to provide viscosity enhancement. Natural and/or synthetic viscosity-increasing polymers may be employed in compositions and methods according to the invention. Viscosity enhancers may also be referred to as gelling agents and examples include guar, xanthan, cellulose derivatives and polyacrylamide and polyacrylate polymers and copolymers, and the like.

In an aspect of the invention, a viscosity enhancer is present in a use solution in an amount between about 1 ppm to about 1,000 ppm, or from about 100 ppm to 1,000 ppm. In a further aspect, a viscosity enhancer is present in a use solution in an amount of at least about 0.01 wt-% to about 10 wt-%, preferably at least about 0.01 wt-% to about 5 wt-%, preferably at least about 0.01 wt-% to about 1 wt-%, at least about 0.01 wt-% to about 2 wt-%, preferably at least about 0.01 wt-% to about 1 wt-%, preferably at least about 0.01 wt-% to about 0.5 wt-%. Beneficially, the compositions and methods of the invention do not negatively interfere with viscosity enhancer included in an aqueous solution.

Corrosion Inhibitors

Corrosion inhibitors are additional molecules used in oil and gas recovery operations. Corrosion inhibitors that may be employed in the present disclosure include the exemplary corrosion inhibitors disclosed in U.S. Pat. Nos. 3,909,447, 4,443,609, 5,965,785 and 9,150,793, GB Pat. No. 1,198,734, WO/03/006581, WO04/044266, and WO08/005058, each incorporated herein by reference in their entireties.

In some embodiments, the corrosion inhibitor can be a phosphate ester, a derivative of the phosphate ester, a diacid, a derivative of the diacid, a quat amine, a derivative of the quat amine, an imidazoline, a derivative of the imidazoline, an alkyl pyridine, a derivative of the alkyl pyridine, a phosphonium salt, a derivative of the phosphonium salt, or a combination thereof.

In an embodiment, the corrosion inhibitors include neutralizing amines. Suitable neutralization amines include morpholine, methoxypropylamine, ethylenediamine, monoethanolamine, dimethylethanolamine diethylhydroxylamine, and hydrazine didrates.

In an embodiment, the corrosion inhibitors include cationic surfactant comprising an ammonium halide. The ammonium halide may include any suitable types of ammonium halides. In embodiments, the ammonium halides include alkyl ammonium halides, polyalkyl ammonium halides, benzyl triethyl ammonium halides or any combinations thereof. In embodiments, the cationic surfactant includes any combination or at least one of an alkyl trimethyl ammonium halide, alkyl triethyl ammonium halide, an alkyl dimethyl benzyl ammonium halide, and one or more imidazolinium halides.

In an embodiment, the corrosion inhibitors include phosphonates, including phosphonic acid and esters, such as tetrahydrothiazoles phosphonic acids or esters. Additional phosphorus-based compounds may be suitable for use, including thiophosphonic acid and the salts and alkyl, and aryl esters of the same.

In an aspect of the invention, a corrosion inhibitor is present in a use solution in an amount between about 1 ppm to 50,000 ppm. In a further aspect, a corrosion inhibitor is present in a use solution in an amount of at least about 0.0001 wt-% to about 10 wt-%, preferably at least about 0.0001 wt-% to about 5 wt-%, preferably at least about 0.0001 wt-% to about 1 wt-%, preferably at least about 0.0001 wt-% to about 0.1 wt-%, and still more preferably at least about 0.0001 wt-% to about 0.05 wt-%.

Beneficially, the compositions and methods of the invention do not negatively interfere with corrosion inhibitor included in an aqueous solution. As a further benefit, the use of the two-part peroxycarboxylic acid forming compositions according to the invention allow formulation of the corrosion inhibitors directly into either of the premix formulations, overcoming a substantial limitation of the prior art wherein conventional corrosion inhibitors are not sufficiently stable in other equilibrium chemistries. The two-part premixes according to embodiments of the invention allow formulation of the corrosion inhibitors directly into a premix and thereby reducing the number of inputs required for a system to be treated according to the methods and chemistries of the present invention.

Scale Inhibitors

Scale inhibitors are additional molecules used in oil and gas recovery operations. Common scale inhibitors that may be employed in these types of applications include polymers and co-polymers, phosphates, phosphate esters and the like.

In an aspect of the invention, a scale inhibitor is present in a use solution in an amount between about 1 ppm to about 5,000 ppm, or from about 100 ppm to 5,000 ppm. In a further aspect, a scale inhibitor is present in a use solution in an amount of at least about 0.0001 wt-% to about 10 wt-%, at least about 0.0001 wt-% to about 1 wt-%, preferably at least about 0.0001 wt-% to about 0.1 wt-%, preferably at least about 0.0001 wt-% to about 0.05 wt-%. Beneficially, the compositions and methods of the invention do not negatively interfere with scale inhibitor included in an aqueous solution.

Additional Antimicrobial Agents

Additional antimicrobial agents may be included in the compositions and/or methods of the invention for enhanced antimicrobial efficacy. In addition to the use of peracid compositions, additional antimicrobial agents and biocides may be employed. Additional biocides may include, for example, a quaternary ammonium compound as disclosed in U.S. Pat. No. 6,627,657, which is incorporated herein by reference in its entirety. Beneficially, the presence of the quaternary ammonium compound provides both synergistic antimicrobial efficacies with peracids, as well as maintains long term biocidal efficacy of the compositions.

In another embodiment, the additional biocide may include an oxidizer compatible phosphonium biocide, such as tributyl tetradecyl phosphonium chloride. The phosphonium biocide provides similar antimicrobial advantages as the quaternary ammonium compound in combination with the peracids. In addition, the phosphonium biocide is compatible with the anionic polymeric chemicals commonly used in the oil field applications, such as the methods of the fracking disclosed according to the invention.

Additional antimicrobial and biocide agents may be employed in amounts sufficient to provide antimicrobial efficacy, as may vary depending upon the water source in need of treatment and the contaminants therein. Such agents may be present in a use solution in an amount of at least about 0.1 wt-% to about 5 wt-% preferably at least about 0.1 wt-% to about 2 wt-%, more preferably from about 0.1 wt-% to about 1 wt-%.

Acidulants

Acidulants may be included as additional functional ingredients in a composition according to the invention. In an aspect, a strong mineral acid such as nitric acid or sulfuric acid can be used to treat water sources, as disclosed in U.S. Pat. No. 4,587,264, which is incorporated herein by reference in its entirety. The combined use of a strong mineral acid with the peracid composition provides enhanced antimicrobial efficacy as a result of the acidity assisting in removing chemical contaminants within the water source (e.g. sulfite and sulfide species). In addition, some strong mineral acids, such as nitric acid, provide a further benefit of reducing the risk of corrosion toward metals contacted by the peracid compositions according to the invention. In some embodiments, the present composition does not comprise a mineral acid or a strong mineral acid.

In an aspect, the acidulant is included in the second reagent with hydrogen peroxide. Any suitable acid can be included in the compositions as an acidulant. In an embodiment the acidulant is an acid or an aqueous acidic solution. In an embodiment, the acidulant includes an inorganic acid. In some embodiments, the acidulant is a strong mineral acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof.

Acidulants may be employed in amounts sufficient to provide the intended antimicrobial efficacy and/or anticorrosion benefits, as may vary depending upon the water source or surface in need of treatment and the contaminants therein. Such agents may be present in a use solution in an amount of at least about 0.1 wt-% to about 10 wt-%, preferably at least about 0.1 wt-% to about 5 wt-%, more preferably from about 0.1 wt-% to about 1 wt-%.

Catalase and Peroxidase Enzyme

In an aspect of the invention, a catalase or peroxidase enzyme can be used to reduce and/or eliminate the concentration of hydrogen peroxide in an antimicrobial peracid composition. The enzymes catalyze the decomposition of hydrogen peroxide to water and oxygen.

Various sources of catalase enzymes may be employed according to the invention, including: animal sources such as bovine catalase isolated from beef livers; fungal catalases isolated from fungi including *Penicillium chrysogenum*, *Penicillium notatum*, and *Aspergillus niger*, plant sources; bacterial sources such as *Staphylcoccus aureus*, and genetic variations and modifications thereof. In an aspect of the invention, fungal catalases are utilized to reduce the hydrogen peroxide content of a peracid composition. Catalases are commercially available in various forms, including liquid and spray dried forms. Commercially available catalase includes both the active enzyme as well as additional ingredients to enhance the stability of the enzyme. Some exemplary commercially available catalase enzymes include Genencor CA-100 and CA-400, as well as Mitsubishi Gas and Chemical (MGC) ASC super G and ASC super 200, and Optimase CA 400L from Genecor International. Additional description of suitable catalase enzymes are disclosed and herein incorporated by reference in its entirety from U.S. Patent Publication No. 2009/0269324.

In an aspect of the invention, catalase enzymes have a high ability to decompose hydrogen peroxide. Beneficially, the reduction or elimination of hydrogen peroxide from oxidizing compositions obviates the various detriments caused by oxidizing agents. In particular, the use of catalase with the peracids compositions provides enhanced antimicrobial benefits without causing the damage associated with conventional oxidizing agents (e.g. peracetic acid, hypochlorite or hypochlorous acid, and/or chlorine dioxide), such as corrosion.

Peroxidase enzymes may also be employed to decompose hydrogen peroxide from a peracid composition. Although peroxidase enzymes primarily function to enable oxidation of substrates by hydrogen peroxide, they are also suitable for effectively lowering hydrogen peroxide to peracid ratios in compositions. Various sources of peroxidase enzymes may be employed according to the invention, including for example animal sources, fungal peroxidases, and genetic variations and modifications thereof. Peroxidases are commercially available in various forms, including liquid and spray dried forms. Commercially available peroxidases include both the active enzyme as well as additional ingredients to enhance the stability of the enzyme.

In some embodiments, the catalase or peroxidase enzyme is able to degrade at least about 50% of the initial concentration of hydrogen peroxide in a peracid composition. Preferably, the enzyme is provided in sufficient amount to reduce the hydrogen peroxide concentration of a peracid composition by at least more than about 50%, more preferably at least about 60%, at least about 70%, at least about 80%, at least about 90%. In some embodiments, the enzyme reduces the hydrogen peroxide concentration of a peracid composition by more than 90%.

In an aspect of the invention, the enzymes are suitable for use and have a tolerance to a wide range of temperatures, including the temperatures ranges in water treatment applications which may range from about 0-80° C. A suitable catalase enzyme will maintain at least 50% of its activity under such storage and/or application temperatures for at least about 10 minutes, preferably for at least about 1 hour.

In an aspect of the invention, a catalase or peroxidase enzyme is present in a use solution of the peracid composition in sufficient amounts to reduce the concentration of hydrogen peroxide from the peracid composition by at least 50% within about 10 minutes, preferably within about 5 minutes, preferably within about 2 to 5 minutes, more preferably within about 1 minute. The ranges of concentration of the enzymes will vary depending upon the amount of time within which 50% of the hydrogen peroxide from the peracid composition is removed. In certain aspects of the invention, a catalase or peroxidase enzyme is present in a use solution composition including the water source to be treated in amounts between about 1 ppm and about 1,000 ppm, preferably between about 5 ppm and 500 ppm, and more preferably between about 10 ppm and about 100 ppm.

Wetting Agents

In an aspect, a wetting agent is present in a use solution of the peracid composition in sufficient amounts. Wetting agents function to increase the surface contact or penetration activity of the peroformic acid composition of the invention. Wetting agents which can be used in the composition of the invention include any of those constituents known within the art to raise the surface activity of the composition of the invention. In an exemplary aspect, the wetting agent is a sulfonic acid or salt thereof (e.g., dodecylbenzene sulfonic acid, sodium salt). In certain embodiments, the wetting agent is present in amounts from about 0.001 to about 10 wt-% wetting agent, about 0.01 to about 1 wt-% wetting agent, about 0.01 to about 0.5 wt-% wetting agent, or about 0.1 to about 0.5 wt-% wetting agent.

Stabilizing Agents

In an aspect, the peroxyformic acid compositions can further comprise a stabilizing agent for the peroxyformic acid and/or a stabilizing agent for hydrogen peroxide. In an aspect, the peroxyformic acid forming compositions can further comprise peroxide, and/or a pH buffering agent. The present peroxyformic acid forming compositions can comprise any suitable pH buffering agent stabilizing agent. Exemplary stabilizing agents include a phosphonate salt(s) and/or a heterocyclic dicarboxylic acid, e.g., dipicolinic acid. In some embodiments, the stabilizing agent is pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts. In other embodiments, the present peroxycarboxylic acid forming compositions comprise two or more stabilizing agents, e.g., HEDP and 2,6-pyridinedicarboxylic acid (DPA). In an aspect the stabilizing agent(s) can be comprised in any suitable part of the present peroxyformic acid forming compositions. In some embodiments, the first reagent comprises a stabilizing agent for the peroxyformic acid and/or a pH buffering agent. In other embodiments, the second reagent comprises a stabilizing agent for hydrogen peroxide. In still other embodiments, the present peroxyformic acid forming compositions can further comprise a third reagent that comprises a stabilizing agent for the peroxyformic acid, a stabilizing agent for hydrogen peroxide, and/or a pH buffering agent. In yet other embodiments, the solid composition comprises a stabilizing agent for peroxyformic acid, a stabilizing agent for hydrogen peroxide, and/or a pH buffering agent.

In an aspect, the peroxyformic acid forming compositions can further comprise any suitable pH buffering agent. The pH buffer reagent can include any reagent that is compatible with the ester(s) in the peroxyformic acid forming compositions. Exemplary buffer agents suitable for using with a liquid ester can be an organic amine, such as triethanol amine, imidazole, etc. Exemplary buffer agents suitable for using with a solid form of ester include a broader range of buffers, such as a carbonate salt, a phosphate salt, etc. The pH buffer reagent can be comprised in any suitable part of the present peroxyformic acid forming compositions. In some embodiments, the first reagent comprises a pH buffering agent. In other embodiments, the peroxyformic acid forming compositions can further comprise a third reagent that comprises a pH buffering agent. In still other embodiments, the solid composition comprises a pH buffering agent.

In an aspect, the peroxyformic acid forming compositions can further comprise any suitable stabilizing agent for hydrogen peroxide. Exemplary stabilizing agents for hydrogen peroxide include phosphonates, heterocyclic carboxylic acids and the mixtures thereof. In some embodiments, stabilizing agents for hydrogen peroxide can be Dequest 2010, Dequest 2066, Dipicolinic acids, etc. The stabilizing agent for hydrogen peroxide can be comprised in any suitable part of the peroxyformic acid forming compositions. In some embodiments, the second reagent comprises a stabilizing agent for hydrogen peroxide. In other embodiments, the peroxyformic acid forming compositions can further comprise a third reagent that comprises a stabilizing agent for hydrogen peroxide. In still other embodiments, the solid composition comprises a stabilizing agent for hydrogen peroxide.

Alkalinity Source

The peroxyformic acid forming compositions may require pH adjustment with an alkalinity source. In an exemplary aspect, in the event a reagent of the self-indicating peracid chemistry includes an acidic component, such as a wetting agent, an alkalinity source may be desirable to increase the strongly acidic pH to ensure the perhydrolysis reaction to generate the peroxyformic acid is not slowed.

Suitable sources of alkalinity can include, but is not limited to, an alkaline metal hydroxide, an alkaline earth metal hydroxide, an alkali metal silicate, an alkali metal carbonate, borates, amines, amides or other basic nitrogen sources and mixtures thereof. Suitable alkaline metal hydroxides include, but are not limited to, sodium hydroxide, potassium hydroxide and mixtures thereof. Suitable alkaline earth metal hydroxides include, but are not limited to, magnesium hydroxide, calcium hydroxide and mixtures and derivatives thereof. Suitable alkali metal silicates include but are not limited to, sodium silicate and derivatives thereof. Suitable amines include, but are not limited to, primary, secondary or tertiary amines and diamines carrying at least one nitrogen linked hydrocarbon group, which represents a saturated or unsaturated linear or branched alkyl group having at least 1 carbon atom. Amines may further include alkanolamines including, for example, monoethanolamine, monoisopropanolamine, diethanolamine, diisopropanolamine, triethanolamine, triisopropanolamine and the like.

Surfactants

In some aspects of the invention, the peroxyformic acid compositions or one of the reagents employed in forming the peroxyformic acid include at least one surfactant. Surfactants are preferably included to increase solubility of the peroxyformic acid or to maintain the pH of the composition. According to an embodiment of the invention, the surfactant is a hydrotrope coupler or solubilizer, which can be used to ensure that the composition remains phase stable and in a single highly active aqueous form. Such hydrotrope solubilizers or couplers can be used at concentrations that maintain phase stability but do not result in unwanted compositional interaction. Surfactants particularly suitable for use with the compositions of the present invention include, but are not limited to, nonionic surfactants, anionic surfactants, amphoteric surfactants and zwitterionic surfactants. Preferably, nonionic and/or anionic surfactants are employed with the peracid compositions of the invention. Exemplary surfactants that can be used are commercially available from a number of sources. For a discussion of surfactants, see Kirk-Othmer, Encyclopedia of Chemical Technology, Third Edition, volume 8, pages 900-912.

Peracids are known to be strong oxidation agents, and as a result many chemicals, including commonly used surfactants are not compatible with concentrated peracids for extended presence of peracids. While it is ideal to use surfactants along with peracids to deliver preferred performance, such as cleaning, wetting et al., there is very limited choice of surfactants that could be put in preformed peracid formulations that meet the minimum shelf life requirements for commercial use. For examples, nonionic surfactants will be degraded by peracids, and cationic surfactants with halogen counter anions will decompose peracids. Some anionic surfactants, namely non substituted alkyl sulfonates, such as linear alkylbenzensulfonate, liner alkylsulfonate are more compatible with peracids and maybe used in some peracids compositions, but these anionic surfactants may not deliver the desired performance owing to their unwanted properties, such as high foam, water hardness tolerance as well as regulation requirements. In contrast, for onsite generated peracid compositions such as disclosed in the present art, all surfactants described above could be coexist with the peracids, as the generated peracids are only stored for very limited time, and typically in hours at the most, and the reactions between the surfactants and the peracids are not significant.

According to a preferred embodiment of the invention, the surfactant is an acidic anionic surfactant. According to a further embodiment, the surfactant is an antimicrobial agent. Exemplary surfactant, hydrotrope solubilizers include anionic surfactants such as an alkyl sulfate, an aryl sulfonate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

In some embodiments, the compositions of the present invention includes from about 1 wt-% to about 80 wt-% of a surfactant. In other embodiments the compositions of the present invention include from about 1 wt-% to about 50 wt-% of a surfactant. In additional embodiments, the compositions of the present invention include from about 1 wt-% to about 10 wt-% of a surfactant. In further embodiments, the compositions of the present invention or a use solution of the peroxyformic acid composition include about 10 ppm to about 10,000 ppm of a surfactant. In further embodiments, the compositions of the present invention or a use solution of the peroxyformic acid composition include about 10 ppm to about 100 ppm of a surfactant. It is to be understood that all ranges and values between these ranges and values are encompassed by the present invention.

Nonionic Surfactants

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates; and capped alcohol alkoxylates, such as Plurafac LF221; mixtures thereof or the like.

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

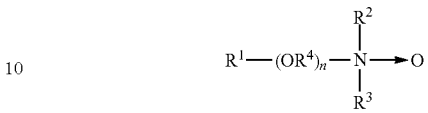

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl)amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl)glucamine sulfates, and sulfates of alkylpolysaccharides such as the sulfates of alkylpolyglucoside, and the like. Also included are the alkyl sulfates, alkyl poly(ethyleneoxy)ether sulfates and aromatic poly(ethyleneoxy)sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula: R—O—(CH$_2$CH$_2$O)$_n$(CH$_2$)$_m$—CO$_2$X in which R is a C$_8$ to C$_{22}$ alkyl group or

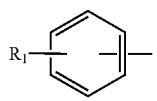

in which $R_1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

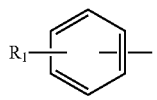

and $R_1$ is a $C_6$-$C_{12}$ alkyl group. In still yet other embodiments, $R_1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphate, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Exemplary suitable amphoteric surfactants include long chain imidazole derivatives, including carboxymethylated compounds (glycinates) which are frequently are called betaines. Betaines are a special class of amphoteric discussed herein below in the section entitled, Zwitterion Surfactants. These and other amphoteric surfactants are further described in U.S. patent application Ser. No. 12/568,493, entitled "Sulfoperoxycarboxylic Acids, Their Preparation and Methods of Use as Bleaching and Antimicrobial Agents," hereby expressly incorporated herein in its entirety by reference.

Long chain imidazole derivatives having application in the present invention generally have the general formula:

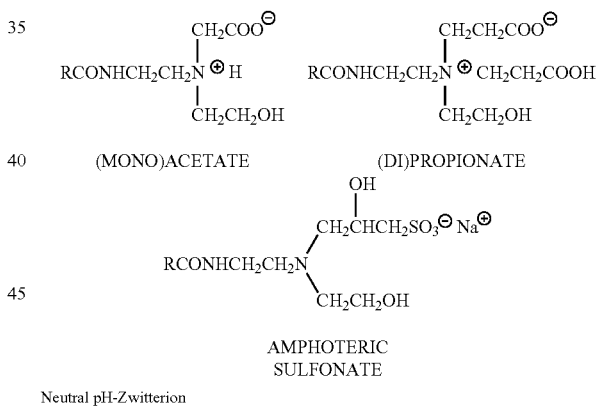

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Additionally suitable amphoteric surfactants include long chain N-alkylamino acids which are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl)alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—N+$(CH_2$—$CH_2$—$CO_2Na)_2$—$CH_2$—$CH_2$—OH or $C_{12}$-alkyl-C(O)—N(H)—$CH_2$—$CH_2$—N+$(CH_2$—$CO_2Na)_2$—$CH_2$—$CH_2$—OH. Disodium cocoampho dipropionate is one suitable amphoteric surfactant and is commercially available under the tradename Miranol™ FBS from Rhodia Inc. (Cranbury, N.J). Another suitable coconut derived amphoteric surfactant with the chemical name disodium cocoampho diacetate is sold under the tradename Mirataine™ JCHA, also from Rhodia Inc.

A typical listing of amphoteric classes, and species of these surfactants, is given in U.S. Pat. No. 3,929,678 issued to Laughlin and Heuring on Dec. 30, 1975 and further examples are given in "Surface Active Agents and Detergents" (Vol. I and II by Schwartz, Perry and Berch), each of which are hereby expressly incorporated herein in its entirety by reference.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

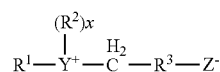

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S [N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

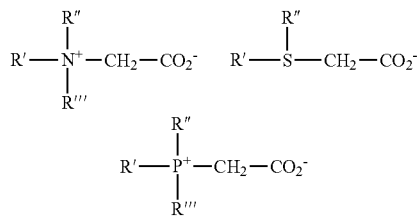

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N+R^2SO^{3-}$, in which R is a $C_6-C_{18}$ hydrocarbyl group, each $R^1$ is typically a $C_1-C_3$ alkyl, e.g. methyl, and $R^2$ is a $C_1-C_6$ hydrocarbyl group, e.g. a $C_1-C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated in their entirety.

Self-Indicating Chemistries

In an aspect, various self-indicating chemistries are suitable for use with the peroxyformic acid chemistries according to the invention. In an aspect, the self-indicating chemistry compositions comprise a combination of at least two dyes. In a further aspect, the self-indicating chemistry compositions comprise a combination of three dyes. In a further aspect, the combination of dyes provides a visual indication system suitable for detecting the formation or generation of a peroxycarboxylic acid formed in a perhydrolysis reaction. Preferably, the combination of dyes provides a visual indication system using three distinct colors (e.g. blue, green, yellow). In an aspect, the combination of dyes provides a non-fluorescent visual indicator for the peroxycarboxylic acid compositions.

Suitable dyes for use in the self-indicating chemistry composition include oxidize able dyes, including those insensitive to hydrogen peroxide driving a perhydrolysis reaction to generation a peroxycarboxylic acid composition. In an aspect, the self-indicating chemistry composition include a combination of dyes having different half-lives in order to provide sustained visual indicators, such as for up to 7 days, or from 1 to 7 days, or from 12 hours to 7 days. In an aspect, the self-indicating chemistry composition include a combination of HRP substrates and synthetic dyes. Suitable chemistries are disclosed in U.S. Ser. No. 62/216,435, which is herein incorporated by reference in its entirety.

Methods for Treating a Target

In still another aspect, the present invention is directed to a method for treating a surface or a target, which method comprises contacting a surface or a target with an effective amount of peroxyformic acid formed using the above methods to form a treated surface or target composition, wherein said treated surface or target composition comprises from about 0.1 ppm to about 10,000 ppm of said peroxyformic acid, and said contacting step lasts for sufficient time to stabilize or reduce microbial population in and/or on said surface or target or said treated surface of target composition.

In some embodiments, the composition used in the present methods is an equilibrated composition that comprises peroxyformic acid, hydrogen peroxide, formic acid and a solvent, e.g., water. In some embodiments, the composition used in the present methods does not comprise a mineral acid, e.g., the mineral acids disclosed in WO 91/07375.

The peroxyformic acid and the surface or target can be contacted to form a treated target composition comprising any suitable concentration of said peroxyformic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-9,500 ppm, or 9,500-10,000 ppm of peroxyformic acid.

The composition used in the present methods can retain any suitable concentration or percentage of the peroxyformic acid activity for any suitable time after the treated surface or target composition is formed. In some embodiments, the present composition retains at least about 50%, 55%, 60%, 65%, 70%, 75%, 80%, 85% or 90% of the initial peroxyformic acid activity for any suitable time after the treated surface or target composition is formed. In other embodiments, the present composition retains at least about 60% of the initial peroxyformic acid activity for at least 1, 2, 3, 4, 5, 6, 7, 8, 9, 10, 11, 12, 13, 14, 15, 20, 25, 30 minutes, 1, 2, 5, 10, 15, 20 or 24 hours, or longer after the treated target composition is formed.

In some embodiments, the target to be treated by the present methods can be a food item or a plant item and/or at least a portion of a medium, a container, an equipment, a system or a facility for growing, holding, processing, packaging, storing, transporting, preparing, cooking or serving the food item or the plant item. Any suitable concentration of peroxyformic acid can be used in the present methods. For example, the peroxyformic acid can be used at a concentration from about 1 ppm to about 100 ppm, e.g., about 1-2 ppm, 2-3 ppm, 3-4 ppm, 4-5 ppm, 5-6 ppm, 6-7 ppm, 7-8 ppm, 8-9 ppm, 9-10 ppm, 10-15 ppm, 15-20 ppm, 20-25 ppm, or 25-30 ppm, 30-40 ppm, 40-50 ppm, 50-60 ppm, 60-70 ppm, 70-80 ppm, 80-90 ppm, 90-100 ppm of peroxyformic acid. In some embodiments, the target is a food item or a plant item and the contacting step minimizes or does not induce an organoleptic effect in and/or on the food item or a plant item.

The present methods can be used for treating any suitable plant item. In some embodiments, the plant item is a grain, fruit, vegetable or flower plant item. In other embodiments, the plant item is a living plant item or a harvested plant item. In still other embodiments, the plant item comprises a seed, a tuber, a growing plant, a cutting, or a root stock. In yet other embodiments, the present methods are used for treating a living plant tissue comprising treating the plant tissue with the above composition in a diluted concentration to stabilize or reduce microbial population in and/or on the plant tissue. In yet other embodiments, the present methods are used for growing a plant on a hydroponic substrate in a hydroponic liquid supply medium, comprising: (a) establishing a growing and living plant tissue in the hydroponic substrate; (b) contacting the living plant tissue, the hydroponic substrate and the hydroponic liquid with a composition of the present invention to stabilize or reduce microbial population in and/or on the living plant tissue; and (c) harvesting a usable plant product with reduced microbial contamination.

The present methods can be used for treating any suitable food item. For example, the food item can be an animal product, e.g., an animal carcass or an egg, a fruit item, a vegetable item, or a grain item. In some embodiments, the animal carcass can be a beef, pork, veal, buffalo, lamb, fish, sea food or poultry carcass. In other embodiments, the sea food carcass can be scallop, shrimp, crab, octopus, mussel, squid or lobster. In still other embodiments, the fruit item can be a botanic fruit, a culinary fruit, a simple fruit, an aggregate fruit, a multiple fruit, a berry, an accessory fruit or a seedless fruit. In yet other embodiments, the vegetable item can be a flower bud, a seed, a leaf, a leaf sheath, a bud, a stem, a stem of leaves, a stem shoot, a tuber, a whole-plant sprout, a root or a bulb. In yet other embodiments, the grain item can be maize, rice, wheat, barley, sorghum, millet, oat, triticale, rye, buckwheat, fonio or quinoa.

In some embodiments, the target to be treated by the present methods can be a medium, a surface, a container, an equipment, or a system in a health care facility, e.g., a physical office or a hospital. Any suitable concentration of peroxyformic acid can be used in the present methods. For example, the peroxyformic acid can be used at a concentration from about 10 ppm to about 300 ppm, e.g., 10-15 ppm, 15-20 ppm, 20-25 ppm, or 25-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, or 250-300 ppm of peroxyformic acid.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods can be used for treating a target that is at least a portion of a solid surface or liquid media. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

The peroxyformic acid can be applied in any suitable manner. In some embodiments, the peroxyformic acid can be applied to a target by means of a spray, a fog, or a foam, or by dipping all or part of the target in a composition comprising the peroxyformic acid. In some embodiments, the peroxyformic acid composition is applied to the target by means of a spray, a fog, or a foam. In other embodiments, the diluted peroxyformic acid is applied to the target by applying in the form of a thickened or gelled solution. In still other embodiments, all or part of the target is dipped in the peroxyformic acid composition. The target and/or the peroxyformic acid composition can be subject to any suitable movement to help or facilitate the contact between the target and the peroxyformic acid composition. In some embodiments, the peroxyformic acid composition can be agitated. In other embodiments, the peroxyformic acid composition can be sprayed onto a target, e.g., an animal carcass, under suitable pressure and at a suitable temperature. For example, the peroxyformic acid composition can be sprayed onto an animal carcass at a pressure of at least 50 psi at a temperature of up to about 60° C., resulting in a contact time of at least 30 seconds.

The present methods can comprise any suitable, additional steps. In some embodiments, the present methods can comprise a vacuum treatment step. In other embodiments, the present methods can comprise a step of applying an activated light source to the target, e.g., an animal carcass.

The contacting step in the present methods can last for any suitable amount of time. In some embodiments, the contacting step can last for at least about 10 seconds. For example, the contacting step can last for at least about 10, 20, 30, 40, 50 seconds, 1 minute, 1-2 minutes, 2-3 minutes, 3-4 minutes, 4-5 minutes, 5-6 minutes, 6-7 minutes, 7-8 minutes, 8-9 minutes, or 9-10 minutes, 10-15 minutes, 15-20 minutes, 20-25 minutes, 25-30 minutes, 30-40 minutes, 40-50 minutes, 50-65 minutes, 1-2 hours, 2-3 hours, 3-4 hours, 4-5 hours, 5-6 hours, 6-7 hours, 7-8 hours, 8-9 hours, or 9-10 hours, 16 hours, 1 day, 3 days, 1 week, or longer. In an aspect, the contacting occurs for a period of time before degradation of the peroxyformic acid composition.

The present methods can be used to reduce microbial population in and/or on the target or the treated target composition by any suitable magnitude. In some embodiments, the present methods can be used to reduce microbial population in and/or on the target or the treated target composition by at least one $\log_{10}$, two $\log_{10}$, three $\log_{10}$, four $\log_{10}$, five $\log_{10}$, or more. In other embodiments, the level of a microorganism, if present in and/or on the target or the treated target composition, can be stabilized or reduced by the present methods. For example, at least 10%, 10%, 20%, 30%, 40%, 50%, 60%, 70%, 80%, or 90% or more of the microorganism, if present in and/or on the target or the treated target composition, can be killed, destroyed, removed and/or inactivated by the present methods.

The present methods can be used to reduce population of any suitable microbe(s) in and/or on the target or the treated target composition by any suitable magnitude. In some embodiments, the present methods can be used to reduce a prokaryotic microbial population, e.g., a bacterial or an archaeal population. In other embodiments, the present methods can be used to reduce a eukaryotic microbial population, e.g., a protozoal or fungal population. In still other embodiments, the present methods can be used to reduce a viral population. Exemplary viral population can comprise a population of a DNA virus, a RNA virus, and a reverse transcribing virus.

The present methods can be used to stabilize or reduce a microbial population in and/or on the target or the treated target composition, wherein the target is a food item or a plant item and the contacting step minimizes or does not induce an organoleptic effect in and/or on the food item or a plant item. Typical organoleptic properties include the aspects of food or other substances as experienced by the senses, including taste, sight, smell, and touch, in cases where dryness, moisture, and stale-fresh factors are to be considered. See e.g., Jasper Womach, the Congressional Research Service document "Report for Congress: Agriculture: A Glossary of Term, Programs, and Laws, 2005 Edition." In some embodiments, organoleptic procedures are performed as part of the meat and poultry inspections to detect signs of disease or contamination. In other embodiments, organoleptic tests are conducted to determine if package materials and components can transfer tastes and odors to the food or pharmaceutical products that they are packaged in. Shelf life studies often use taste, sight, and smell (in addition to food chemistry and toxicology tests) to determine whether a food product is suitable for consumption. In still other embodiments, organoleptic tests are conducted as part of the Hurdle technology. Typically, Hurdle technology refers to an intelligent combination of hurdles which secures the microbial safety and stability as well as the organoleptic and nutritional quality and the economic viability of food products. See generally, Leistner L (1995) "In Gould G W (Ed.) *New Methods of Food Preservation*, Springer, pp. 1-21; and Leistner I (2000) "*International Journal of Food Microbiology*, 55:181-186.

The present methods can be conducted at any suitable temperature range. In some embodiments, the present methods can be conducted at a temperature ranging from about 0° C. to about 70° C., e.g., about 0° C.-1° C., 1° C.-2° C., 2° C.-3° C., 3° C.-4° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., 55° C.-60° C., 60° C.-65° C., or 65° C.-70° C. In other embodiments, the present methods can be conducted at a temperature at or lower than 0° C.

In some embodiments, the present methods can comprise adding a peroxidase or a catalase to further reduce the hydrogen peroxide level in and/or on the target or the treated target composition. The peroxidase or catalase can be added in any suitable manner. In some embodiments, the peroxidase or catalase can be added to the target or the treated target composition before a composition used in the present methods is provided to the target. In other embodiments, the present compositions can be diluted into a suitable intermediate volume, and the peroxidase or catalase can be added to the diluted, intermediate volume. Thereafter, the diluted, intermediate volume, which contains the peroxidase or catalase, can be added to target. Any suitable peroxidase or catalase, including the ones described below, can be used in the present methods.

Use in Water Treatment

The present methods can be used to treat any suitable surface or target. In some embodiments, the target is water, and the present methods can comprise providing an effective amount of peroxyformic acid formed using the above methods to a water source in need of treatment to form a treated water source, wherein said treated water source comprises from about 1 ppm to about 1,000 ppm of said peroxyformic acid, e.g., about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm of peroxyformic acid.

The present methods can be used to treat any suitable water source. For example, a water source in need of treatment can be fresh water, pond water, sea water, produced water, paper manufacturing water, tower water or a combination thereof.

In some embodiments, the tower water is cooling water and the treated water source comprises from about 1 ppm to about 10 ppm of the peroxyformic acid, e.g., about 1-2 ppm, 2-3 ppm, 3-4 ppm, 4-5 ppm, 5-6 ppm, 6-7 ppm, 7-8 ppm, 8-9 ppm, or 9-10 ppm peroxyformic acid. The contacting step can last any suitable amount of time, e.g., about 1-2 minutes, 2-3 minutes, 3-4 minutes, 4-5 minutes, 5-6 minutes, 6-7 minutes, 7-8 minutes, 8-9 minutes, or 9-10 minutes. The contacting step can be conducted at suitable temperature range. For example, the contacting step can be conducted at a temperature ranging from about 0° C. to about 60° C., e.g., about 0° C.-1° C., 1° C.-2° C., 2° C.-3° C., 3° C.-4° C., 4° C.-5° C., 5° C.- 10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C.

In some embodiments, the present methods can be used to treat a water source used in oil or gas drilling operation. For example, the present methods can be used to treat a water source used in an operation of induced hydraulic fracturing (hydrofracturing or fracking). The water source can comprise a friction reducer or a viscosity enhancer. The present methods can be used to treat a water source to form a treated water source that comprises from about 1 ppm to about 10 ppm of the peroxyformic acid, e.g., about 1-2 ppm, 2-3 ppm, 3-4 ppm, 4-5 ppm, 5-6 ppm, 6-7 ppm, 7-8 ppm, 8-9 ppm, or 9-10 ppm peroxyformic acid. The present methods can further comprise disposing of the treated water source. The present methods can further comprise directing the treated water source into a subterranean environment, e.g., a subterranean environment that comprises a well in a gas and/or oil. In some embodiments, the target water to be treated contains iron sulfide and/or H2S, and the present methods can be used to oxidize iron sulfide and/or reduce or eliminate H2S in the target water. In other embodiments, the target water to be treated needs to be clarified, e.g., containing particles, and the present methods can be used to clarify the target water.

In some embodiments, the target to be treated by the present methods can be water and/or at least a portion of a medium, a container, an equipment, a system or a facility for producing, holding, processing, packaging, storing, or transporting pulp. The present methods can be used to treat water and/or other target(s) for any suitable purpose. For example, the present methods can be used in papermaking, textiles, food, or pharmaceutical industry. The present methods can be used to treat a water source, alone or in combination with other target(s), to form a treated water source that comprises any suitable concentration of peroxyformic acid, e.g., about 1-2 ppm, 2-3 ppm, 3-4 ppm, 4-5 ppm, 5-6 ppm, 6-7 ppm, 7-8 ppm, 8-9 ppm, 9-10 ppm, 10-15 ppm, 15-20 ppm, 20-25 ppm, or 25-30 ppm of peroxyformic acid.

The peroxyformic acid compositions can be used for a variety of industrial applications, e.g., to reduce microbial or viral populations on a surface or object or in a body or stream of water. In some aspects, the invention includes methods of using the peroxyformic acid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, peroxyformic acid and catalase compositions are used to control the growth of microorganisms in water used in various oil and gas operations. In a further aspect, the compositions are suitable for incorporating into fracturing fluids to control or eliminate microorganisms.

As used herein for the methods of the invention, the peroxyformic acid compositions can employ a variety of peroxyformic acid compositions having a low to substantially no hydrogen peroxide concentration. These peroxyformic acid compositions include peroxyformic acid compositions with a catalase or peroxidase enzyme to reduce the hydrogen peroxide to peracid ratio and/or other reduced hydrogen peroxide peroxyformic acid compositions disclosed herein. In a preferred embodiment peroxyformic acid and catalase use solutions having reduced or substantially no hydrogen peroxide are introduced to a water source in need of treatment.

The methods by which the peroxyformic acid solutions are introduced into the aqueous fluids according to the invention are not critical. Introduction of the peroxyformic acid compositions may be carried out in a continuous or intermittent manner and will depend on the type of water being treated. In some embodiments, the peroxyformic acid compositions are introduced into an aqueous fluid according to the methods disclosed in U.S. patent application Ser. No.

13/645,671, titled "New Method and Arrangement for Feeding Chemicals into a Hydrofracturing Process and Oil and Gas Applications", which is hereby incorporated by reference in its entirety.

In some embodiments, the water source treated by the present methods does not comprise reuse water, the treated water source comprises from about 10 ppm to about 20 ppm of the in situ formed peroxyformic acid and from about 1 ppm to about 2 ppm of hydrogen peroxide and the treated water source does not comprise a friction reducer and/or a rheology modifier.

In some embodiments, the water source treated by the present methods is a blended water source that comprises about 80 wt-% fresh water or pond water and about 20 wt-% of reuse water, the treated water source comprises from about 25 ppm to about 35 ppm of the in situ formed peroxyformic acid and from about 2 ppm to about 3 ppm of hydrogen peroxide and catalase, the treated water source does not comprise a friction reducer and/or a rheology modifier, and the treated water source is formed before reaching a blending tub.

In some embodiments, the water source treated by the present methods is a blended water source that comprises about 80 wt-% fresh water or pond water and about 20 wt-% of reuse water, the treated water source comprises from about 25 ppm to about 35 ppm of the in situ formed peroxyformic acid and from about 2 ppm to about 3 ppm of hydrogen peroxide and catalase, the treated water source comprises a friction reducer and/or a rheology modifier, and the treated water source is formed in a blending tub.

In some embodiments, the treated water source comprises from about 30 ppm or less of the in situ formed peroxyformic acid and about 0.5 ppm or less of the hydrogen peroxide, the treated water source comprises a friction reducer and/or a rheology modifier, and the treated water source is directed into or is at a subterranean environment.

In some aspects, the methods disclosed for water treatment in oil and gas recovery provide effective antimicrobial efficacy without deleterious interaction with functional agents, including for example friction reducers. In a further aspect, the methods for water treatment provide increased antimicrobial efficacy compared to the use of the antimicrobial peracids alone. In a still further aspect, the methods of use result in the disposal of cleaner water with low numbers of microorganisms. In yet a further aspect of the methods of the invention, the reduction and/or elimination of $H_2O_2$ from the peracid compositions minimizes the negative effects of the oxidant $H_2O_2$. Still further, the methods of the invention reduce the volume expansion within sealed systems used in oil and gas recovery methods, as a result of the reduction and/or elimination of $H_2O_2$ from the systems.

In an aspect, the peroxyformic acid solutions are added to waters in need of treatment prior to the drilling and fracking steps in order to restrict the introduction of microbes into the reservoir and to prevent the microbes from having a negative effect on the integrity of the fluids. The treatment of source waters (e.g. pond, lake, municipal, etc.) and/or produced waters is particularly well suited for use according to the invention.

The treated waters according to the invention can be used for both slick water fracturing (i.e. using frictions reducers) and/or gel fracturing (i.e. using viscosity enhancers), depending on the type of formation being fractured and the type of hydrocarbon expected to be produced. Use of a peroxyformic acid solution, including a catalase treated peroxyformic acid composition use solution having low to substantially no hydrogen peroxide, is suitable for both slick water fracturing and gel fracturing.

In an aspect, pretreating the peroxyformic acid composition with catalase substantially removes the hydrogen peroxide with minimal to no impact on the fracturing fluids and the well itself. In an aspect, the peroxyformic acid composition pretreated with catalase allows the formation of gel suitable for gel fracturing, as opposed to untreated peroxyformic acid composition solutions that do not allow a gel to form under certain conditions. In a further aspect, the peroxyformic acid composition solutions are added to waters in need of treatment in the subterranean well formations (e.g. introduced through a bore hole in a subterranean formation). These methods provide additional control within the well formation suitable for reducing microbial populations already present within the down hole tubing in the well or within the reservoir itself.

In a still further aspect, the peroxyformic acid composition solutions are added to waters in need of treatment before disposal. In such an aspect, flow back waters (e.g. post fracking) are treated to minimize microbial contaminations in the waters and to remove solids prior to disposal of the water into a subterranean well, reuse in a subsequent fracturing application or return of the water into local environmental water sources.

In an aspect, the water source in need of treatment may vary significantly. For example, the water source may be a freshwater source (e.g. pond water), salt water or brine source, brackish water source, recycled water source, or the like. In an aspect, wherein offshore well drilling operations are involved, seawater sources are often employed (e.g. saltwater or non-saltwater). Beneficially, the peroxyformic acid compositions, with or without catalase, of the invention are suitable for use with any types of water and provide effective antimicrobial efficiency with any of such water sources.

Large volumes of water are employed according to the invention as required in well fluid operations. As a result, in an aspect of the invention, recycled water sources (e.g. produced waters) are often employed to reduce the amount of a freshwater, pond water or seawater source required. Recycled or produced water are understood to include non-potable water sources. The use of such produced waters (in combination with freshwater, pond water or seawater) reduces certain economic and/or environmental constraints. In an aspect of the invention, thousands to millions of gallons of water may be employed and the combination of produced water with fresh water sources provides significant economic and environmental advantages. In an aspect of the invention, as much produced water as practical is employed. In an embodiment at least 1% produced water is employed, preferably at least 5% produced water is employed, preferably at least 10% produced water is employed, preferably at least 20% produced water is employed, or more preferably more than 20% produced water is employed.

In an aspect of the invention, the method includes a pretreatment step, wherein the peroxyformic acid composition is treated with a catalase enzyme to reduce the hydrogen peroxide concentration in a use solution. The pretreatment step occurs prior to combining the peracid antimicrobial composition and/or catalase to a water source in need of treatment. In an aspect of the invention, the pretreatment may occur within a few minutes to hours before addition to a water source.

According to embodiments of the invention, a sufficient amount of the peroxyformic acid composition, with or without catalase, is added to the aqueous water source in need of treatment to provide the desired peroxyformic acid concentration for antimicrobial efficacy. For example, a water source is dosed amounts of the peroxyformic acid and catalase use solution composition until a peroxyformic acid concentration within the water source is detected within the preferred concentration range (e.g. about 1 ppm to about 100 ppm peracid). In an aspect, it is preferred to have a microbial count of less than about 100,000 microbes/mL, more preferably less than about 10,000 microbes/mL, or more preferably less than about 1,000 microbes/mL.

The methods of use as described herein can vary in the temperature and pH conditions associated with use of the aqueous treatment fluids. For example, the aqueous treatment fluids may be subjected to varying ambient temperatures according to the applications of use disclosed herein, including ranging from about 0° C. to about 130° C. in the course of the treatment operations. Preferably, the temperature range is between about 5° C. to about 100° C., more preferably between about 10° C. to about 80° C. However, as a majority of the antimicrobial activity of the compositions of the invention occurs over a short period of time, the exposure of the compositions to relatively high temperatures is not a substantial concern. In addition, the peracid composition aqueous treatment fluids (i.e. use solutions) may be subjected to varying pH ranges, such as from 1 to about 10.5. Preferably, the pH range is less than about 9, less than about 7.2 (pKa value of performic acid) to ensure the effective antimicrobial efficacy of the peracid.

The antimicrobial compositions of the invention are fast-acting. However, the present methods require a certain minimal contact time of the compositions with the water in need of treatment for occurrence of sufficient antimicrobial effect. The contact time can vary with concentration of the use compositions, method of applying the use compositions, temperature of the use compositions, pH of the use compositions, amount of water to be treated, amount of soil or substrates in the water to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. The contact time will further vary based upon the concentration of peracid in a use solution.

Beneficial Effects of the Methods of Use in Water Treatment

In an aspect, the methods of use provide an antimicrobial for use that does not negatively impact the environment. Beneficially, the degradation of the compositions of the invention provides a "green" alternative.

In a further aspect, the methods of use provide an antimicrobial for use that does not negatively interfere with friction reducers, viscosity enhancers and/or other functional ingredients. In a further aspect, the methods of use do not negatively interfere with any additional functional agents utilized in the water treatment methods, including for example, corrosion inhibitors, descaling agents and the like. The compositions administered according to the invention provide extremely effective control of microorganisms without adversely affecting the functional properties of any additive polymers of an aqueous system. In addition, the peroxyformic acid compositions provide additional benefits to a system, including for example, reducing corrosion within the system due to the decreased or substantially eliminated hydrogen peroxide from a treated composition. Beneficially, the non-deleterious effects of the peroxyformic acid compositions (with or without a catalase) on the various functional ingredients used in water treatment methods are achieved regardless of the make-up of the water source in need of treatment.

In an additional aspect, the methods of use prevent the contamination of systems, such as well or reservoir souring. In further aspects, the methods of use prevent microbiologically-influenced corrosion of the systems upon which it is employed.

In further aspects, the methods of use employ the antimicrobial and/or bleaching activity of the peroxyformic acid compositions. For example, the invention includes a method for reducing a microbial population and/or a method for bleaching. These methods can operate on an article, surface, in a body or stream of water or a gas, or the like, by contacting the article, surface, body, or stream with the compositions. Contacting can include any of numerous methods for applying the compositions, including, but not limited to, providing the antimicrobial peroxyformic acid compositions in an aqueous use solution and immersing any articles, and/or providing to a water source in need of treatment.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms associated with oil- and gas-field operations.

Exemplary microorganisms susceptible to the peracid compositions of the invention include, gram positive bacteria (e.g., *Staphylococcus aureus, Bacillus* species (sp.) like *Bacillus subtilis, Clostridia* sp.), gram negative bacteria (e.g., *Escherichia coli, Pseudomonas* sp., *Klebsiella pneumoniae, Legionella pneumophila, Enterobacter* sp., *Serratia* sp., *Desulfovibrio* sp., and *Desulfotomaculum* sp.), yeasts (e.g., *Saccharomyces cerevisiae* and *Candida albicans*), molds (e.g., *Aspergillus niger, Cephalosporium acremonium, Penicillium notatum*, and *Aureobasidium pullulans*), filamentous fungi (e.g., *Aspergillus niger* and *Cladosporium resinae*), algae (e.g., *Chlorella vulgaris, Euglena gracilis*, and *Selenastrum capricornutum*), and other analogous microorganisms and unicellular organisms (e.g., phytoplankton and protozoa). Other exemplary microorganisms susceptible to the peracid compositions of the invention include the exemplary microorganisms disclosed in U.S. patent application US 2010/0160449 A1, e.g., the sulfur- or sulfate-reducing bacteria, such as *Desulfovibrio* and *Desulfotomaculum* species.

Use in Other Treatments

Additional embodiments of the invention include water treatments for various industrial processes for treating liquid systems. As used herein, "liquid system" refers to flood waters or an environment within at least one artificial artifact, containing a substantial amount of liquid that is capable of undergoing biological fouling. Liquid systems include but are not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In a further aspect, the present methods can also be used to treat other liquid systems where both the compositions' antimicrobial function and oxidant properties can be utilized. Aside from the microbial issues surrounding waste water, waste water is often rich in malodorous compounds of reduced sulfur, nitrogen or phosphorous. A strong oxidant such as the compositions disclosed herein converts these compounds efficiently to their odor free derivatives e.g. the sulfates, phosphates and amine oxides. These same properties are very useful in the pulp and paper industry where the property of bleaching is also of great utility.

The present methods can be conducted at any suitable temperature. In some embodiments, the present methods are conducted at a temperature ranging from about −2° C. to about 70° C., e.g., from about 0° C. to about 4° C. or 5° C., from about 5° C. to about 10° C., from about 11° C. to about 20° C., from about 21° C. to about 30° C., from about 31° C. to about 40° C., including at about 37° C., from about 41° C. to about 50° C., from about 51° C. to about 60° C., or from about 61° C. to about 70° C.

The present methods can be used in the methods, processes or procedures described and/or claimed in U.S. Pat. Nos. 5,200,189, 5,314,687 and 5,718,910. In some embodiments, the present methods can be used of sanitizing facilities or equipment comprises the steps of contacting the facilities or equipment with the composition of the present invention at a temperature in the range of about 4° C. to about 60° C. The peroxyformic acid composition is then circulated or left in contact with the facilities or equipment for a time sufficient to sanitize (generally at least 30 seconds) and the treated target composition is thereafter drained or removed from the facilities or equipment.

As noted above, the present methods are useful in the cleaning or sanitizing of processing facilities or equipment in the food service, food processing or health care industries. Examples of process facilities in which the present methods can be employed include a milk line dairy, a continuous brewing system, food processing lines such as pumpable food systems and beverage lines, etc. Food service wares can also be disinfected with the present methods. The present methods are also useful in sanitizing or disinfecting solid surfaces such as floors, counters, furniture, medical tools and equipment, etc., found in the health care industry. Such surfaces often become contaminated with liquid body spills such as blood, other hazardous body fluids or mixtures thereof.

Generally, the actual cleaning of the in-place system or other surface (i.e., removal of unwanted offal therein) can be accomplished with a different material such as a formulated detergent which is introduced with heated water. After this cleaning step, the peroxyformic acid composition can be applied or introduced into the system at a use solution concentration in unheated, ambient temperature water. In some embodiments, the peroxyformic acid composition is found to remain in solution in cold (e.g., 40° F./4° C.) water and heated (e.g., 140° F./60° C.) water. Although it is not normally necessary to heat the aqueous use solution of the peroxyformic acid composition, under some circumstances heating may be desirable to further enhance its antimicrobial activity.

In some embodiments, a method of sanitizing substantially fixed in-place process facilities comprises the following steps. The peroxyformic acid composition of the present invention is introduced into the process facilities at a temperature in the range of about 4° C. to about 60° C. After introduction of the use solution, the solution is circulated throughout the system for a time sufficient to sanitize the process facilities (i.e., to kill undesirable microorganisms). After the system has been sanitized by means of the present composition, the use composition or solution is drained from the system. Upon completion of the sanitizing step, the system optionally may be rinsed with other materials such as potable water. The present composition is preferably circulated through the process facilities for 10 minutes or less.

In other embodiments, the present peroxyformic acid composition may also be employed by dipping food processing equipment into the diluted (or use) composition or solution of the present invention, soaking the equipment for a time sufficient to sanitize the equipment, and wiping or draining excess solution off the equipment. The composition may be further employed by spraying or wiping food processing surfaces with the use solution, keeping the surfaces wet for a time sufficient to sanitize the surfaces, and removing the excess composition or solution by wiping, draining vertically, vacuuming, etc.

In still other embodiments, the present peroxyformic acid composition may also be used in a method of sanitizing hard surfaces such as institutional type equipment, utensils, dishes, health care equipment or tools, and other hard surfaces. The present peroxyformic acid composition may also be employed in sanitizing clothing items or fabric which has become contaminated. The peroxyformic acid composition is contacted with any of the above contaminated surfaces or items at use temperatures in the range of about 4° C. to about 60° C. for a period of time effective to sanitize, disinfect, or sterilize the surface or item.

The present methods can be used in the methods, processes or procedures described and/or claimed in U.S. Pat. Nos. 6,165,483 and 6,238,685B1, to treat field or greenhouse grown plant tissue, seeds, fruits, and growing media and containers. The present peroxyformic acid composition can lower the natural, plant pathogen and human pathogenic microbial load resulting in less waste to molding, spoilage, and destruction because of pathogenic poisons.

In some embodiments, the present peroxyformic acid composition can be used to protect growing plant tissue from the undesirable effects of microbial attack. The present peroxyformic acid composition can be applied to growing plant tissues and can provide residual antimicrobial effects after the plant has completed its growth cycle, fruit or vegetable material have been harvested and sent to market. The present composition can be an effective treatment of living or growing plant tissues including seeds, roots, tubers, seedlings, cuttings, rooting stock, growing plants, produce, fruits and vegetables, etc. Under certain circumstances, a single peroxyacid material can be effective, however, in other circumstances, a mixed peroxy acid has substantially improved and surprising properties.

In some embodiments, the composition used in the present methods also may contain a hydrotrope for the purpose of increasing the aqueous solubility of various slightly soluble organic compounds. The preferred embodiment of the composition utilizes a hydrotrope chosen from the group of n-octanesulfonate, a xylene sulfonate, a naphthalene sulfonate, ethylhexyl sulfate, lauryl sulfate, an amine oxide, or a mixture thereof.

In some embodiments, the composition used in the present methods may also contain a chelating agent for the purpose of removing ions from solution. The preferred embodiment of the invention uses 1-hydroxyethylidene-1, 1-diphosphonic acid.

The present methods can be used in the methods, processes or procedures described and/or claimed in U.S. Pat. Nos. 6,010,729, 6,103,286, 6,545,047 and 8,030,351 for sanitizing animal carcasses.

In some embodiments, the compositions of the present invention can be used in a method of treating animal carcasses to obtain a reduction by at least one $\log_{10}$ in surface microbial population which method includes the step of treating said carcass with a composition of the present invention comprising an effective antimicrobial amount comprising at least 2 parts per million (ppm, parts by weight per each one million parts) of one or more peroxycarboxylic acids having up to 12 carbon atoms, an effective antimicrobial amount comprising at least 20 ppm of one or more carboxylic acids having up to 18 carbon atoms, and the first and second stabilizing agents described above, to reduce the microbial population.

In yet other embodiments, the present invention is directed to a method of treating an animal carcass to reduce a microbial population in resulting cut meat, the method comprising the steps of spraying an aqueous antimicrobial treatment composition onto said carcass at a pressure of at least 50 psi at a temperature of up to about 60° C. resulting in a contact time of at least 30 seconds, the antimicrobial composition comprising an effective antimicrobial amount comprising least 2 ppm of one or more carboxylic acid, peroxycarboxylic acid or mixtures thereof and the first and second stabilizing agents described above; and achieving at least a one $\log_{10}$ reduction in the microbial population.

In yet other embodiments, the present invention is directed to a method of treating an animal carcass to reduce a microbial population in resulting cut meat, the method comprising the steps of placing the animal carcass in a chamber at atmospheric pressure; filling the chamber with condensing steam comprising an antimicrobial composition, e.g., a diluted composition of the present invention, for a short duration; and quickly venting and cooling the chamber to prevent browning of the meat carcass; wherein the duration of the steam thermal process may be from about 5 seconds to about 30 seconds and the chamber temperature may reach from about 50° C. to about 93° C.

The antimicrobial composition can be applied in various ways to obtain intimate contact with each potential place of microbial contamination. For example, it can be sprayed on the carcasses, or the carcasses can be immersed in the composition. Additional methods include applying a foamed composition and a thickened or gelled composition. Vacuum and or light treatments can be included, if desired, with the application of the antimicrobial composition. Thermal treatment can also be applied, either pre-, concurrent with or post application of the antimicrobial composition.

One preferred spray method for treating carcasses with diluted compositions of the present invention involves spraying the carcass with an aqueous spray at a temperature less than about 60° C. at a pressure of about 50 to 500 psi gauge wherein the spray comprises an effective antimicrobial amount of a carboxylic acid, an effective antimicrobial amount of a peroxycarboxylic acid or mixtures thereof, and the first and second stabilizing agents described above. These sprays can also contain an effective portion of a peroxy compound such as hydrogen peroxide and other ingredients such as sequestering agents, etc. The high pressure spray action of the aqueous treatment can remove microbial populations by combining the mechanical action of the spray with the chemical action of the antimicrobial materials to result in an improved reduction of such populations on the surface of the carcass.

All pressures are psig (or psi gauge). In some embodiments, differentiation of antimicrobial "-cidal" or "-static" activity, the definitions which describe the degree of efficacy, and the official laboratory protocols for measuring this efficacy are important considerations for understanding the relevance of antimicrobial agents in compositions. Antimicrobial compositions may affect two kinds of microbial cell damages. The first is a truly lethal, irreversible action resulting in complete microbial cell destruction or incapacitation. The second type of cell damage is reversible, such that if the organism is rendered free of the agent, it can again multiply. The former is termed bacteriocidal and the latter, bacteriostatic. A sanitizer and a disinfectant are, by definition, agents which provide antibacterial or bacteriocidal activity and may achieve at least a five-fold reduction (i.e., a five log 10 reduction) in microbial populations after a 30 second contact time (see AOAC method 960.09).

The present methods can be used in the methods, processes or procedures described and/or claimed in U.S. Pat. Nos. 8,017,409 and 8,236,573. In some embodiments, the present methods may be used for a variety of domestic or industrial applications, e.g., to reduce microbial or viral populations on a surface or object or in a body or stream of water. The peroxyformic acid compositions of the present invention may be applied in a variety of areas including kitchens, bathrooms, factories, hospitals, dental offices and food plants, and may be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces may be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces may be made from a variety of materials including, for example, paper, fiber, woven or non-woven fabric, soft plastics and elastomers. The diluted (or use) compositions may also be applied to soft surfaces such as food and skin (e.g., a hand). The diluted (or use) compositions may be employed as a foaming or non-foaming environmental sanitizer or disinfectant.

In other embodiments, the peroxyformic acid compositions of the present invention may be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

In still other embodiments, the peroxyformic acid compositions of the present invention may also be used in veterinary products such as mammalian skin treatments or in products for sanitizing or disinfecting animal enclosures, pens, watering stations, and veterinary treatment areas such as inspection tables and operation rooms. The peroxyformic acid compositions may be employed in an antimicrobial foot bath for livestock or people.

In yet other embodiments, the present methods may be employed for reducing the population of pathogenic microorganisms, such as pathogens of humans, animals, and the like. Exemplary pathogenic microorganisms include fungi, molds, bacteria, spores, and viruses, for example, *S. aureus, E. coli, Streptococci, Legionella, Pseudomonas aeruginosa*, mycobacteria, tuberculosis, phages, or the like. Such pathogens may cause varieties of diseases and disorders, including Mastitis or other mammalian milking diseases, tuberculosis, and the like. The present methods may be used to reduce the population of microorganisms on skin or other external or mucosal surfaces of an animal. In addition, the present methods may be used to kill pathogenic microorganisms that spread through transfer by water, air, or a surface substrate. In some applications, the compositions of the present invention need only be applied to the skin, other external or mucosal surfaces of an animal water, air, or surface.

In yet other embodiments, the present methods may also be used on foods and plant species to reduce surface microbial populations; used at manufacturing or processing sites handling such foods and plant species; or used to treat process waters around such sites. For example, the present methods may be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The present methods may be used to treat transport waters such as those found in flumes, pipe transports, cutters, slicers, blanchers, retort systems, washers, and the like. Particular foodstuffs that may be treated with the present methods include eggs, meats, seeds, leaves, fruits and vegetables. Particular plant surfaces include both harvested and growing leaves, roots, seeds, skins or shells, stems, stalks, tubers, corms, fruit, and the like. The present methods may also be used to treat animal carcasses to reduce both pathogenic and non-pathogenic microbial levels.

In yet other embodiments, the present methods may be useful in the cleaning or sanitizing of containers, processing facilities, or equipment in the food service or food processing industries. The present methods may be used on food packaging materials and equipment, including for cold or hot aseptic packaging. Examples of process facilities in which the present methods may be employed include a milk line dairy, a continuous brewing system, food processing lines such as pumpable food systems and beverage lines, etc. Food service wares may be disinfected with the present methods. For example, the present methods may also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

In yet other embodiments, the present methods may also be used on or in other industrial equipment and in other industrial process streams such as heaters, cooling towers, boilers, retort waters, rinse waters, aseptic packaging wash waters, and the like. The present methods may be used to treat microbes and odors in recreational waters such as in pools, spas, recreational flumes and water slides, fountains, and the like.

In yet other embodiments, a filter containing the peroxyformic acid compositions of the present invention may be used to reduce the population of microorganisms in air and liquids. Such a filter may be used to remove water and air-born pathogens such as *Legionella*.

In yet other embodiments, the present methods may be employed for reducing the population of microbes, fruit flies, or other insect larva on a drain or other surface.

In yet other embodiments, the present methods may also be employed by dipping food processing equipment into the peroxyformic acid composition or solution of the present invention, soaking the equipment for a time sufficient to sanitize the equipment, and wiping or draining excess composition or solution off the equipment. The present methods may be further employed by spraying or wiping food processing surfaces with the peroxyformic acid composition or solution, keeping the surfaces wet for a time sufficient to sanitize the surfaces, and removing excess composition or solution by wiping, draining vertically, vacuuming, etc.

In yet other embodiments, the present methods may also be used for sanitizing hard surfaces such as institutional type equipment, utensils, dishes, health care equipment or tools, and other hard surfaces. The present methods may also be employed in sanitizing clothing items or fabrics which have become contaminated. The peroxyformic acid compositions of the present invention can be contacted with any contaminated surfaces or items at use temperatures in the range of about 4° C. to 60° C., for a period of time effective to sanitize, disinfect, or sterilize the surface or item. For example, the peroxyformic acid compositions may be injected into the wash or rinse water of a laundry machine and contacted with contaminated fabric for a time sufficient to sanitize the fabric. Excess composition may be removed by rinsing or centrifuging the fabric.

In yet other embodiments, the peroxyformic acid compositions of the present invention may be applied to microbes or to soiled or cleaned surfaces using a variety of methods. These methods may operate on an object, surface, in a body or stream of water or a gas, or the like, by contacting the object, surface, body, or stream with the diluted (or use) composition. Contacting may include any of numerous methods for applying a composition, such as spraying the composition, immersing the object in the composition, foam or gel treating the object with the composition, or a combination thereof.

In yet other embodiments, the peroxyformic acid compositions of the present invention may be employed for bleaching pulp. The compositions may be employed for waste treatment. Such a composition may include added bleaching agent.

In yet other embodiments, other hard surface cleaning applications for the peroxyformic acid compositions of the present invention include clean-in-place systems (CIP), clean-out-of-place systems (COP), washer-decontaminators, sterilizers, textile laundry machines, ultra and nano-filtration systems and indoor air filters. COP systems may include readily accessible systems including wash tanks, soaking vessels, mop buckets, holding tanks, scrub sinks, vehicle parts washers, non-continuous batch washers and systems, and the like.

The concentrations of peroxyformic acid and/or hydrogen peroxide in the peroxyformic acid compositions of the present invention can be monitored in any suitable manner. In some embodiments, the concentrations of peroxyformic acid and/or hydrogen peroxide in the peroxyformic acid and/or hydrogen peroxide compositions can be monitored using a kinetic assay procedure, e.g., the exemplary procedure disclosed in U.S. Pat. Nos. 8,017,409 and 8,236,573. This can be accomplished by exploiting the difference in reaction rates between peroxyformic acid and hydrogen peroxide when using, for example, a buffered iodide reagent to differentiate peroxyformic acid and hydrogen peroxide concentrations when both these analyte compounds are present in the use composition. The monitor may also determine the concentrations of peroxyformic acid and/or hydrogen peroxide in the presence of other additional ingredients, such as acidulants, one or more stabilizing agents, nonionic surfactants, semi-polar nonionic surfactants, anionic surfactants, amphoteric or ampholytic surfactants, adjuvants, solvents, additional antimicrobial agents or other ingredients which may be present in the use composition.

Methods for Treating a Biofilm

In yet another aspect, the present invention is directed to a method for treating a biofilm, which method comprises contacting a biofilm on a surface with an effective amount of peroxyformic acid for a sufficient time to stabilize, reduce and/or remove microbial population in and/or on said treated biofilm, or to stabilize, reduce and/or remove said biofilm on said surface.

The present methods can be used to treat a biofilm in any suitable location or environment. In some embodiments, the present methods can be used to treat a biofilm located on or inside a human environment, such as a biofilm located on or inside a shower room or site, a water pipe, a sewage pipe, a floor, a counter, or a part of human body. For example, the present methods can be used to treat a biofilm located on or inside a dental plaque, a part of a urinary tract, a part of a middle ear, or a part of gums. In other embodiments, the present methods can be used to treat a biofilm located on or inside a cooling- or heating-water system. In still other embodiments, the present methods can be used to treat a biofilm located on or inside an engineering system, e.g., a pipeline of oil and gas industry. In still other embodiments, the present methods can be used to treat a biofilm located on or inside a vehicle, e.g., an automobile, a boat or a ship. In yet other embodiments, the present methods can be used to treat a biofilm located on or inside a plant. In yet other embodiments, the present methods can be used to treat a biofilm located on or inside a consumer product, e.g., a contact lens or a pair glasses. In yet other embodiments, the present methods can be used to treat a biofilm located on or inside a medical device, e.g., an implantable medical device. Exemplary implantable medical devices include a catheter, a prosthetic cardiac valve or an intrauterine device. In yet other embodiments, the present methods can be used to treat a biofilm located on or inside a membrane, e.g., an ultrafiltration membrane (UF) membrane.

The present methods can use any suitable concentration of peroxyformic acid. In some embodiments, the present methods can comprise contacting a biofilm on a surface with from about 10 ppm to about 1,000 ppm peroxyformic acid, e.g., 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, or 950-1,000 ppm peroxyformic acid.

The present methods can comprise contacting a biofilm on a surface with an effective amount of peroxyformic acid for any suitable amount of time. In some embodiments, the present methods can comprise contacting a biofilm on a surface with an effective amount of peroxyformic acid for from about 1 minute to about 10 hours, e.g., about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In an aspect, the contacting occurs for a period of time before degradation of the peroxyformic acid composition.

The present methods can be used to treat a biofilm made of or from any suitable microbial population. In some embodiments, the present method can be used to treat a biofilm made of or from a prokaryotic microbial population, e.g., a bacterial or an archaeal population. Exemplary bacterial populations include a population of *Pseudomonas aeruginosa, Streptococcus mutans, Streptococcus pneumoniae*, a *Legionella* bacteria, or a *Bacillus* bacteria, e.g., *Bacillus* sp. Spore. In other embodiments, the present method can be used to treat a biofilm made of or from an eukaryotic microbial population, e.g., a protozoal or fungal population. In still other embodiments, the present method can be used to treat a biofilm made of or from a viral population.

The peroxyformic acid used in the present methods can be prepared using any suitable methods as disclosed herein according to the invention. In an embodiment, the peroxyformic acid used in the present methods can be prepared by contacting an ester of a polyhydric alcohol and formic acid, with hydrogen peroxide or a substance that generates hydrogen peroxide when in contact with a liquid. For example, the peroxyformic acid used in the present methods can be prepared using any of the peroxyformic acid forming compositions described above or any of the methods described above. In other embodiments, the peroxyformic acid used in the present methods can be prepared in situ for the application of the formed peroxyformic acid.

In some embodiments, the present methods can further comprise contacting the biofilm with a $C_2$-$C_{22}$ percarboxylic acid. Exemplary $C_2$-$C_{22}$ percarboxylic acids include peroxyacetic acid, peroxyoctanoic acid and/or peroxysulfonated oleic acid. In other embodiments, the present methods can further comprise contacting the biofilm with a surfactant. Exemplary surfactants include an anionic surfactant, a nonionic surfactant, a cationic surfactant as well as an amphoteric surfactant. In still other embodiments, the present methods can further comprise contacting the biofilm with a solvent. Exemplary solvents include an alcohol, an ester, a glycol ether, an amide, a hydrocarbon etc. In still other embodiments, the present methods can further comprise contacting the biofilm with an enzyme.

In some embodiments, the present methods can further comprise assessing the efficacy of the method for treating a biofilm. The efficacy of the present methods can be assessed using any suitable methods. For example, the efficacy of the present methods can be assessed using a biofilm reactor. Exemplary biofilm reactors include a Center for Disease Control (CDC) biofilm reactor or a Rotating Disk Reactor (RDR) biofilm reactor. The biofilm reactor can comprise a surface or disc coupon, e.g., a polycarbonate coupon.

Methods for High Level Disinfecting, e.g. Endoscope and Other Instrument Reprocessing In yet another aspect, the various methods for treatment using the peroxyformic acid generated according to the methods of the invention can be employed for high level disinfectant applications, including sterilizing medical devices. The rate of formation of the peroxyformic acid in situ is particularly beneficial for the application of use for high level disinfection. The disinfectant is generated in situ and provides on demand disinfectant. Beneficially, the methods employing the high level disinfectant do not require high pressure and temperature required to achieve sterility. In an embodiment, the surface, such as an instrument, in need of treatment is contacted with an effective amount of peroxyformic acid for a sufficient time to stabilize, reduce and/or remove microbial population in and/or on said treated surface, or to stabilize, reduce and/or remove soils and microbes on said surface.

In an aspect, the methods allow for repurposing or reuse of the surface through disinfection and/or sanitizing of the surface, such as an instrument. Exemplary surfaces, including instruments suitable for reprocessing according to the invention include any instrument, including medical or dental instruments or devices that can benefit from cleaning with a composition according to the present invention. Particularly suitable instruments include, but are not limited to: diagnostic instruments, scopes (e.g., endoscopes, stethoscopes, and arthoscopes) and related equipment, and the like, or combinations thereof. Various conventional reprocessing methods which are suitable for use with the peroxyformic acid generated in situ are disclosed in U.S. Pat. Nos. 4,721,123 and 5,310,524, each of which are incorporated herein by reference in their entirety.

The present methods can use any suitable concentration of peroxyformic acid. In some embodiments, the present methods can comprise contacting a surface with from about 10 ppm to about 1,000 ppm peroxyformic acid, e.g., 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, or 950-1,000 ppm peroxyformic acid. In a preferred aspect, the methods of contacting provide from about 10 ppm to about 500 ppm peroxyformic acid for high level disinfectant generated in situ within a matter of minutes.

The present methods can comprise contacting a surface with an effective amount of peroxyformic acid for any suitable amount of time. In some embodiments, the present methods can comprise contacting a surface with an effective amount of peroxyformic acid for from about 1 minute to about an hour, e.g., about 1 minute, 2 minutes, 3 minutes, 4 minutes, 5 minutes, 6 minutes, 7 minutes, 8 minutes, 9 minutes, or 10 minutes or greater. In an aspect, the contacting time is preferably less than 10 minutes, and more preferably less than 5 minutes. In an aspect, the contacting occurs for a period of time before degradation of the peroxyformic acid composition.

The present methods can be used to treat a surface for instrument reprocessing having a contaminated surface from any suitable microbial populations. In some embodiments, the present method can be used to treat a surface made of or from a prokaryotic microbial population, e.g., a bacterial or an archaeal population. Exemplary bacterial populations include a population of Pseudomonas aeruginosa, Streptococcus mutans, Streptococcus pneumoniae, a Legionella bacteria, or a Bacillus bacteria, e.g., Bacillus sp. Spore. In other embodiments, the present method can be used to treat a surface made of or from an eukaryotic microbial population, e.g., a protozoal or fungal population. In still other embodiments, the present method can be used to treat a surface made of or from a viral population.

The peroxyformic acid used in the present methods can be prepared using any suitable methods disclosed herein. In some embodiments, the peroxyformic acid used in the present methods can be prepared by contacting an ester of a polyhydric alcohol and formic acid, with hydrogen peroxide or a substance that generates hydrogen peroxide when in contact with a liquid. For example, the peroxyformic acid used in the present methods can be prepared using any of the peroxyformic acid forming compositions described above or any of the methods described above. In other embodiments, the peroxyformic acid used in the present methods can be prepared in situ for the application of the formed peroxyformic acid.

In some embodiments, the present methods can further comprise contacting the surface with the peroxyformic acid and a $C_2$-$C_{22}$ percarboxylic acid. Exemplary $C_2$-$C_{22}$ percarboxylic acids include peroxyacetic acid, peroxyoctanoic acid and/or peroxysulfonated oleic acid. In other embodiments, the present methods can further comprise contacting the surface with a surfactant. Exemplary surfactants include an anionic surfactant, a nonionic surfactant, a cationic surfactant as well as an amphoteric surfactant. In still other embodiments, the present methods can further comprise contacting the surface with a solvent. Exemplary solvents include an alcohol, an ester, a glycol ether, an amide, a hydrocarbon etc. In still other embodiments, the present methods can further comprise contacting the surface with an enzyme.

The present methods can be conducted at any suitable temperature range. In some embodiments, the present methods can be conducted at a temperature ranging from about 20° C. to about 40° C., e.g., about 20° C.-25° C., 25° C.-30° C., 30° C.-35° C., or 35° C.-40° C., or ambient conditions.

The present methods are preferably conducted at a near neutral pH of the peroxyformic acid compositions to avoid corrosion of the treated surfaces. In some embodiments, the pH is from about 4-9, 4.5-5.5, and preferably 5.5-6.5. In a preferred aspect, the methods are conducted at near neutral pH and thereby reduces and/or eliminates risk of corrosion to the surfaces being treated.

Beneficially, the methods of high level disinfection are suitable for in situ generation of the peroxyformic acid under conditions suitable for the disinfection. In an aspect, the peroxyformic acid is generated and used within a matter of minutes at a point of use. In an aspect, at least about 1 ppm peroxyformic is generated within less than 1 minute of contacting the first reagent and the second reagent. In an aspect, at least about 1 ppm peroxyformic is generated within less than about 55 seconds, 50 seconds or less, 45 seconds or less, 40 seconds or less, 35 seconds or less, 30 seconds or less, 25 seconds or less, 20 seconds or less, 15 seconds or less, 10 seconds or less, or 5 seconds or less. In an aspect, the reaction to form a liquid comprising at least about 1 ppm peroxyformic acid is near instantaneous. In an aspect, at least about 100 ppm or at least about 500 ppm peroxyformic is generated within about 5 minutes or less of contacting the first reagent and the second reagent. In an aspect, at least about 100 ppm or 500 ppm peroxyformic is generated within less than about 4 minutes, 3 minutes or less, 2 minutes or less, or 1 minute or less.

In further aspects, the present peroxyformic acid forming compositions can be configured to form a liquid, e.g., a solution, that comprises any suitable concentration of peroxyformic acid within any suitable time. For example, the first reagent and the second reagent in the present peroxyformic acid forming compositions can be configured to be contacted with each other to form a liquid and/or solid, e.g., a solution, that comprises any suitable concentration of peroxyformic acid within any suitable time. In some embodiments, the first reagent and the second reagent can be configured to be contacted with each other to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm or greater of peroxyformic acid within 1 minute of the contact time.

In still further aspects, the solid composition can be configured to be contacted with a liquid to form a liquid, e.g., a solution, that comprises any suitable concentration of peroxyformic acid within any suitable time. In some embodiments, the solid composition can be configured to be contacted with a liquid to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm or greater, of peroxyformic acid within 1 minute of the contact time.

Methods for Treating a Target or Surface Using a Saturated Wipe

In yet another aspect, the various methods for treatment using the peroxyformic acid generated according to the methods of the invention can be delivered using a saturated wipe. Disposable substrates are commonly used in cleaning applications. Suitable substrates include woven and nonwoven fabrics and various combinations thereof. Such substrates can be impregnated with the peroxyformic acid generated compositions according to the invention or with the generated peroxyformic acid at a point of use for application using the substrate. The resulting disinfecting products fabricated from such impregnated substrates are accepted as a convenient and practical means for cleaning surfaces, such as disclosed in U.S. Patent Publication No. 2014/0271762 which is incorporated herein by reference in its entirety.

In an embodiment, microfiber products are used herein for the delivery of the peroxyformic acid for consumer cleaning, such as those constructed from split conjugated fibers of polyester and polyamide, or alternatively polyamide free versions. In an aspect, the peroxyformic acid generated according to the methods of the invention is used to coat the substrate for contacting a surface. In another aspect, a first or second substrate for the peroxyformic acid generated according to the methods of the invention is impregnated into the substrate which thereafter contacts the remaining chemistry (e.g. first or second composition containing the other component for generating the peroxyformic acid) to generate the peroxyformic acid composition at a point of use by a user.

The peroxyformic acid (or a first or second composition for generating the peroxyformic acid) coated onto the substrate may optionally further include one or more additives such as fragrances, dyes, pigments, emollients, bleaching agents, anti-static agents, anti-wrinkling agents, odor removal/odor capturing agents, ultraviolet light protection agents, insect repellency agents, souring agents, mildew removing agents, allergicide agents, and mixtures thereof.

In an embodiment, disinfectants are coated onto the substrate for length of times from about 20 seconds, 30 seconds, 45 seconds, 1 minute, 2 minutes, 5 minutes, 10 minutes and up to about 7 days. Pre-coated wipes may be sold in airtight containers. Such pre-coated wipes may be in contact with the disinfectant for seconds, to hours to days, and preferably up to one week with the peroxyformic acid according to the invention.

Methods for Skin and Surface Sanitizing and Disinfecting

In yet another aspect, the various methods for treatment using the peroxyformic acid generated according to the methods of the invention can be employed for skin sanitizing and disinfectant, including for example methods for mastitis control. The rate of formation of the peroxyformic acid in situ is particularly beneficial for the application of use for skin disinfection. The disinfectant is generated in situ and provides on demand disinfectant. Beneficially, the applications of use employing the solid compositions for in situ generation of the disinfectant peroxyformic acid provide glycerol as a leaving group which is further beneficial to the skin treated with the disinfectant composition. Without being limited to a particular mechanism of action and/or benefit, the glycerol provides an emollient to the treated skin surface. In an embodiment, the surface, including skin or other external or mucosal surfaces of an animal in need of disinfectant is contacted with an effective amount of peroxyformic acid for a sufficient time to reduce and/or remove microbial population on said treated surface.

The present methods can use any suitable concentration of peroxyformic acid for disinfecting skin by applying a liquid, namely a solution, to the skin surface. In some embodiments, the present methods can comprise contacting a surface with from about 10 ppm to about 1,000 ppm peroxyformic acid, e.g., 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, or 950-1,000 ppm peroxyformic acid. In a preferred aspect, the methods of contacting provide from about 10 ppm to about 500 ppm peroxyformic acid for disinfectant generated in situ within a matter of minutes.

The present methods can comprise contacting a surface with an effective amount of peroxyformic acid for any suitable amount of time. In some embodiments, the present methods can comprise contacting a surface with an effective amount of peroxyformic acid for from about 1 minute to about an hour, e.g., about 1 minute, 2 minutes, 3 minutes, 4 minutes, 5 minutes, 6 minutes, 7 minutes, 8 minutes, 9 minutes, or 10 minutes or greater. In an aspect, the contacting time is preferably less than 10 minutes, and more preferably less than 5 minutes. In an aspect, the contacting occurs for a period of time before degradation of the peroxyformic acid composition.

The present methods can be used to treat a surface, including skin, having a contaminated surface from any suitable microbial populations. In some embodiments, the present method can be used to treat a surface made of or from a prokaryotic microbial population, e.g., a bacterial or an archaeal population. Exemplary bacterial populations include a population of *Staphylococcus aureus, Streptococcus agalactiae, Streptococcus dysagalactiae*, and *Streptococcus uberis*. The methods are suitable for disinfecting common mastitis causing pathogens, including both contagious and environmental pathogens.

Contagious bacteria, such as *Streptococcus agalactiae* and *Staphylococcus aureus*, primarily colonize host tissue sites such as mammary glands, teat canals, teat skin lesions etc. and are spread from one infected cow to another during the milking process. Environmental bacteria, often streptococci, enterococci and coliform organisms, are commonly present within the cow's surroundings from sources such as cow feces, soil, plant material, bedding or water, and infect by casual opportunistic contact with an animal during the inter-milking period.

The methods of disinfecting a skin surface may include the contacting of a surface with an effective amount of the disinfecting composition by various routes of application. In an aspect, the disinfectant composition can contact the surface by dipping the skin surface (such as teats) in solution, spray applying the solution to the surface, or by dipping in a foam produced from the solution. In a preferred aspect, a method of treating teats of lactating animals comprises applying an effective amount of the composition by dipping the teats in solution, spray applying the solution to teats, or by dipping in a foam produced from the solution.

The peroxyformic acid used in the present methods can be prepared using any suitable methods disclosed herein. In some embodiments, the peroxyformic acid used in the present methods can be prepared by contacting an ester of a polyhydric alcohol and formic acid, with hydrogen peroxide or a substance that generates hydrogen peroxide when in contact with a liquid. For example, the peroxyformic acid used in the present methods can be prepared using any of the peroxyformic acid forming compositions described above or any of the methods described above. In other embodiments, the peroxyformic acid used in the present methods can be prepared in situ for the application of the formed peroxyformic acid.

In some embodiments, the present methods can further comprise contacting the surface with a polyol, including a skin conditioning polyol, or other emollient and/or humectant. In an aspect, an emollient and/or humectant is formulated with the disinfectant to lubricate, condition and generally reduce and promote the healing of irritation on the surface of application which may result either from the disinfectant agent, from mechanical action employed or from environmental conditions such as wind chill, dehydration, abrasion and sunburn. Any water soluble or dispersible skin conditioning agent may be used in this present invention. Compositions such as polyhydric alcohols are useful in the invention including glycerin, sorbitol, mannitol, and propylene glycol and its homopolymers; fatty acid esters of simple monohydril alcohols including isopropyl palmitate or isopropyl myristate and similar esters; polyol esters of fatty acids; and, ethoxylated lanolins, vegetable oils, and similar natural sourced derivatives such as aloe. Preferred emollients to be used in the invention include glycerin, sorbitol, and propylene glycol.

In a preferred aspect, polyols include glycerin, propylene glycol, sorbitol, polyglycerol, and mixtures thereof. In a preferred aspect, the surface is contacted with a disinfectant liquid, including a solution comprising the peroxyformic acid and the polyol in an amount from about 0.5 wt-% to about 50 wt-% of the disinfectant liquid. In a preferred aspect, the surface is contacted with a disinfectant liquid, including a solution comprising the peroxyformic acid and the polyol in an amount from about 1 wt-% to about 10 wt-% of the disinfectant liquid.

In some embodiments, the present methods can further comprise contacting the surface with the peroxyformic acid and a $C_2$-$C_{22}$ percarboxylic acid. Exemplary $C_2$-$C_{22}$ percarboxylic acids include peroxyacetic acid, peroxyoctanoic acid and/or peroxysulfonated oleic acid. In other embodiments, the present methods can further comprise contacting the surface with a surfactant. Exemplary surfactants include an anionic surfactant, a nonionic surfactant, a cationic surfactant as well as an amphoteric surfactant. In still other embodiments, the present methods can further comprise contacting the surface with a solvent. Exemplary solvents include an alcohol, an ester, a glycol ether, an amide, a hydrocarbon etc. In still other embodiments, the present methods can further comprise contacting the surface with an enzyme.

In some embodiments, the present methods can further comprise contacting the surface with the peroxyformic acid composition further comprising surface wetting agents. The surfactant or surfactant admixture of the present invention can be selected from compatible water soluble or water dispersible nonionic, or anionic surface-active agents; or mixtures of each or both types. Nonionic and anionic surfactants offer diverse and comprehensive commercial selection, low price; and, most important, excellent detersive effect-meaning surface wetting. Surface-active or "wetting agents" function to increase the penetrant activity of the invention into the tissue surface at risk from mastitis causing pathogens. Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Also useful in the present invention are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counterions) associated with these polar groups, sodium, lithium and potassium impart water solubility and are most preferred in compositions of the present invention. Examples of suitable synthetic, water soluble anionic compounds are the alkali metal (such as sodium, lithium and potassium) salts or the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl naphthalene sulfonate, dialkyl naphthalene sulfonate and alkoxylated derivatives. Other anionic detergents are the olefin sulfonates, including long chain alkene sulfonates, long chain hydroxyalkane sulfonates or mixtures of alkenesulfonates and hydroxyalkanae-sulfonates and alkylpoly (ethyleneoxy) ether sulfonates. Also included are the alkyl sulfates, alkyl poly (ethyleneoxy) ether sulfates and aromatic poly (ethyleneoxy) sulfates such as the sulfates or condensation products of ethylene oxide and nonyl phenol (usually having 1 to 6 oxyethylene groups per molecule).

In an aspect, oxidatively susceptible or acid hydrolytically susceptible surfactants are employed as wetting agents. Exemplary oxidatively susceptible surfactants comprise polyethylene glycol based surfactant, polyglycerol, polyol sugar based surfactants, and mixtures thereof. Examplary surfactants include, alcohol ethoxylates, EO/PO copolymers exemplified by poloxamers, glycerol and polyglycerol ester surfactants, polysorbate surfactants exemplified by Tween® surfactants, and sugar based surfactants exemplified by alkyl polyglucosides such as Glucopon® surfactants. Additional disclosure of suitable wetting agents is set forth in U.S. Pat. No. 6,749,869 and Reissue No. RE41279E, each of which are herein incorporated by reference in their entirety. Beneficially, the disinfectant compositions are stable with peroxyformic acid compositions generated in situ, unlike conventional food based or skin friendly surfactants which are not stable in highly oxidative or very low pH environments of traditional equilibrium or concentrate peracids.

In some embodiments, the present methods can further comprise contacting the surface with the peroxyformic acid composition further comprising a dye or colorant. In an aspect, the peroxyformic acid of the disinfectant composition is provided with a dye or colorant to provide a mechanism for color marking of the disinfectant composition. Beneficially, the peroxyformic acid generated in situ does not have shelf-stability and formulation incompatibility with traditional colorants, as is experienced with traditional equilibrium and concentrate peracid systems. In an aspect, the dye or colorant is a food and/or drug additive dye. In an aspect, the dye or colorant is not a color changing or indicator system. In an aspect, complexed iodines offer the advantage of being chromophoric, i.e. easily visible when applied onto the skin. Other antimicrobial agents do not have this feature; therefore, compositions of this invention may include a water soluble or dispersible coloring agent (dye or pigment or mixtures) which renders the composition chromophoric, having sharp contrast to teat skin and permitting the dairy herd manager to visually discern that the teats have been treated.

In further aspects, the disinfectant compositions may be comprised of any number of optional ingredients. Generally, in accordance with the invention, there may be included within this composition formulary adjuvants which assist in the application of the invention with respect to physical and chemical stability, barrier film formation, skin or teat health maintenance, performance, physical form and manufacturing process anesthetics. Of course, these functions may be accomplished exclusively by composition ingredients already described or admixtures thereof; however, formulary or application or performance situations may occur requiring additional effect which may be accomplished by introducing an additional inorganic or organic agent or agents and mixtures thereof into the composition.

The compositions of the invention may optionally include medicaments, for example sunscreens such as paraamino benzoic acid and healing agents such as allantoin or urea to provide curative action and stimulation of formation of new tissue; preservatives such as methyl paraben, propyl paraben, sorbic and benzoic acids or salts thereof to retard bacterial growth and prolong shelf life; antioxidants such as BHT (butylated hydroxytoluene), BHA (butylated hydroxyanisole), TBHQ (tert-butylhydroquinone), or propyl gallate to retard oxidative or hydrolytic degradation; sequestering agents such as aminopolyacetates, polyphosphonates, aminopolyphosphonates, polycarboxylates, and condensed phosphates; dispersants or suspending agents having polyelectrolytic character such as polyacrylate and similar polycarboxylates of homopolymeric or copolymeric structure; and manufacturing processing agents, for example defoam additives employed to facilitate blending and mixing.

A wide variety of ingredients useful in skin disinfection, including mastitis control, treatment can be included in the compositions hereof. This list is not intended to be exhaustive and other optional ingredients, which may not be listed, but which are well known in the art, may also be utilized in the composition. The examples are not intended to be limited in any way. In certain cases, some of the individual adjuvants may overlap other categories. The adjuvants employed will be selected so as not to interfere with the antimicrobial action of the composition and to avoid physical or chemical instability of the product.

The present methods can be conducted at any suitable temperature ranges as disclosed herein. In general, the pH of bovine mastitis control treatments can vary from a low of about pH 2.0 to a maximum of approximately 11.0 depending primarily upon the choice of antimicrobial agent being incorporated in the composition because optimal efficacy normally occurs with a specific, narrow, pH range. Therefore the buffering agent or system is chosen accordingly. The present methods are preferably conducted at a slightly alkaline pH, or a near neutral pH of the peroxyformic acid compositions. In some embodiments, the pH is from about 2-9, 3-8, and preferably 4-7.

Beneficially, the methods of disinfection are suitable for in situ generation of the peroxyformic acid under conditions suitable for the disinfection. In an aspect, the peroxyformic acid is generated and used within a matter of minutes at a point of use. In an aspect, at least about 1 ppm peroxyformic is generated within less than 1 minute of contacting the first reagent and the second reagent. In an aspect, at least about 1 ppm peroxyformic is generated within less than about 55 seconds, 50 seconds or less, 45 seconds or less, 40 seconds or less, 35 seconds or less, 30 seconds or less, 25 seconds or less, 20 seconds or less, 15 seconds or less, 10 seconds or less, or 5 seconds or less. In an aspect, the reaction to form a liquid comprising at least about 1 ppm peroxyformic acid is near instantaneous. In an aspect, at least about 100 ppm or at least about 500 ppm peroxyformic is generated within about 5 minutes or less of contacting the first reagent and the second reagent. In an aspect, at least about 100 ppm or 500 ppm peroxyformic is generated within less than about 4 minutes, 3 minutes or less, 2 minutes or less, or 1 minute or less.

In further aspects, the present peroxyformic acid forming compositions can be configured to form a liquid, e.g., a solution, that comprises any suitable concentration of peroxyformic acid within any suitable time. For example, the first reagent and the second reagent in the present peroxyformic acid forming compositions can be configured to be contacted with each other to form a liquid and/or solid, e.g., a solution, that comprises any suitable concentration of peroxyformic acid within any suitable time. In some embodiments, the first reagent and the second reagent can be configured to be contacted with each other to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm or greater of peroxyformic acid within 1 minute of the contact time.

In still further aspects, the solid composition can be configured to be contacted with a liquid to form a liquid, e.g., a solution, that comprises any suitable concentration of peroxyformic acid within any suitable time. In some embodiments, the solid composition can be configured to be contacted with a liquid to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm or greater, of peroxyformic acid within 1 minute of the contact time.

Methods for Treating Laundry Articles

In an aspect, the peroxyformic acid compositions are suitable for treating laundry soils and cleaning articles, e.g., textiles, which have become soiled. In an aspect, additional functional ingredients, including those set forth in U.S. Publication No. 2013/0247308 (which is herein incorporated by reference in its entirety) can optionally be used in combination with the peroxyformic acid compositions disclosed herein for laundry applications. The compositions of the present invention either in combination with additional functional ingredients, alone and/or in combination with additional cleaning agents, can be used to remove stains from any conventional textile, including but not limited to, cotton, poly-cotton blends, wool, and polyesters. The compositions can be used on any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated.

The laundry item can be processed in a laundry washing machine like a washer extractor or a tunnel washer. A washer extractor that can be used includes a drum having an interior for holding laundry, a motor constructed and arranged for rotating the drum, a water inlet for introducing water into the drum interior, a chemical inlet for introducing chemicals into the drum interior, a drain for allowing fluid to drain from the drum interior, and a processing unit constructed for operating the washer extractor. The processing unit can be constructed to provide a washing cycle for washing laundry with a cleaning and disinfecting composition solution of the first component, a rinsing cycle for removing at least a portion of the detergent use solution, and a treatment cycle for treating laundry with a bleaching composition of the second component.

In conventional, industrial and/or commercial laundry washing applications of use, the peroxyformic acid compositions can be employed for removing soils from a textile either inside or outside a washing machine, when employing a method of removing soils in a laundry application. In some aspects, when the composition is employed outside the washing machine it is used in a concentrated formulation. In other aspects, when the composition is employed inside the washing machine it is used in a diluted (or a highly diluted) formulation, such as within the wash liquor of a washing machine in order to remove soils from textiles.

In a conventional, industrial laundry washing facility, textile materials can be subjected to several treatment steps in an industrial sized laundry washing machine to provide cleaning. Exemplary treatment steps include a presoak or a prewash step, a wash step (e.g. soap and suds step), a rinse step for the removal of soil containing wash liquor, a bleach step (separate or in combination with the wash step), several optional rinse steps to remove the bleaching composition, an optional sour step to adjust the pH, softening step, and an extract step that often involves spinning the textiles to remove water. The compositions of the invention can be employed in such exemplary conventional prewash or presoak steps, washing steps, and/or alternatively be used in washing treatment steps that vary from such conventional processes. In addition, the compositions of the invention may be employed with a variety of laundry washing machines, including industrial, commercial and/or consumer machines (e.g. residential and/or home laundry washing machine).

The method for treating laundry according to the invention can be provided as part of an overall method for cleaning laundry according to the invention. That is, as part of a laundry cleaning operation, the compositions of the present invention can be used alone to treat the articles, e.g., textiles, or can be used in conjunction with conventional detergents suitable for the articles to be treated. A laundry cleaning process according to the invention can include the removal of soil, the removal of staining or the appearance of staining, and/or the reduction of a population of microbes. The compositions of the invention can be used with conventional detergents in a variety of ways. Such formulation can include, for example, detergents for a pre-wash or pre-soak step and/or a soap/suds/bleach step. In other embodiments, the compositions of the invention can be used to treat the article as a separate additive from a conventional detergent. The compositions can be provided in the form of a concentrate that is diluted with water to provide a use solution. Alternatively, the compositions can be provided in the form of a use solution (already diluted with water). When used as a separate additive, the compositions of the present invention can contact the article to be treated at any time. For example, the compounds and compositions of the invention can contact the article before, after, or substantially simultaneously as the articles are contacted with the selected detergent.

The use solution can be used for washing the articles. In an aspect, the compositions can be applied to a prewash step (e.g. a warm about 40-50° C.). In certain aspects, low water levels are employed for the warm prewash step. Thereafter the removal of the excess grease and oily soils from the surface of the article, the article can then be washed thoroughly in a main or conventional sud step (i.e. wash step) using detergents, bleaching agents and/or alkaline builders. In such embodiments, the compositions contact the article before the articles are contacted with the selected detergent, e.g. a pre-soak or a pre-wash situation, wherein the articles are contacted with the composition of the invention initially to emulsify soils on the substrate fabric. This step may include a contact time from at least a few minutes. This step may optionally include the use of a builder or component compositions for providing a source of alkalinity, such as to increase the pH from neutral to an alkaline pH, including for example of a pH of at least 10, or at least 11 or greater. The step may be conducted at a broad range of temperatures.

In an embodiment, the compositions provides a suitable bleaching step, and may be combined with an additional bleaching and/or antimicrobial step. This bleaching and antimicrobial step can follow or precede steps of washing the laundry with a composition of the invention and draining and/or rinsing the composition solution from the laundry. In other applications, it is expected that the bleaching and antimicrobial step can occur simultaneously with the washing step. It is expected that in situations where the soiling is relatively light, it may be advantageous to combine the washing step employing the emulsifying composition of the invention with the bleaching and antimicrobial step. That is, the bleaching and antimicrobial step can include a soil removal step and/or it can occur before or after a soil removal step.

In an aspect of the invention, the composition is particularly suited for use as an additive composition within a regular wash/laundry process. For example, as disclosed herein the compositions can be employed as a bleaching agent or booster to a regular suds bath (regular wash/laundry process) which already contains a main detergent, alkalinity, and/or possibly bleach. Such exemplary processes are disclosed herein the description of the invention. Additional description of suitable laundry methods which may employ the compositions of the present invention are set forth, for example, in U.S. patent application Ser. No. 12/726,073, which is herein incorporated by reference in their entirety.

In an aspect, the peroxyformic acid composition is employed at a pH value of a use solution, such as in the drum of a washer extractor or in a tunnel washer, at a pH from about 7 to about 14, from about 7 to about 13, from about 7 to about 12, from about 7 to about 11, from about 7 to about 10, from about 7 to about 9, or from about 7 to about 8.

EXAMPLES

The following examples are included for illustrative purposes only and are not intended to limit the scope of the invention.

Example 1. Perhydrolysis of Various Esters

Fifty (50) ppm various esters having the following structures

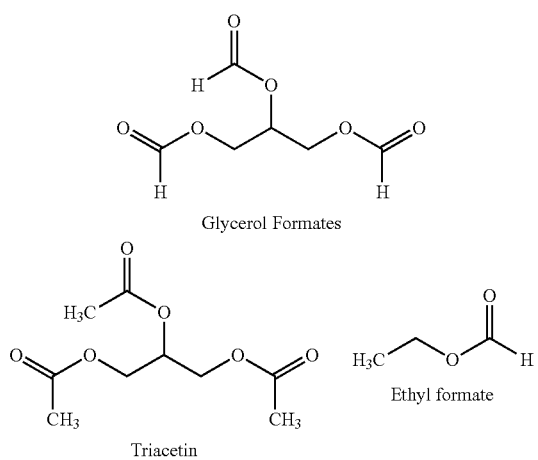

Glycerol Formates

Triacetin

Ethyl formate were added to 150 ppm $H_2O_2$ solution of pH 8.5 (DI water adjusted by adding 3.0 g of $NaHCO_3$ per liter of water and then adjusted pH with $Na_2CO_3$) respectively under ambient conditions. The concentration of peroxycarboxylic acids were measured by an iodometric titration method. The results are summarized in Table 1 below and shown in FIG. 1.

TABLE 1

Perhydrolysis of various esters

| Time (min) | Peracid (ppm) | | |
|---|---|---|---|
| | Glycerol formates | Ethyl formate | Triacetin |
| 1 | 1.40 | 0.00 | 0.00 |
| 5 | 3.04 | 0.00 | 0.00 |
| 10 | 3.03 | 0.00 | 0.00 |
| 15 | 2.79 | 0.00 | 0.00 |
| 25 | 1.89 | 0.00 | 0.00 |
| 35 | 1.21 | 0.00 | 0.00 |

Beneficially as shown in Table 1 the glycerol formate ester provides rapid generation of peroxyformic acid. The initial measurement point for peracid generation was 1 minute, however, according to the invention the peracid generation is near instantaneous. As shown, only the glyercol formates generated performic acid under the tested conditions (i.e. low pH), while no detectable peracid was generated using either ethyl formate or triacetin under the same conditions.

The rate of generation of performic acid from the glycerol formate ester is distinct from that shown for the ethyl formate ester, such as disclosed in U.S. Pat. Nos. 5,840,343 and 5,635,195 employing esters of formic acid (namely ethyl formate, methyl formate, and propyl formate) which fail to generate performic acid, nonetheless the rapid rate of conversion into peroxyformic acid, as set forth in the claimed invention and as evaluated according to this Example.

Example 2. Perhydrolysis of Various Polyhydric Alcohol Formic Acid Esters

Figure 2:
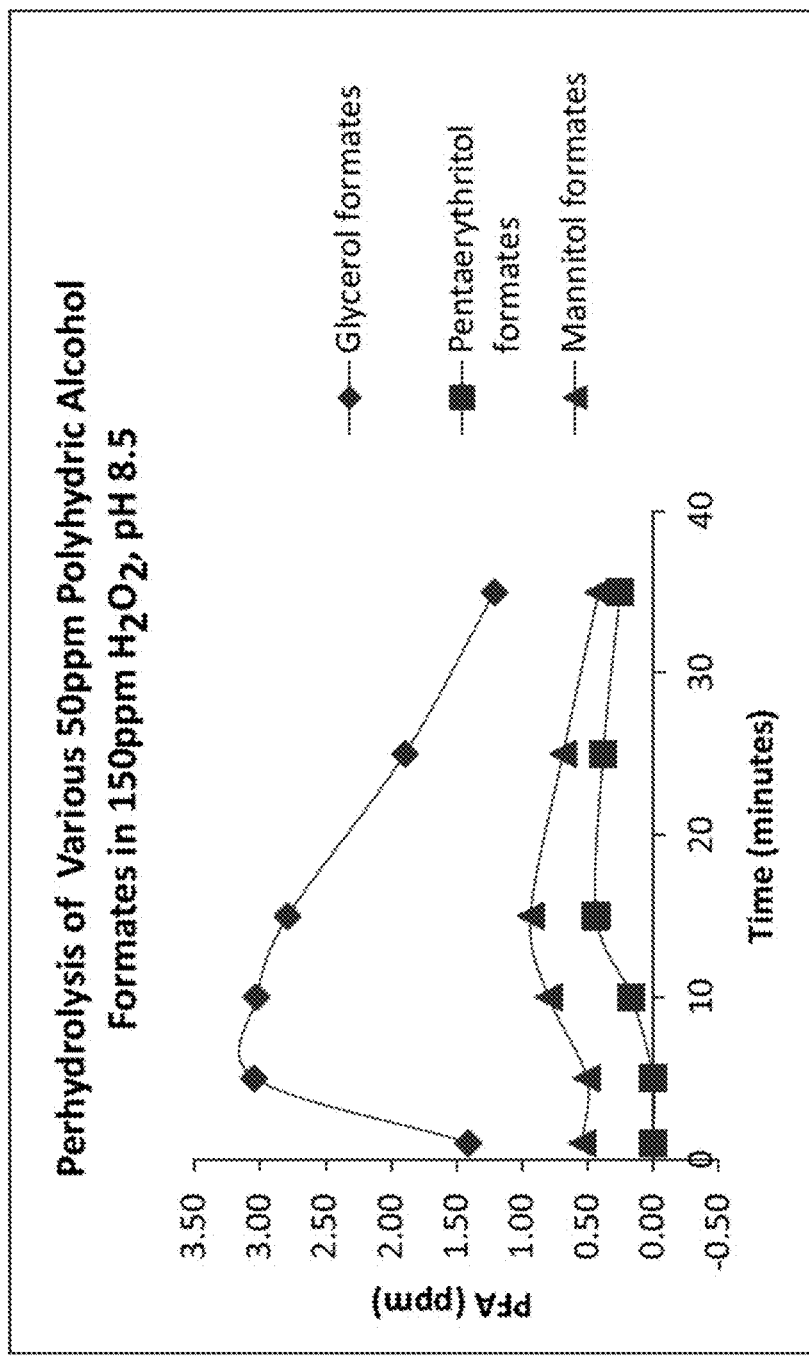
FIG. 2 illustrates perhydrolysis of various polyhydric alcohol formic acid esters according to embodiments of the invention.

Fifty (50) ppm various formic acid esters were added to 150 ppm $H_2O_2$ solution of pH 8.5 (DI water adjusted by adding 3.0 g of $NaHCO_3$ per liter of water and then adjusted pH with $Na_2CO_3$) respectively under ambient conditions. The concentration of peroxycarboxylic acids were measured by an iodometric titration method. The results are summarized in Table 2 below and shown in FIG. 2.

TABLE 2

Perhydrolysis of 50 ppm various polyhydric alcohl formic acid esters in 150 ppm $H_2O_2$, pH 8.5

| Time (min) | PFA (ppm) | | |
|---|---|---|---|
| | Glycerol formates | Pentaerythritol formates | Mannitol formates |
| 1 | 1.40 | 0.00 | 0.54 |
| 5 | 3.04 | 0.00 | 0.51 |
| 10 | 3.03 | 0.16 | 0.80 |
| 15 | 2.79 | 0.43 | 0.93 |
| 25 | 1.89 | 0.38 | 0.69 |
| 35 | 1.21 | 0.25 | 0.41 |

Example 3. Perhydrolysis of Glycerol Formates Under Various pH Conditions

Figure 3:
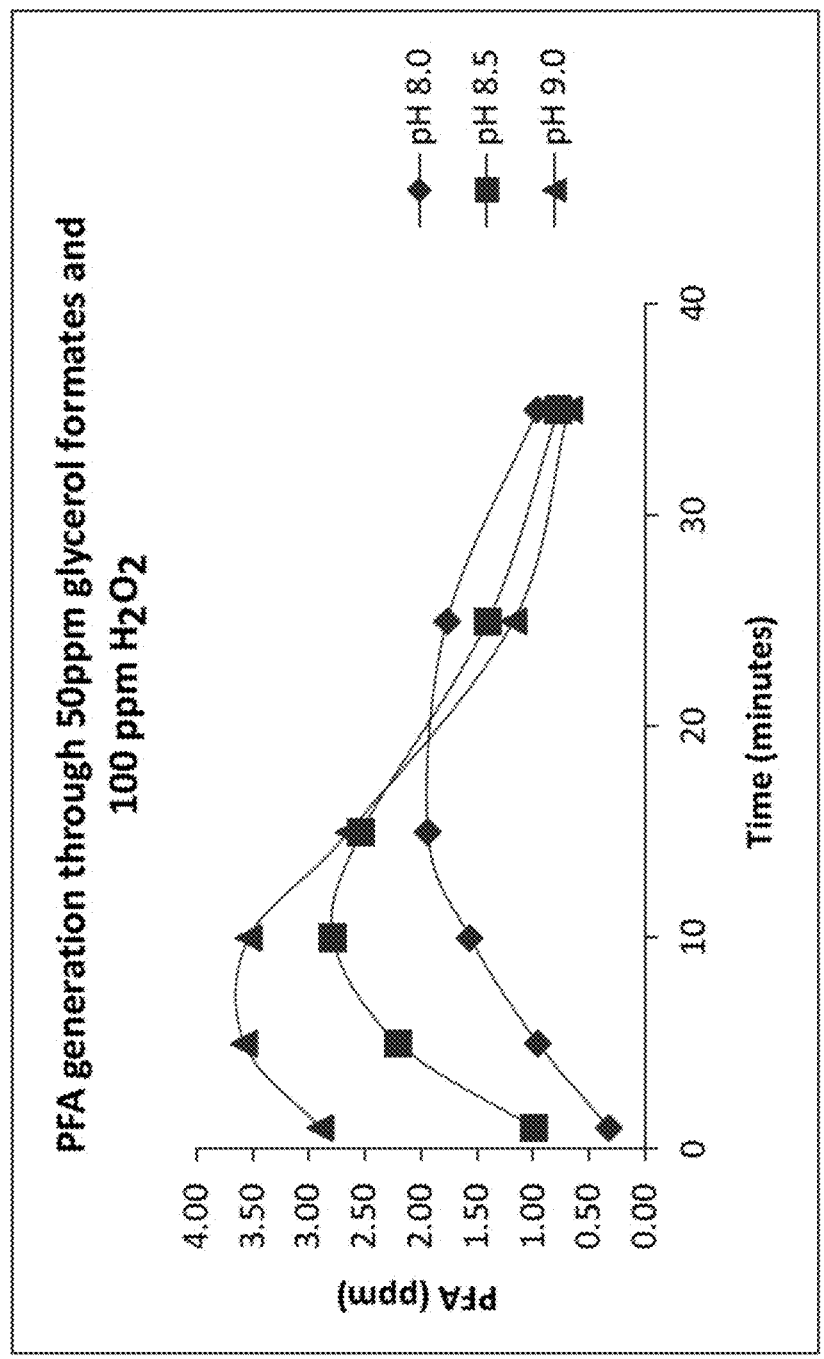
FIG. 3 illustrates perhydrolysis of glycerol formates under various pH conditions according to embodiments of the invention.

Fifty (50) ppm glycerol formates was added to 150 ppm $H_2O_2$ solution of various pHs (DI water adjusted by adding 3.0 g of $NaHCO_3$ per liter of water and then adjusted pH with $Na_2CO_3$) under ambient conditions. The concentration of peroxycarboxylic acids were measured by an iodometric titration method. The results are summarized in Table 3 below and shown in FIG. 3.

TABLE 3

Perhydrolysis of glycerol formatted under various pH

| Time (min.) | PFA (ppm) | | |
|---|---|---|---|
| | pH 8.0 | pH 8.5 | pH 9.0 |
| 1 | 0.32 | 0.99 | 2.90 |
| 5 | 0.96 | 2.20 | 3.58 |
| 10 | 1.56 | 2.78 | 3.53 |
| 15 | 1.94 | 2.53 | 2.64 |
| 25 | 1.77 | 1.40 | 1.17 |
| 35 | 0.96 | 0.77 | 0.68 |

Figure 4:
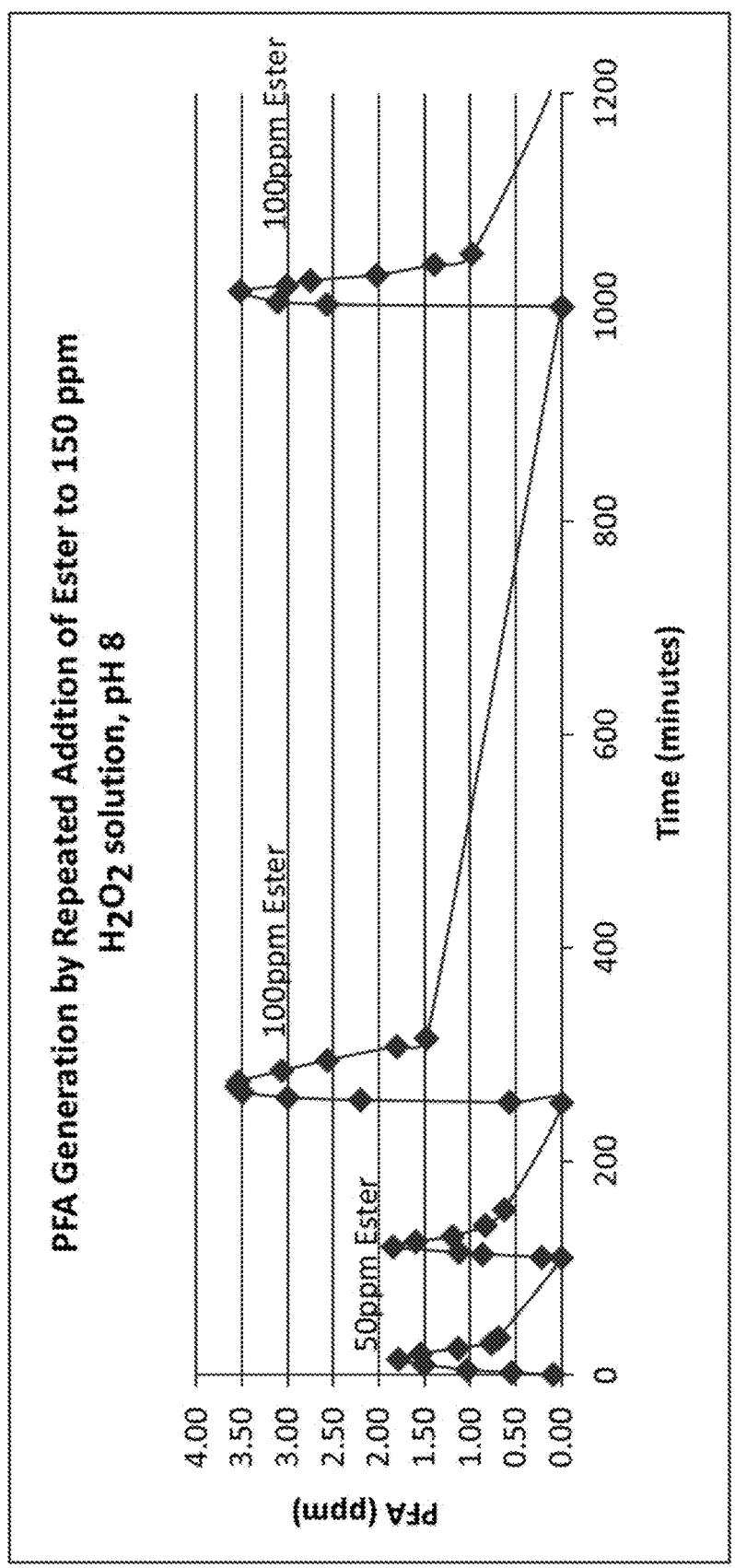
FIG. 4 illustrates generation of peroxyformic acid by repeated addition of glycerol formates according to embodiments of the invention.

Example 4. Generation of Peroxyformic Acid by Repeated Addition of Glycerol Formates Glycerol formates were added at various time point to 150 ppm $H_2O_2$ solution of pH 8.0 (DI water adjusted by adding 3.0 g of $NaHCO_3$ per liter of water and then adjusted pH with $Na_2CO_3$) under ambient conditions. The concentrations of peroxycarboxylic acids generated were measured by an iodometric titration method. The results are summarized Table 4 below and shown in FIG. 4.

TABLE 4

Generation of peroxyformic acid by repeated addition of glycerol formates to 150 ppm $H_2O_2$ solution, pH 8.0

| Time (min) | 50 ppm Glycerol Formate Sample size (g) | 150 ppm H2O2 Volume thiosulfate (mL) | pH 8.0 @ RT [PFA] ppm |
|---|---|---|---|
| 0.5 | 34.77 | 0.001 | 0.09 |
| 2.5 | 22.93 | 0.004 | 0.54 |
| 5 | 24.05 | 0.008 | 1.03 |
| 10 | 32.9 | 0.016 | 1.51 |
| 15 | 27.85 | 0.016 | 1.78 |
| 20 | 28.03 | 0.014 | 1.55 |
| 25 | 21.82 | 0.008 | 1.14 |
| 30 | 24.22 | 0.006 | 0.77 |
| 35 | 26.83 | 0.006 | 0.69 |
| TOTAL 1 HR Wait | 243.4 | | |
| 110 | Add 38 uL Glycerol Formate | 0 | 0.00 |
| 110.5 | 28.53 | 0.002 | 0.22 |
| 113.5 | 28.55 | 0.008 | 0.87 |
| 115 | 22.12 | 0.008 | 1.12 |
| 120 | 23.52 | 0.014 | 1.85 |
| 125 | 23.29 | 0.012 | 1.60 |
| 130 | 23.34 | 0.009 | 1.20 |
| 140 | 22.2 | 0.006 | 0.84 |
| 155 | 24.79 | 0.005 | 0.63 |
| TOTAL 1 HR Wait | 439.74 | | |
| 255 | Added 50 uL Glycerol Formate = 89 ppm | 0 | 0.00 |
| 255.5 | 22.05 | 0.004 | 0.56 |
| 257.5 | 28.12 | 0.02 | 2.20 |
| 260 | 24.8 | 0.024 | 3.00 |
| 265 | 26.58 | 0.03 | 3.50 |
| 270 | 26.15 | 0.03 | 3.56 |
| 275 | 24.52 | 0.028 | 3.54 |
| 285 | 26.32 | 0.026 | 3.06 |

TABLE 4-continued

Generation of peroxyformic acid by repeated addition of glycerol formates to 150 ppm $H_2O_2$ solution, pH 8.0

| Time (min) | 50 ppm Glycerol Formate Sample size (g) | 150 ppm H2O2 Volume thiosulfate (mL) | pH 8.0 @ RT [PFA] ppm |
|---|---|---|---|
| 295 | 24.19 | 0.02 | 2.56 |
| 308 | 20.63 | 0.012 | 1.80 |
| 315 | 25.17 | 0.012 | 1.48 |
| TOTAL 16-18 HR Wait | 688.27 | | |
| 1000 | Added 15.6 uL of Glycerol Formate = 89 ppm | 0 | 0.00 |
| 1000.5 | 21.68 | 0 | 0.00 |
| 1002.5 | 26.55 | 0.022 | 2.57 |
| 1005 | 25.93 | 0.026 | 3.11 |
| 1010 | 28.37 | | 0.00 |
| 1015 | 15.86 | 0.018 | 3.52 |
| 1020 | 14.4 | 0.014 | 3.01 |
| 1025 | 20.29 | 0.018 | 2.75 |
| 1030 | 12.23 | 0.008 | 2.03 |
| 1040 | 15.52 | 0.007 | 1.40 |
| 1050 | 12.62 | 0.004 | 0.98 |
| TOTAL | 881.72 | | |

Example 5. Perhydrolysis of Glycerol Formate in the Presence of Enzyme

Figure 5:
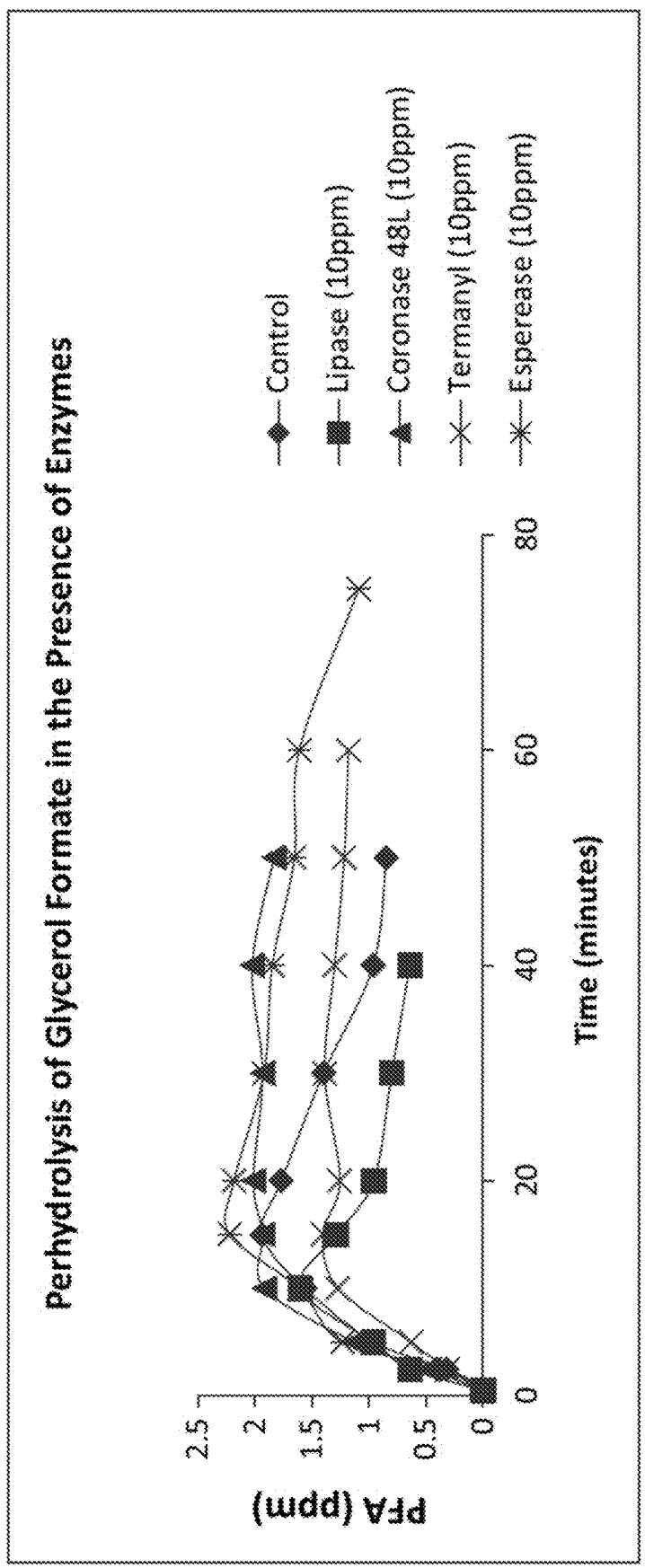
FIG. 5 illustrates perhydrolysis of glycerol formate in the presence of an enzyme according to embodiments of the invention.

Fifty (50) ppm of glycerol formates was added to 150 ppm $H_2O_2$ solution of pH 8.0 (DI water adjusted by adding 3.0 g of $NaHCO_3$ per liter of water and then adjusted pH with $Na_3CO_3$) in the presence of various 10 ppm (as product) enzyme under ambient conditions. The concentrations of peroxycarboxylic acids generated were measured by an iodometric titration method. The results are summarized in Table 5 below and shown in FIG. 5.

TABLE 5

Perhydrolysis of 50 ppm of glycerol formates in 150 ppm $H_2O_2$, pH 8.0 in the presence of various enzymes

| | PFA (ppm) | | | | |
|---|---|---|---|---|---|
| Time (min) | Control | Lipase (10 ppm) | Coronase 48L (10 ppm) | Termanyl (10 ppm) | Esperease (10 ppm) |
| 0.5 | 0 | 0 | 0 | 0 | 0 |
| 2.5 | 0.32 | 0.64 | 0.48 | 0.32 | 0.31 |
| 5 | 0.96 | 0.97 | 1.13 | 0.63 | 1.23 |
| 10 | 1.56 | 1.60 | 1.92 | 1.27 | 1.61 |
| 15 | 1.94 | 1.29 | 1.93 | 1.40 | 2.22 |
| 20 | 1.77 | 0.96 | 2.02 | 1.26 | 2.18 |
| 30 | 1.40 | 0.80 | 1.93 | 1.39 | 1.92 |
| 40 | 0.96 | 0.64 | 2.02 | 1.30 | 1.85 |
| 50 | 0.85 | | 1.83 | 1.22 | 1.66 |
| 60 | | | | 1.18 | 1.61 |
| 75 | | | | | 1.09 |

Example 6. Suspension Test of PFA Generated Through Perhydrolysis from Glycerol Formates in Cooling Tower Application The antimicrobial efficacy of peroxyformic acid generated through the perhydrolysis of glycerol formatted were tested against *pseudomonas* in cooling tower samples at both 25° C. and 37° C., along with the peroxyacetic acid (POAA) controls, and the results are summarized in Table 6 and 7 below.

TABLE 6

Microbial population (*pseudomonas*) in two cooling water samples (BP and Peninsula) 10 minutes after treatment with 5 ppm PFA from a reaction between 200 ppm $H_2O_2$ and 170 ppm glycerol formate at 25° C.

| Water Condition | Test Substance | Exposure Time | Test Temperature | Avg. $Log_{10}$ Growth | $Log_{10}$ Reduction |
|---|---|---|---|---|---|
| BP Cooling Water pH 8.74 | 5 ppm Ester PFA | 10 minutes | 25° C. | 2.74 | 2.93 |
| | 6.13 ppm POAA | | | 4.10 | 1.57 |
| | 12.3 ppm POAA | | | 3.26 | 2.41 |
| Peninsula Cooling Water pH 8.81 | 5 ppm Ester PFA | | | 2.76 | 2.42 |
| | 6.13 ppm POAA | | | 3.81 | 1.37 |
| | 12.3 ppm POAA | | | 3.30 | 1.88 |
| Inoculum Numbers - BP Cooling Water + Conc. Water | | | | 5.67 | |
| Inoculum Numbers - Peninsula Cooling Water + Conc. Water | | | | 5.18 | |

TABLE 7

Microbial population (*pseudomonas*) in two cooling water samples (BP and Peninsula) 10 minutes after treatment with 5 ppm PFA from a reaction between 200 ppm $H_2O_2$ and 170 ppm glycerol formate at 37° C.

| Water Condition | Test Substance | Exposure Time | Test Temperature | Avg. $Log_{10}$ Growth | $Log_{10}$ Reduction |
|---|---|---|---|---|---|
| BP Cooling Water pH 8.74 | 5 ppm Ester PFA | 10 minutes | 37° C. | 2.68 | 2.42 |
| | 6.13 ppm POAA | | | 2.84 | 2.26 |
| | 12.3 ppm POAA | | | 2.73 | 2.37 |
| Peninsula Cooling Water pH 8.81 | 5 ppm Ester PFA | | | 2.70 | 2.40 |
| | 6.13 ppm POAA | | | 2.76 | 2.34 |
| | 12.3 ppm POAA | | | 3.20 | 1.90 |
| Inoculum Numbers - BP Cooling Water + Conc. Water | | | | 5.10 | |
| Inoculum Numbers - Peninsula Cooling Water + Conc. Water | | | | | |

Example 7. High Concentration Disinfection Test of Peroxyformic Acid Generated Through Perhydrolysis Toward Various Microorganisms The antimicrobial efficacy of PFA generated through the perhydrolysis of glycerol formates were tested against various microorganisms in high concentration disinfection test following the standard protocol, and the results are summarized in Table 8 below.

TABLE 8

High Concentration Disinfectant Test of 270 ppm PFA Generated through the Perhydrolysis of Glycerol Formates against Various Microorganisms Bacterial Disinfection
Test Method: Use-dilution Method

| Test Substance | Test System | Exposure Time | Results |
|---|---|---|---|
| 13523-68-2 (~270 ppm PFA, pH 2.18) | *S. aureus* | 1 minute | 57/60 |
| | *P. aeruginosa* | | 54/60 |

*Clostridium difficile* Disinfection
Test Method: Modified 3 Step Method

| Test Substance | Test System | Exposure Time | $Log_{10}$ Reduction |
|---|---|---|---|
| 13523-68-1 (~270 ppm PFA, pH 2.21) | *C. difficile* | 1 minute | >5.72 |
| | | 3 minutes | >5.72 |
| | | 5 minutes | >5.72 |
| 13523-68-1 (~270 ppm PFA, pH 2.21) | *C. difficile* | 1 minute | 6.04 |

TABLE 8-continued

High Concentration Disinfectant Test of 270 ppm PFA Generated through the Perhydrolysis of Glycerol Formates against Various Microorganisms Virucidal Activity

| | | | |
|---|---|---|---|
| 13523-68-1 (~270 ppm PFA, pH 2.21) | Feline Calicivirus (FCV) | 1 minute | >3.75 |
| | Polio virusType 1 | | >4.50 |

Example 8. Preparation of Polyhydric Alcohol Formic Acid Esters

Preparation of Glycerol Formates

To a 100 ml three neck flask equipped with a vacuum distillation head, was added 25 g (0.27 mol) of glycerin, followed by 54 g (1.17 mol) of formic acid. With magnetic stirring, the flask was slowly heated to 140° C. through an oil bath. The water generated from the reaction, along with some formic acid start to be distilled off when the temperature of the solution reached ~115° C. As the reaction was completed (as evidenced by no distillate was come off), the distillation vacuum pump was turned on to remove the residual water and formic acid in the solution, afforded 24 g of odorless, colorless liquid. NMR analysis indicates the product is a mixture of glycerol mono-, di- and triformates.

Preparation of D-Mannitol Formates

Twenty (20) g of D-mannitol was dissolved in 60.65 g of 99% formic acid in a 100 ml of short-necked round-bottomed flask equipped a vacuum distillation head and a magnetic stirrer. With stirring, the flask was slowly heated to 120° C. by an oil bath. The water formed in the reaction and some excess amount of formic acid was distilled out slowly. When there was no distillate, the residual water and formic acid was removed by vacuum distillation. Afforded 25 g of odorless, colorless viscous liquid. The liquid obtained slowly solidified to a white solid on storage under ambient conditions. The solid was further purified by washing with ethyl acetate. The solid thus obtained has a melting point of greater than 50° C., and is soluble in water. NMR analysis indicates the product is a mixture of mannitol mono-, di- and tri-, tetra-, penta- and hexaformates.

Preparation of Pentaerythritol Formates

Forty (40) g of pentaerythritol was dissolved in 108 g of 99% formic acid in a 250 ml of short-necked round-bottomed flask equipped a vacuum distillation head and a magnetic stirrer. With stirring, the flask was slowly heated to 120° C. by an oil bath. The water formed in the reaction and some excess amount of formic acid was distilled out slowly. When there is no distillate, the residual water and formic acid was removed by vacuum distillation. Afforded 39 g of odorless, colorless viscous liquid. The liquid obtained slowly solidified to a white solid on storage under ambient conditions. The solid was further purified by washing with ethyl acetate. The solid thus obtained has a melting point of less than 50° C., and is soluble in water. NMR analysis indicates the product is a mixture of pentaerythritol mono-, di-, tri- and tetra-formates.

Preparation of Mannitol Hexaformates

Twenty (20) g of D-Mannitol was dissolved in 95 g of 99% formic acid in a 250 ml beaker. With stirring and cooling through an ice-water bath, 22 g of phosphorus pentaoxide was slowly added to the solution. After the addition of all phosphorus pentaoxide, large amount of precipitation was formed. The mixture was prevented from the moisture and allowed to warm to room temperature and leave at ambient conditions overnight. The mixture was then added to 500 ml of cold water, and the solid was collected by filtration, washed with 2% sodium bicarbonate solution, water, and dried at 50° C. Afforded 55 g of white solid. The solid is marginally soluble in water at room temperature.

Figure 6A:
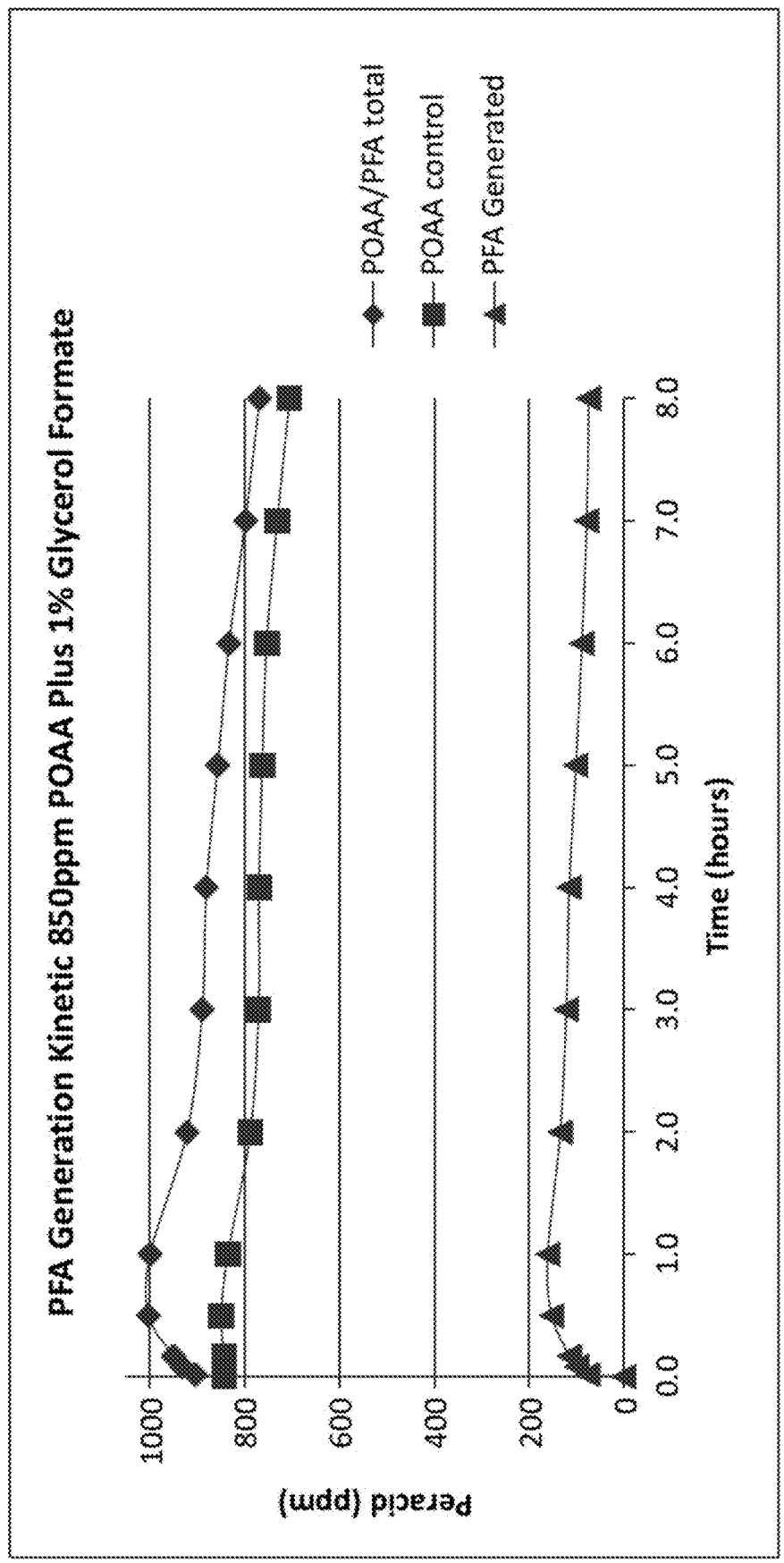
FIG. 6A illustrates generation of peroxyformic acid using POAA, glycerol formates and imidazole according to embodiments of the invention.
Figure 6B:
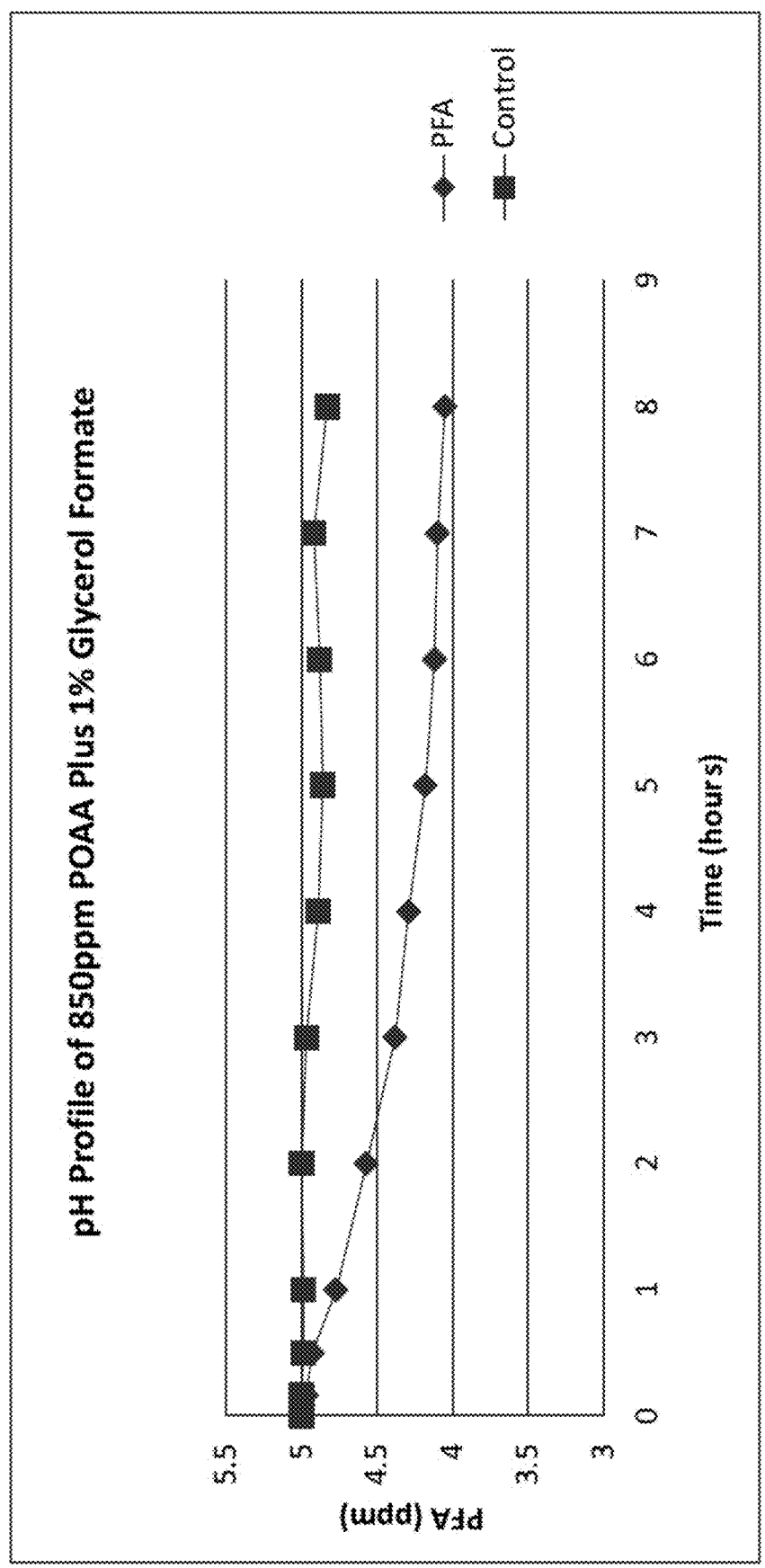
FIG. 6B illustrates the pH profile of the solution containing the formed peroxyformic acid according to embodiments of the invention.

Example 9. Generation of PFA Through 850 ppm POAA+1% Glycerol Formates and Imidazole Eight hundred fifty (850) ppm POAA was made through the dilution of a commercially available peroxyacetic acid composition (5.6% POAA, 26% 1-1202), referred to as POAA, using 5 grain tap water. One percent (1%) GlycForm with imidazole buffer was subsequently added to the POAA solution. A 850 ppm POAA control was created by adjusting pH=5.00 with imidazole. The PFA generation kinetics as well as the pH profile of the solution are shown in FIGS. 6A and 6B.

Figure 7:
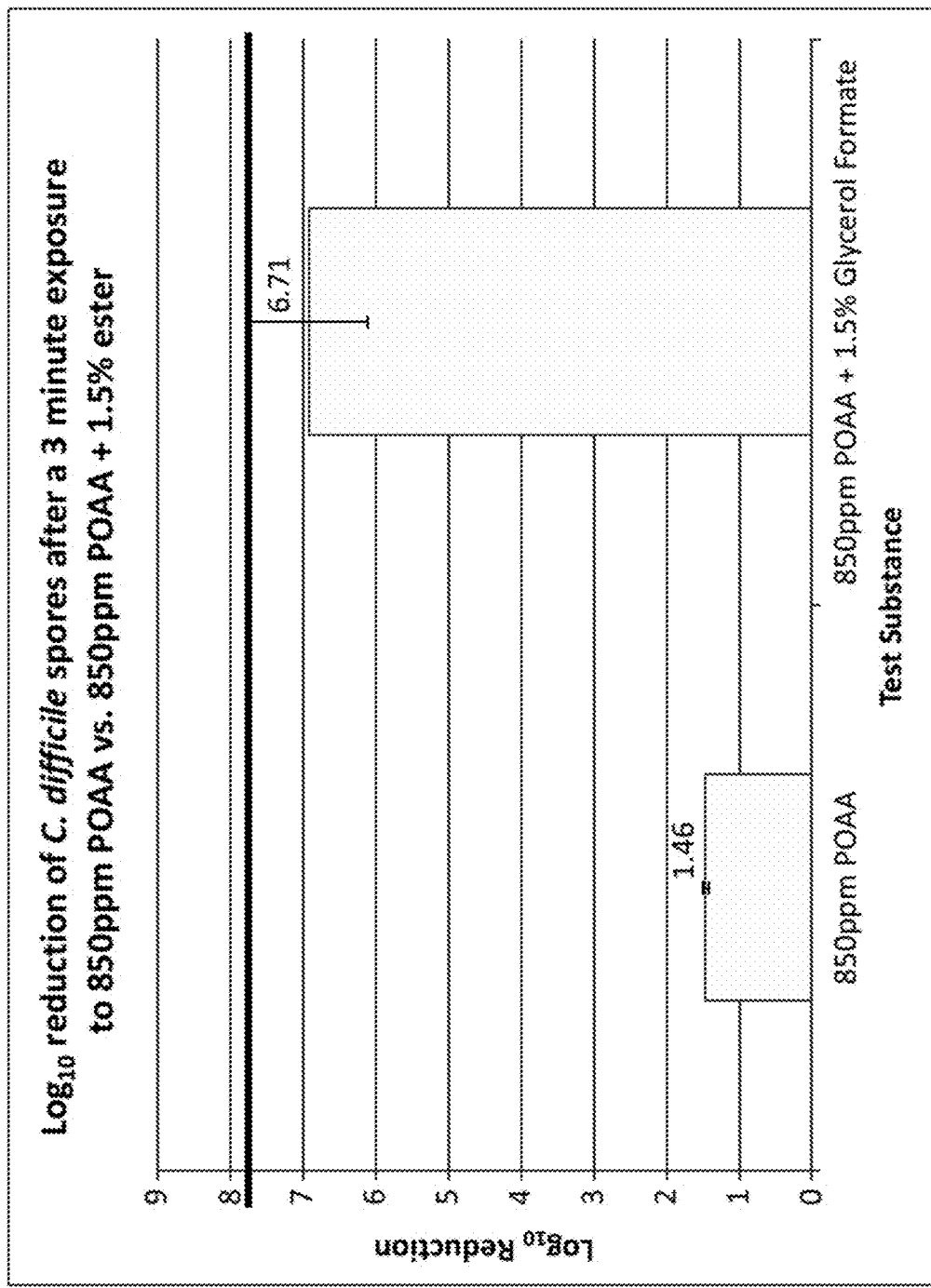
FIG. 7 illustrates efficacy against *C. difficile* spores with peroxyformic acid and POAA generated using POAA and glycerol formates according to embodiments of the invention.
Figure 8:
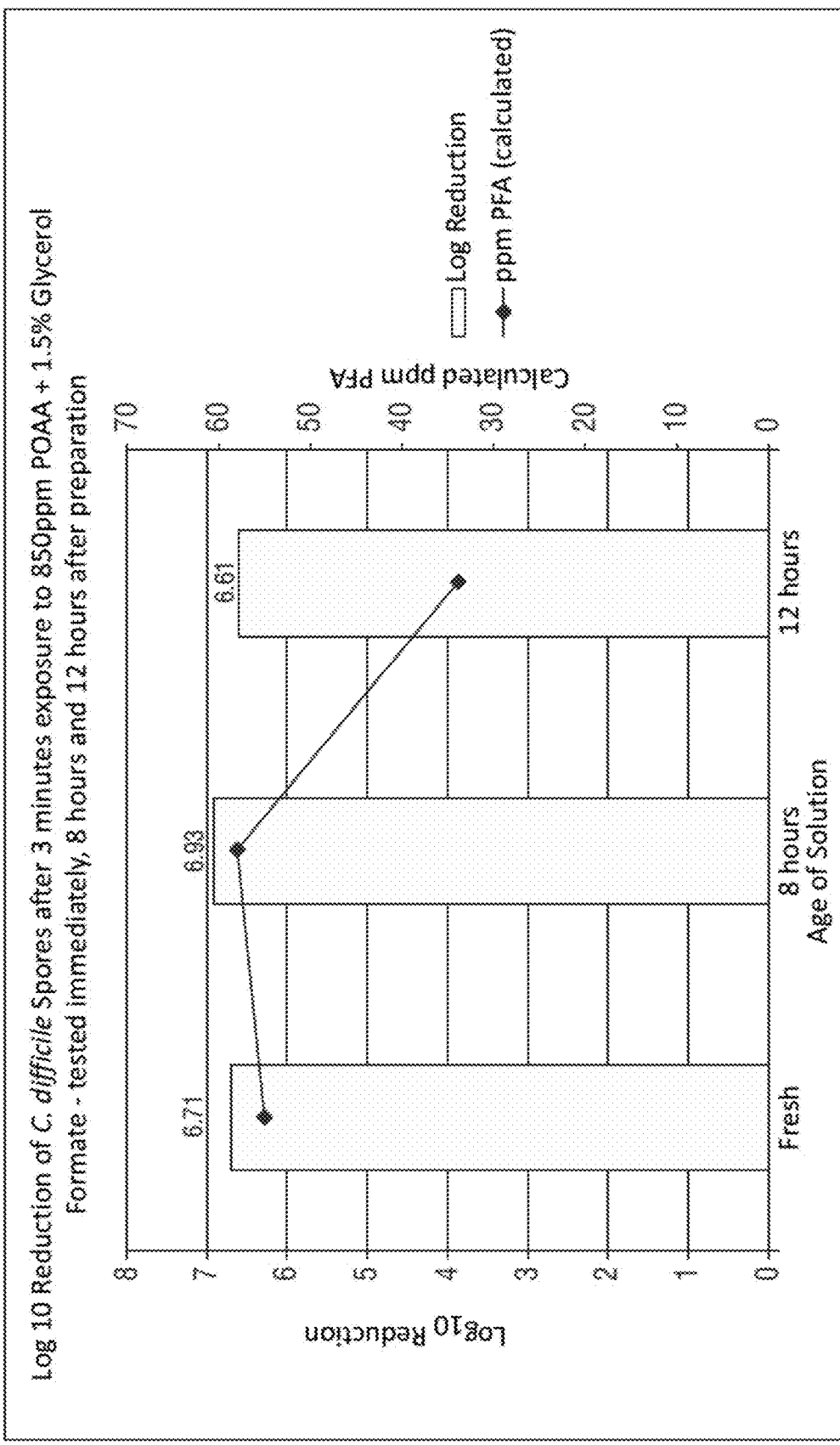
FIG. 8 illustrates efficacy against *C. difficile* spores at various time points after the mixing of POAA and glycerol formates according to embodiments of the invention.

Example 10. Efficacy Against *C. Difficile* Spores Using 850 ppm POAA Plus 1.5% Glycerol Formates Versus 850 ppm POAA Control To 850 ppm POAA prepared from a commercially available peroxyacetic acid composition (5.6% POAA, 26% $H_2O_2$), referred to as POAA, was added 1.5% glycerol formates with triazole buffer. Immediately after the mixing, the efficacy against *C. difficile* spores was tested following the EPA's SOP "MB-31-Quantitative Disk Carrier Test Method (QCT-2) Modified for Testing Antimicrobial Products against Spores of *Clostridium difficile* (ATCC 43598) on Inanimate, Hard Non-porous Surfaces." The contact time is 3 minutes. As a comparison, 850 ppm POAA was tested under the same conditions. The results are shown in FIG. 7. In addition, the efficacy against *C. difficile* spores were also tested 8 hours and 12 hours after the mixing of 850 ppm POAA and 1.5% glycerol formates with buffer, and the results are shown in FIG. 8.

Figure 9A:
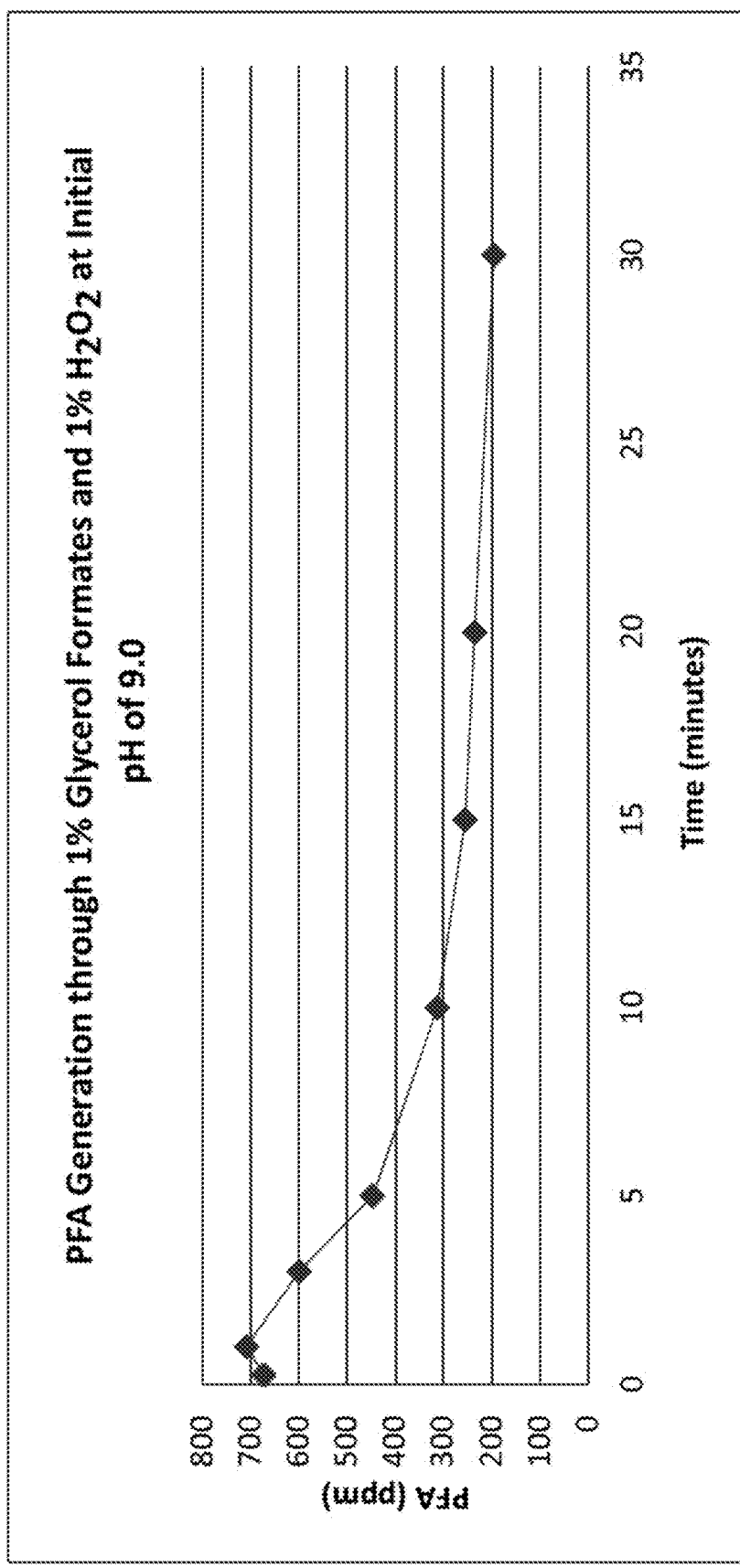
FIG. 9A illustrates fast generation of performic acid through the perhydrolysis of glycerol formates according to embodiments of the invention.
Figure 9B:
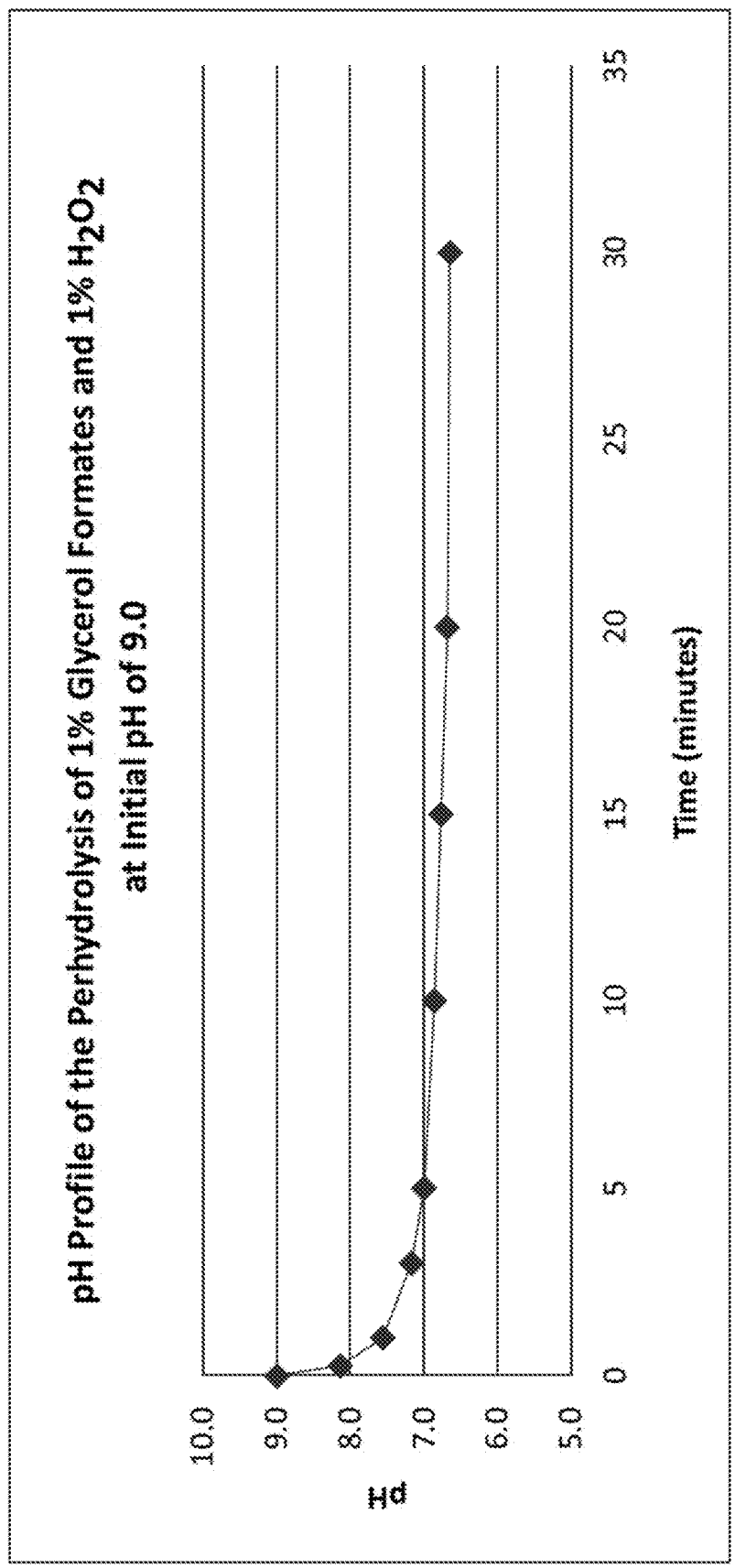
FIG. 9B illustrates the pH profile of the solution containing the formed peroxyformic acid according to embodiments of the invention.

Example 1. Fast Generation of Performic Acid Through the Perhydrolysis of Glycerol Formates Glycerol formates (0.58 g) was added to and mixed with 49.5 g of 1% $H_2O_2$ solution at pH 9.0 buffered with the mixture of 0.1 M $NaHCO_3$ and 0.1M $Na_2CO_3$ (80 to 20 V:V). The PFA generated was monitored by an iodometric titration method, and the pH of the solution was monitored by a pH meter. The results are summarized in Table 9 and FIGS. 9A and 9B.

TABLE 9

Performic Acid Generation and the pH Profile

| Time (min) | PFA (ppm) | pH |
|---|---|---|
| 0 | 0 | 9.0 |
| 0.25 | 673 | 8.14 |
| 1 | 709 | 7.56 |
| 3 | 598 | 7.17 |
| 5 | 447 | 7.00 |
| 10 | 313 | 6.86 |
| 15 | 255 | 6.77 |
| 20 | 235 | 6.68 |
| 30 | 195 | 6.65 |

Example 12. General Procedure for the Preparation of Sugar Formates

To a round-bottom flask was added sugar and formic Acid (Table 10) with stir bar. The flask was placed in a 120° C., affixed to a distillation apparatus oil bath and allowed to stir until no more water or formic acid was distilled off (2-4 hours). The flask was then allowed to stir under vacuum to strip off remaining liquid (1-2 hours). Product was collected and the properties of the sugar formates are summarized in the Table 11.

TABLE 10

Amount of Sugars and Formic Acid Used for the Synthesis of the Sugar Formates

| Sugar Alcohol | Amount (g) | Formic Acid Amount (g) |
|---|---|---|
| Sucrose | 125.00 | 270.00 |
| Dextrin (Maize) | 15.63 | 33.75 |
| Dextrin (Corn) | 15.63 | 33.75 |
| Maltodextrin (4-7) | 15.63 | 33.75 |
| Maltodextrin (13-17) | 15.63 | 33.75 |
| Soluble Starch | 15.63 | 33.75 |

TABLE 11

Physical Properties of Sugar Formates Prepared

| Sugar Formates | Form | Color | Hygroscopicity | Water Soluble |
|---|---|---|---|---|
| Sucrose | Solid | Dark Brown | Highly | Yes |
| Dextrin (Maize) | Solid | Brown | Medium | Yes |
| Dextrin (Corn) | Solid | Light Brown | No | Yes |
| Maltodextrin (4-7) | Solid | Light Brown | No | Yes |
| Maltodextrin (13-17) | Solid | Light Brown | Low | Yes |
| Starch | Solid | Light Brown | Medium | Yes |

Figure 10A:
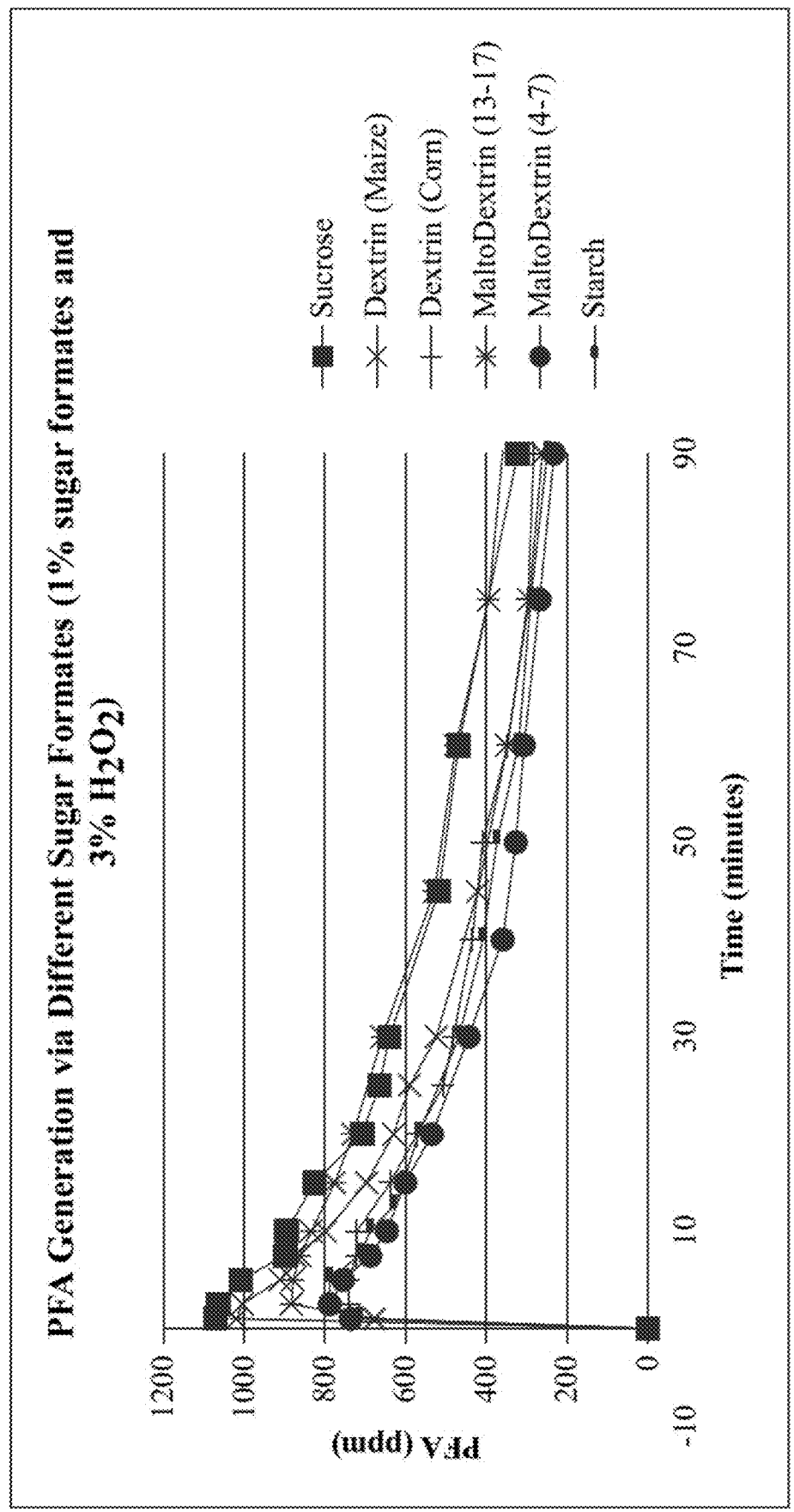
FIG. 10A illustrates generation of performic acid from sugar formates through perhydrolysis according to embodiments of the invention.
Figure 10B:
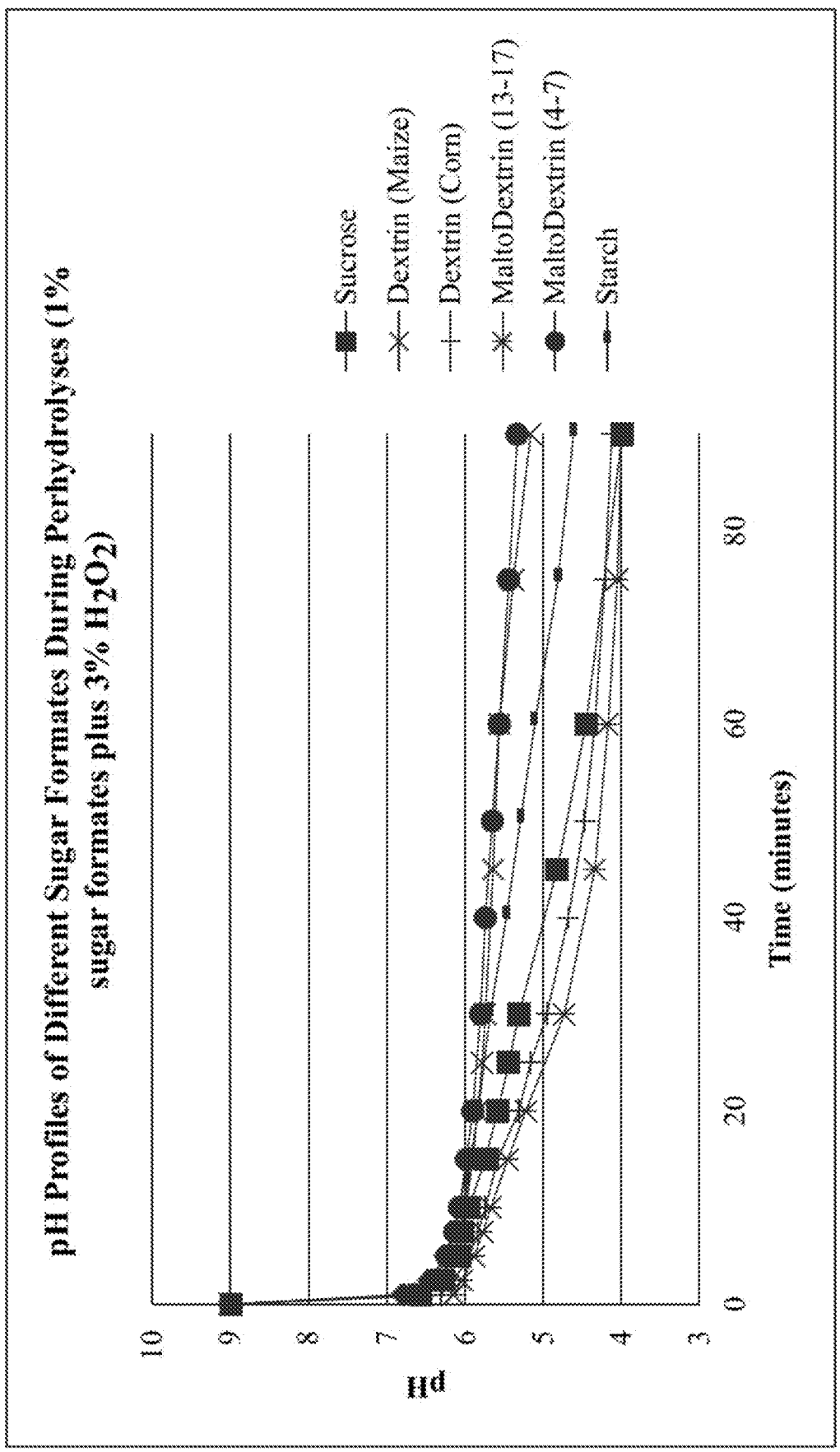
FIG. 10B illustrates the pH profile of the solution containing the formed peroxyformic acid according to embodiments of the invention.

Example 13. Generation of Performic Acid from Sugar Formates Through Perhydrolysis To 3% hydrogen peroxide solution of pH of 9.0 adjusted with 0.1M $NaHCO_3/Na_2CO_3$ was added 1% sugar formates, respectively. The performic acid formed was monitored by iodometric titration, and the pH was monitored by a pH meter, and the results are shown in FIGS. 10A and 10B.

Example 14. Reduction of *P. aeruginosa* Biofilm Using Different Concentrations of Peroxyformic Acid

Figure 11:
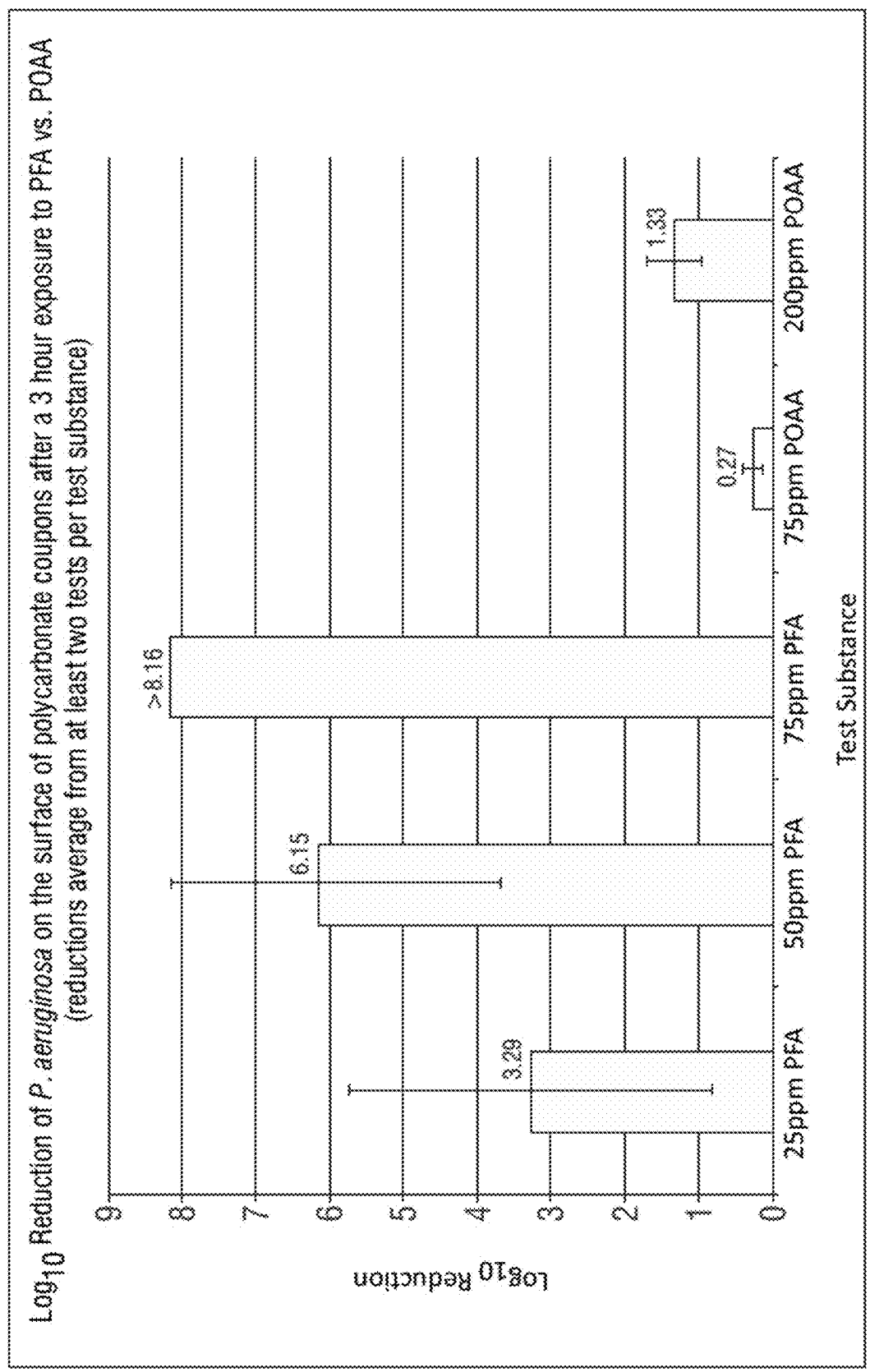
FIG. 11 illustrates reduction of *P. aeruginosa* biofilm using different concentrations of peroxyformic acid compared to peroxyacetic acid compositions according to embodiments of the invention.

*P. aeruginosa* ATCC 15442 biofilm was grown on the surface of 24 polycarbonate coupons following ASTM method E2562-12: Standard Test Method for Quantification of *Pseudomonas aeruginosa* Biofilm Grown with High Shear and Continuous Flow using CDC Biofilm Reactor. After 48 hours of biofilm establishment, the coupons were removed from the reactor and placed into individual centrifuge tubes. Three coupons per test substance were tested for disinfectant efficacy using ASTM method E2871-12: Standard Test Method for Evaluating Disinfectant Efficacy against *Pseudomonas aeruginosa* Biofilm Grown in CDC Biofilm Reactor using Single Tube Method. Each coupon was exposed to 4 mL of chemistry for an exposure time of 3 hours. After which, 16 mL of neutralizing medium was added on top of the chemistry to inactive antimicrobial performance. This was followed with a series of vortexing and sonicating steps to remove any biofilm from the coupon surface into the solution for plating and enumeration. As shown in FIG. 11, peroxyformic acid achieves significantly greater anti-biofilm efficacy with a concentration that is lower than POAA.

Example 15. Reduction of *P. aeruginosa* Biofilm Using Different Exposure Times of Peroxyformic Acid

Figure 12:
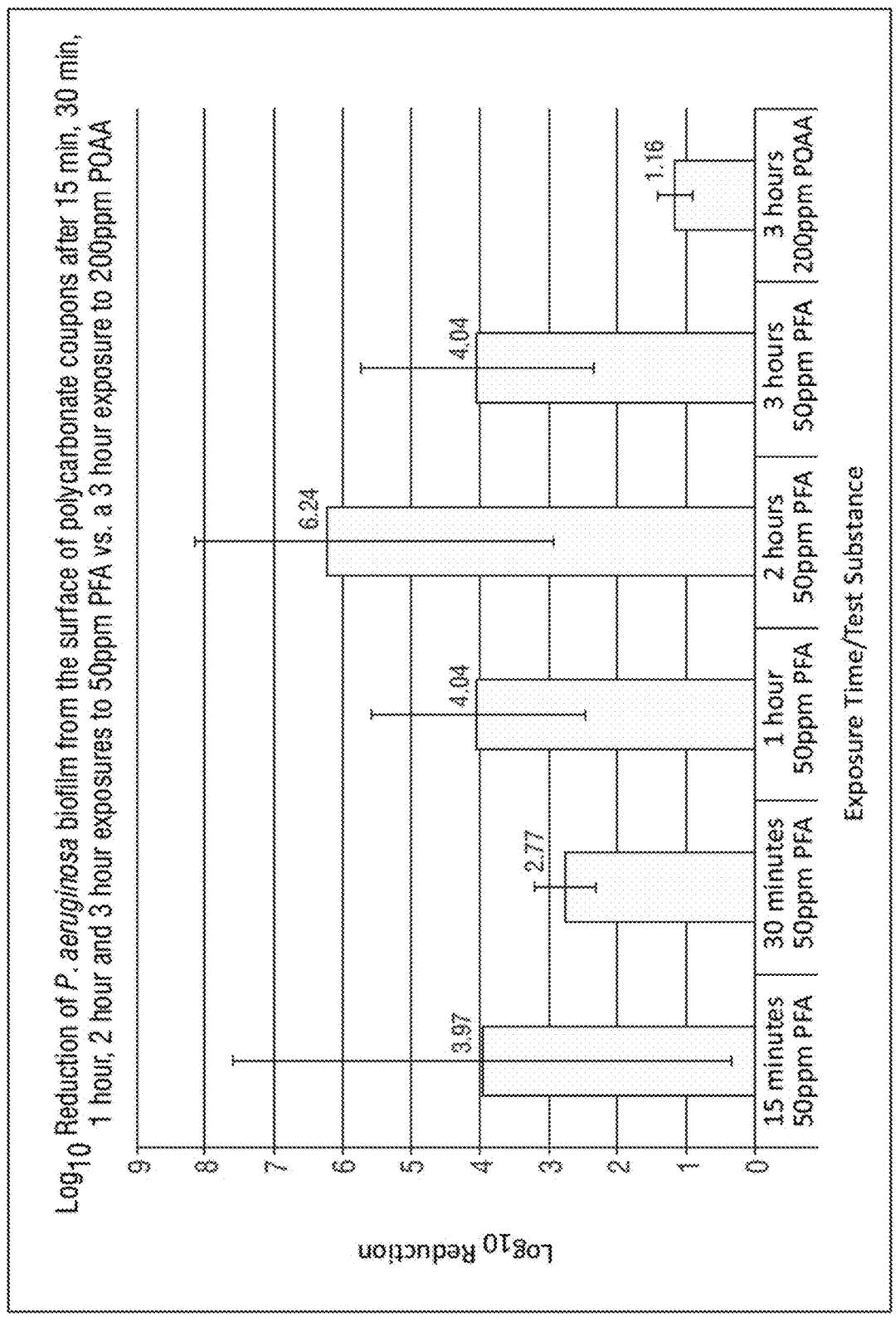
FIG. 12 illustrates reduction of *P. aeruginosa* biofilm using different exposure times of peroxyformic acid according to embodiments of the invention.

*P. aeruginosa* ATCC 15442 biofilm was grown on the surface of 24 polycarbonate coupons following ASTM method E2562-12: Standard Test Method for Quantification of *Pseudomonas aeruginosa* Biofilm Grown with High Shear and Continuous Flow using CDC Biofilm Reactor. After 48 hours of biofilm establishment, the coupons were removed from the reactor and placed into individual centrifuge tubes. Three coupons per test condition were tested for disinfectant efficacy using ASTM method E2871-12: Standard Test Method for Evaluating Disinfectant Efficacy against *Pseudomonas aeruginosa* Biofilm Grown in CDC Biofilm Reactor using Single Tube Method. Sets of three coupons were exposed to 4 mL of 50 ppm PFA for exposure times of 15 minutes, 30 minutes, 1 hour, 2 hours and 3 hours, while coupons treated with 200 ppm POAA were exposed for 3 hours only. After the desired exposure time, 16 mL of neutralizing medium was added on top of the chemistry to inactive antimicrobial performance. This was followed with a series of vortexing and sonicating steps to remove any biofilm from the coupon surface into the solution for plating and enumeration. As shown in FIG. 12, peroxyformic acid achieves greater anti-biofilm efficacy with shorter exposure time and lower concentrations than POAA.

Example 16. Stability of Glycerol Formates and Imidazole Premix

The accelerated stability of the premix of glycerol formates and pH adjustment reagent, i.e. imidazole was assessed by storing the premix in 40° C. oven over 6 weeks, and the properties of the premix was evaluated by the perhydrolysis with $H_2O_2$ under the same conditions. The composition of the premix as well as the perhydrolysis conditions are summarized in Table 12.

TABLE 12

Amount of Sugars and Formic Acid Used for the Synthesis of the Sugar Formates

| | Wt. % | |
|---|---|---|
| Compositions | Glycerol Formates (wt. %) | Imidazole (wt. %) |
| Premix | 97 | 3 |
| | 0.72 | |
| $H_2O_2$ | 0.70 | |
| DI water | 98.58 | |
| Total | 100 | |

Figure 13:
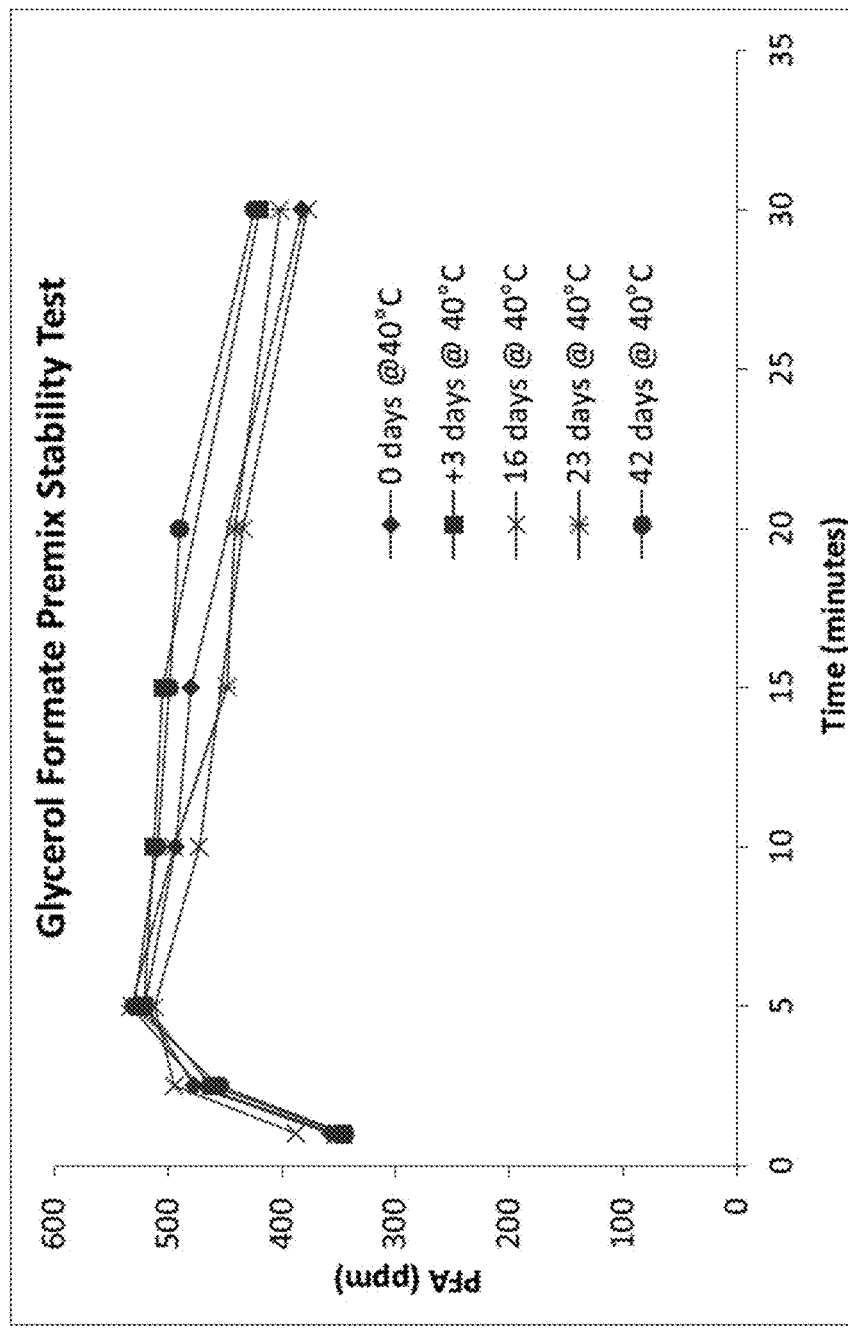
FIG. 13 illustrates the perhydrolysis kinetics of the glycerol premix stored for different periods demonstrating stability according to embodiments of the invention.

The perhydrolysis kinetics of the glycerol premix stored for different period of time is shown in FIG. 13 where under the accelerated storage conditions, there are effectively no differences among the glycerol formates premix stored up to 6 weeks.

Example 17. Generation of Performic Acid Through Perhydrolysis of Glycerol Formates Premix The generation of PFA from the perhydrolysis of glycerol formates and imidazole were evaluated under ambient conditions with various compositions, and the pH of the solution was also monitored as shown in Table 13 (GF—Glycerol formates; ID—Imidazole).

TABLE 13

Perhydrolysis Compositions of Glycerol Formates Premix

| | Composition A (wt. %) | | Composition B (wt. %) | | Composition C (wt. %) | | Composition D (wt. %) | |
|---|---|---|---|---|---|---|---|---|
| | GF (wt. %) | ID (wt. %) | GF (wt. %) | ID (wt. %) | GF (wt. %) | ID (wt. %) | GF (wt. %) | ID (wt. %) |
| Premix | 97.1 | 2.9 | 97.9 | 2.1 | 97.4 | 2.6 | 97.7 | 2.3 |
| | 0.72 | | 1.12 | | 0.92 | | 1.02 | |
| $H_2O_2$ | 0.70 | | 0.30 | | 0.30 | | 0.25 | |
| DI water | 98.58 | | 98.58 | | 98.78 | | 98.73 | |
| Total | 100 | | 100 | | 100 | | 100 | |

Figure 14:
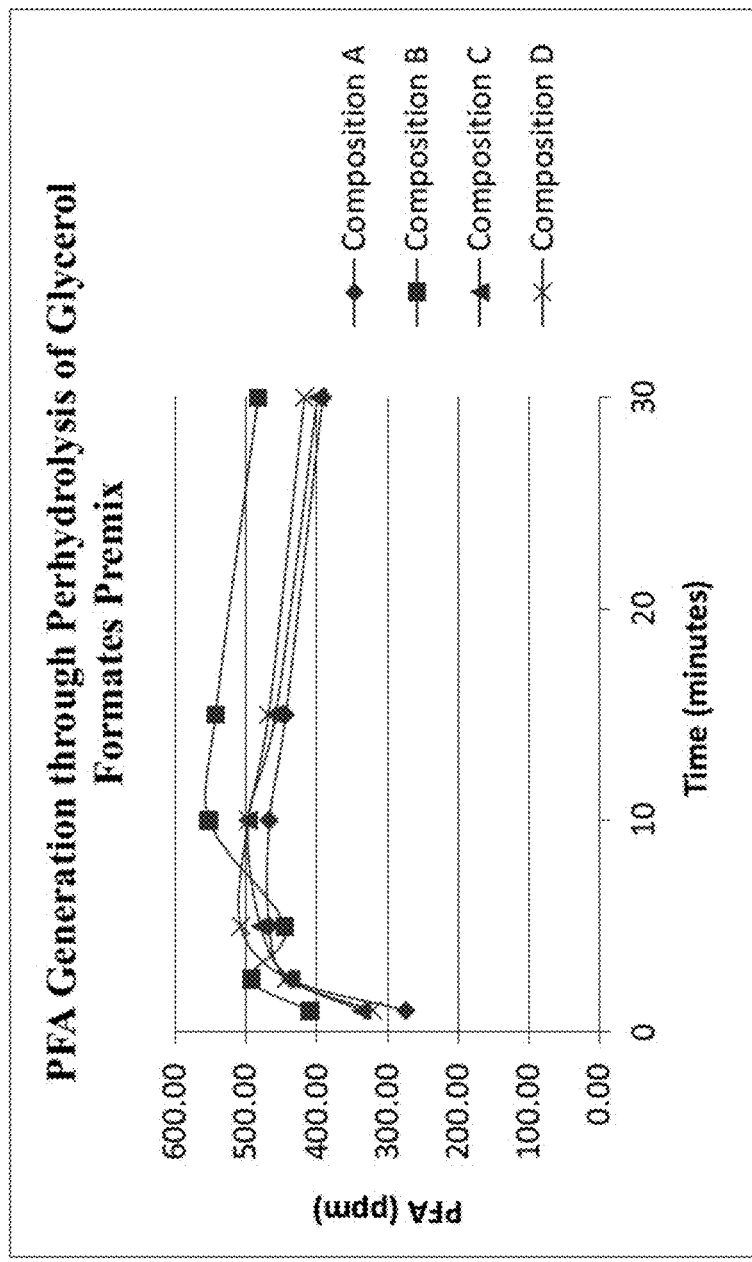
FIG. 14 illustrates peroxyformic acid generation through perhydrolysis of glycerol formate premixes according to embodiments of the invention.
Figure 15:
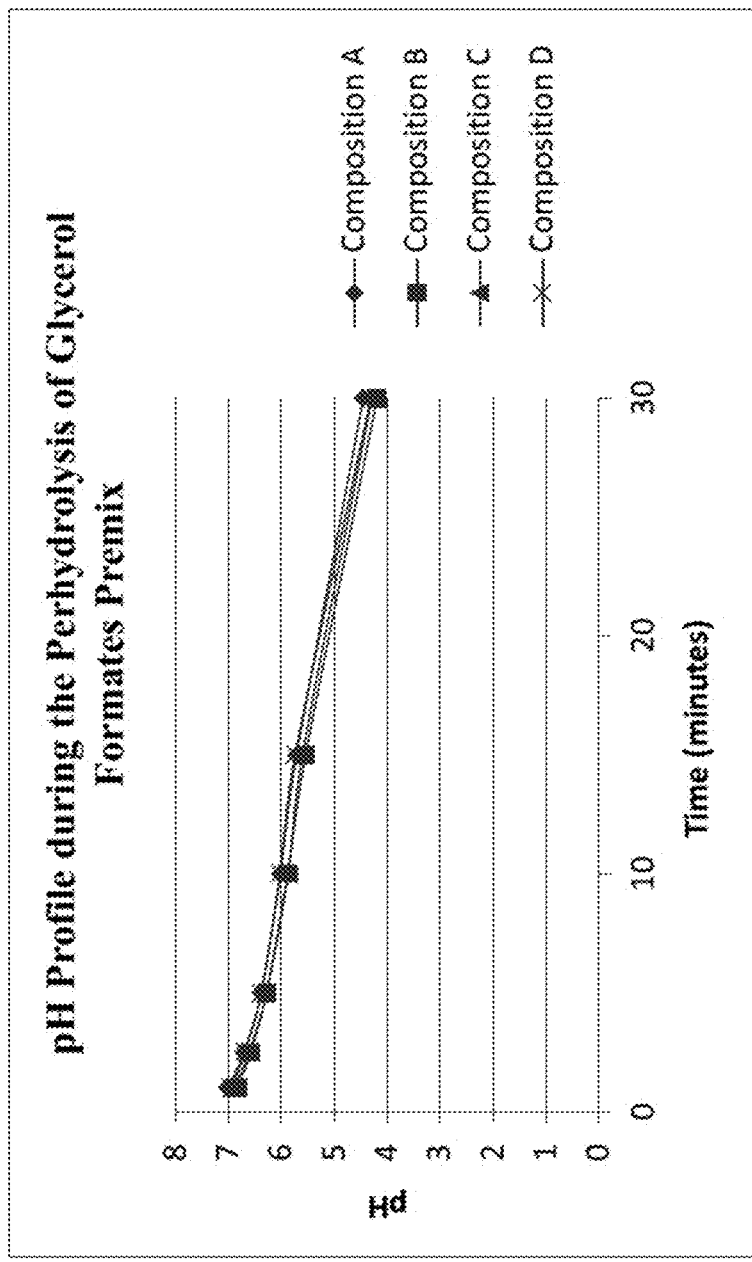
FIG. 15 illustrates the pH impact on peroxyformic acid generation through perhydrolysis of glycerol formate premixes according to embodiments of the invention.

FIGS. 14-15 show PFA is generated very quickly under mild pH conditions, which make the resulting compositions particularly suitable for treatment of surfaces or subjects requiring strong antimicrobial efficacy under more mild conditions, such as when non-corrosive antimicrobial efficacy is desired, e.g. surgical instruments, endoscopes, etc.

Example 18. Reduction of *E. coli* Using Different Performic-Acid Forming Compositions Nalidixic acid resistant *E. coli* O157:H7 was used to evaluate the efficacy in treatment with performic acid composition on raw beef brisket according to the conditions shown in Table 14.

TABLE 14

| Test Parameters | |
|---|---|
| Test System: | Nalidixic acid resistant *E. coli* O157:H7 |
| Test Substance Diluent: | Sterile DI Water buffered to pH 9.5 with sodium bicarbonate and carbonate |
| Red Meat: | Beef flank steak/brisket, cut into 5 cm square pieces |
| Inoculation: | 100 µl, spot inoculated and then spread with a sterile hockey stick |
| Attachment Time: | 1 hour at 4° C. |
| Treatment: | Dip for 10 minutes, allowing chemistry to drain off of meat for 15 seconds before neutralizing (3 samples a time) |
| Neutralizer: | 50 mL DE Broth |
| Recovery: | Stomached meat in neutralizer for 30 seconds at 230 rpm |
| Test Temperature | Ambient |
| Plating Medium: | TSA with nalidixic acid (1 ml/L media) |
| Incubation: | 35° C. for 48 hours |
| Notes: | Ester PFA turned meat white/gray during treatment |

The generation of PFA from the perhydrolysis of glycerol formates, PFA formulations, POAA formations and controls were evaluated as shown in Table 15.

TABLE 15

Chemistry Preparations

| | Formula | Test Concentration | Use-solution Preparation | Use-solution pH |
|---|---|---|---|---|
| A | POAA | 220 ppm POAA | 0.79 g Commercial POAA/ 500 g Total | 8.86 |
| B | POAA + LAS | 220 ppm POAA + 50 ppm LAS | 0.79 g Commercial POAA + 0.25 g 10% LAS/500 g Total | 8.88 |
| C | PFA | 180 ppm PFA | 0.95 g PFA/500 g Total | 8.76 |
| D | PFA + LAS | 180 ppm PFA + 50 ppm LAS | 0.95 g PFA + 0.25 g 10% LAS/500 g Total | 8.79 |
| E | Ester PFA (1% $H_2O_2$, 2% Ester) | 180 ppm PFA | 10 g Glycerol Formate + 10 g 50% $H_2O_2$/500 g Total | 6.61 |
| F | Ester PFA + LAS | 180 ppm PFA + 50 ppm LAS | 10 g Glycerol Formate + 10 g 50% $H_2O_2$ + 0.25 g 10% LAS/500 g Total | 6.66 |
| G | LAS | 50 ppm LAS | 0.25 g 10% LAS/500 g Total | 9.47 |
| H2O | DI Water buffered to pH 9.5 | | | 9.51 |
| No Treatment Background | | | | |

The micro results are shown in Tables 16-17, demonstrating improved micro efficacy (log reduction) achieved from PFA compositions in comparison to POAA.

| Test Substance | Exposure Time | Plate Count | Plate Dilution | CFU/ml | CFU/cm2 | Log CFU/cm2 | Standard Deviation | Average Log CFU/cm2 | Log Reduction |
|---|---|---|---|---|---|---|---|---|---|
| POAA | 10 minutes | 60 | 10 | 6.00E+02 | 1.20E+03 | 3.08 | 0.09 | 2.98 | 1.06 |
| 220 ppm POAA, pH 8.86 | | 45 | 10 | 4.50E+02 | 9.00E+02 | 2.95 | | | |
| | | 40 | 10 | 4.00E+02 | 8.00E+02 | 2.90 | | | |
| POAA + LAS | | 41 | 10 | 4.10E+02 | 8.20E+02 | 2.91 | 0.10 | 2.99 | 1.05 |
| 220 ppm POAA + 50 ppm LAS | | 63 | 10 | 6.30E+02 | 1.26E+03 | 3.10 | | | |
| pH 8.88 | | 45 | 10 | 4.50E+02 | 9.00E+02 | 2.95 | | | |
| PFA | | 92 | 10 | 9.20E+02 | 1.84E+03 | 3.26 | 0.06 | 3.22 | 0.83 |
| 180 ppm PFA, pH 8.76 | | 71 | 10 | 7.10E+02 | 1.42E+03 | 3.15 | | | |
| | | 86 | 10 | 8.60E+02 | 1.72E+03 | 3.24 | | | |
| PFA + LAS | | 103 | 10 | 1.03E+03 | 2.06E+03 | 3.31 | 0.04 | 3.29 | 0.76 |
| 180 ppm PFA + 50 ppm LAS | | 87 | 10 | 8.70E+02 | 1.74E+03 | 3.24 | | | |
| pH 8.79 | | 100 | 10 | 1.00E+03 | 2.00E+03 | 3.30 | | | |
| Ester PFA (1% $H_2O_2$, 2% | | 16 | 10 | 1.60E+02 | 3.20E+02 | 2.51 | 0.22 | 2.74 | 130 |
| Ester) | | 31 | 10 | 3.10E+02 | 6.20E+02 | 2.79 | | | |
| 180 ppm PFA, pH 6.61 | | 43 | 10 | 4.30E+02 | 8.60E+02 | 2.93 | | | |
| Ester PFA + LAS | | 26 | 10 | 2.60E+02 | 5.20E+02 | 2.72 | 0.26 | 2.71 | 1.33 |
| 180 ppm PFA + 50 ppm LAS | | 47 | 10 | 4.70E+02 | 9.40E+02 | 2.97 | | | |
| pH 6.66 | | 14 | 10 | 1.40E+02 | 2.80E+02 | 2.45 | | | |
| LAS | | 41 | 100 | 4.10E+03 | 8.20E+03 | 3.91 | 0.15 | 3.78 | 0.27 |
| 50 ppm LAS, pH 9.47 | | 31 | 100 | 3.10E+03 | 6.20E+03 | 3.79 | | | |
| | | 21 | 100 | 2.10E+03 | 4.20E+02 | 3.62 | | | |
| Water Control | | 27 | 100 | 2.70E+03 | 5.40E+03 | 3.73 | 0.06 | 3.80 | |
| DI $H_2O$ Buffered to pH 9.5 | | 33 | 100 | 3.30E+03 | 6.60E+03 | 3.82 | | | |
| | | 35 | 100 | 3.50E+03 | 7.00E+03 | 3.85 | | | |
| Non-treated Controls | | 61 | 100 | 6.10E+03 | 1.22E+04 | 4.09 | 0.06 | 4.04 | |
| | | 59 | 100 | 5.90E+03 | 1.18E+04 | 4.07 | | | |
| | | 47 | 100 | 4.70E+03 | 9.40E+03 | 3.97 | | | |
| Inoculum Numbers | | 42 | 100000 | 4.20E+06 | | | | | |
| | | 54 | 100000 | 5.40E+06 | | | | | |
| Background Numbers | | 25 | 10 | 2.50E+02 | | | | | |
| | | 46 | 10 | 4.60E+02 | | | | | |

TABLE 17

Micro Efficacy Results Summarized

| Test Substance | Log Reduction |
|---|---|
| POAA | 1.06 |
| 220 ppm POAA, pH 8.86 | |
| POAA + LAS | 1.05 |
| 220 ppm POAA + 50 ppm LAS | |
| pH 8.88 | |
| Ester PFA (1% $H_2O_2$, 2% Ester) | 1.30 |
| 180 ppm PFA, pH 6.61 | |
| Ester PFA + LAS | 1.33 |
| 180 ppm PFA + 50 ppm LAS | |
| pH 6.66 | |

As shown in the beneficially reduction of E. coli, the peroxyformic acid generated according to the methods of the invention provided an increase in micro efficacy over commercially available POAA and demonstrating suitable application of use of the chemistry for contacting food tissues with an alkaline PFA chemistry.

Example 19. Reduction of *Aspergillus brasilensis* (Anti-Fungal Activity) of Ester PFA

*Aspergillus brasilensis* ATCC 16403 was used to evaluate the efficacy in treatment with performic acid compositions according to the conditions shown in Table 18.

TABLE 18

Test Parameters

| | |
|---|---|
| Test Systems: | *Aspergillus brasiliensis* ATCC 16403 |
| Test Substances: | Ester PFA - Target 440 ppm PFA |
| | Ester PFA - Target 500 ppm PFA |
| Test Substance Diluent: | EN Synthetic Hard Water, pH 7.05 |
| Interferring Substance: | Dirty Conditions Bovine Albumin Solution (3 g/L) + sheep erythrocytes |
| Exposure Time(s): | 5 minutes and 10 minutes |
| Neutralizer: | 8 mL DE Broth + 1 mL sterile water |
| Test Temperature: | 20° C. |
| Plating Medium: | Oxoid MEA |
| Incubation: | 30° C. for 72 hours |

Figure 16:
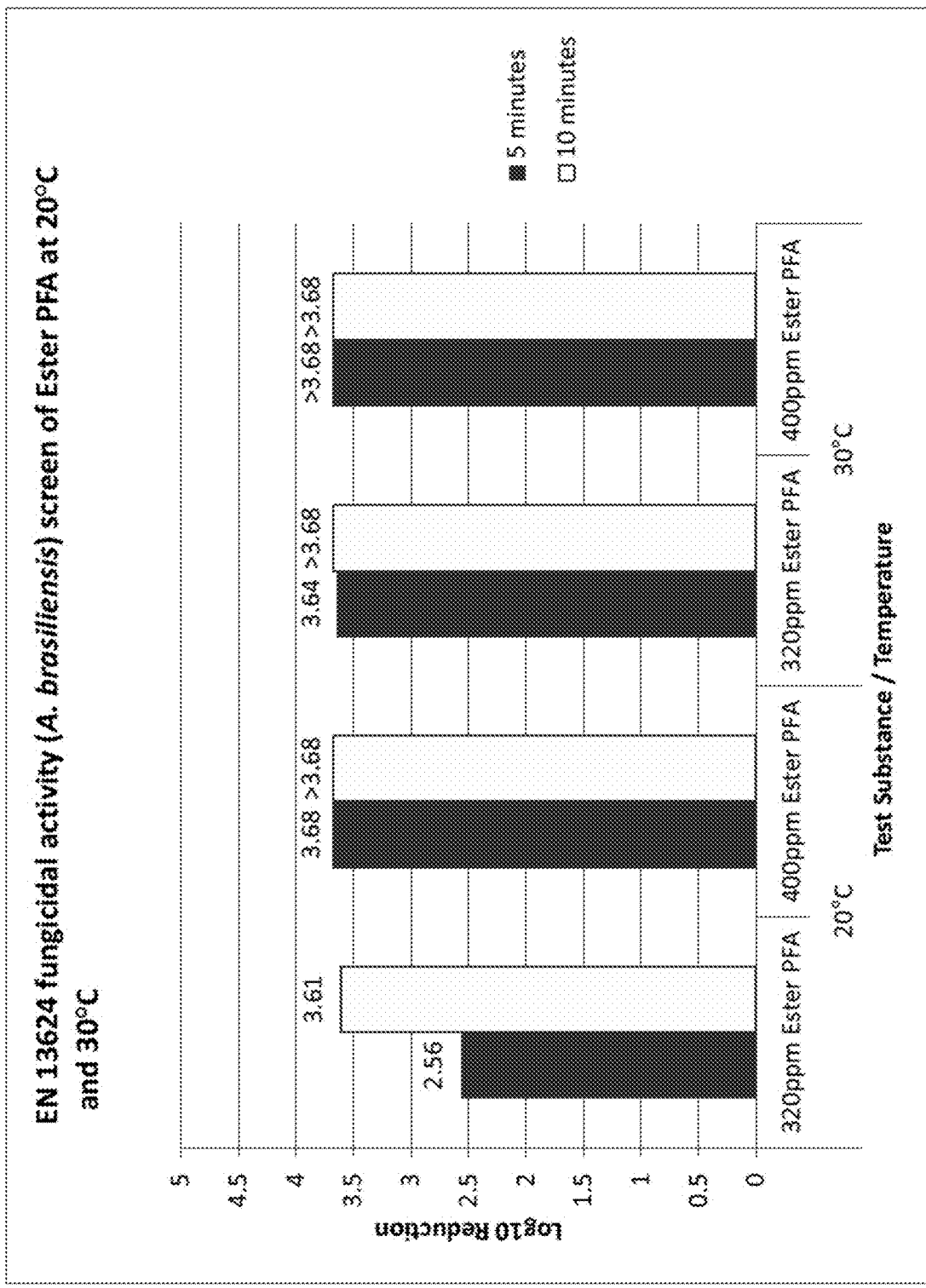
FIG. 16 illustrates improved micro efficacy (log reduction) achieved from peroxyformic acid compositions in comparison to peroxyacetic acid according to embodiments of the invention.

The ester PFA compositions at varying ppm concentrations were evaluated as shown in Table 19, with the micro results further shown in FIG. 16, demonstrating improved micro efficacy (log reduction) achieved from PFA compositions in comparison to POAA.

TABLE 19

Micro Efficacy Results

| Test Substance | Test Temperature | Exposure Time | Log$_{10}$ Growth | Log$_{10}$ Reduction |
|---|---|---|---|---|
| Ester PFA | 20° C. | 5 minutes | 3.27 | 2.57 |
| 320 ppm PFA | | 10 minutes | 2.22 | 3.61 |
| Ester PFA | | 5 minutes | <2.15 | >3.68 |
| 400 ppm PFA | | 10 minutes | <2.15 | >3.68 |
| Ester PFA | 30 C. | 5 minutes | 2.19 | 3.64 |
| 320 ppm PFA | | 10 minutes | <2.15 | >3.68 |
| Ester PFA | | 5 minutes | 1.48 | 4.36 |

TABLE 19-continued

Micro Efficacy Results

| Test Substance | Test Temperature | Exposure Time | Log$_{10}$ Growth | Log$_{10}$ Reduction |
|---|---|---|---|---|
| 400 ppm PFA | | 10 minutes | <2.15 | >3.68 |
| Test Mixture Inoculum Numbers (N$_o$) | | | 5.83 | |
| *Aspergillus brasiliensis* ATCC 16404 | | | 6.83 | |
| Test Suspension Numbers (N) | | | | |

Example 20. Fungicidal and Sporicidal Activity of Ester PFA

Various *Bacillus* and *Aspergillus* pathogens were used to evaluate the micro efficacy of ester PFA generated according to methods of the present invention. The test method, substance and results showing micro efficacy of the PFA compositions are shown in Tables 20-23.

TABLE 20

Micro Efficacy Test Parameters and Results

| Test Substance | Test Temperature | Exposure Time | Organic Soil | Log$_{10}$ Growth | Log$_{10}$ Reduction |
|---|---|---|---|---|---|
| 350 ppm PFA pH 5.88 | 35° C. | 5 minutes | Dirty Conditions (high concentration bovine albumin solution + sheep erythrocytes) | <2.18 | >3.91 |
| 300 ppm PFA pH 5.91 | | | | <2.18 | >3.91 |
| 250 ppm PFA pH 5.82 | | | | <2.18 | >3.91 |
| 200 ppm PFA pH 5.81 | | | | <2.18 | >3.91 |
| Test Mixture Inoculum Numbers (N$_o$) | | | | 6.09 | |
| *Bacillus subtilis* ATCC 6633 | | | | 7.09 | |
| Test Suspension Numbers (N) | | | | | |

TABLE 21

Micro Efficacy Test Parameters and Results

| Test Substance | Test Temperature | Exposure Time | Organic Soil | Log$_{10}$ Growth | Log$_{10}$ Reduction |
|---|---|---|---|---|---|
| 350 ppm PFA pH 5.88 | 35° C. | 5 minutes | Dirty Conditions (high concentration bovine albumin solution + sheep erythrocytes) | <2.18 | >3.87 |
| 300 ppm PFA pH 5.91 | | | | <2.18 | >3.87 |
| 250 ppm PFA pH 5.82 | | | | <2.18 | >3.87 |
| 200 ppm PFA pH 5.81 | | | | <2.18 | >3.87 |
| Test Mixture Inoculum Numbers (N$_o$) | | | | 6.05 | |
| *Bacillus subtilis* ATCC 19659 | | | | 7.05 | |
| Test Suspension Numbers (N) | | | | | |

TABLE 22

Micro Efficacy Test Parameters and Results

| Test Substance | Test Temperature | Exposure Time | Organic Soil | Log$_{10}$ Growth | Log$_{10}$ Reduction |
|---|---|---|---|---|---|
| 350 ppm PFA pH 5.88 | 35° C. | 5 minutes | Dirty Conditions (high concentration bovine albumin | 3.46 | 2.65 |
| 300 ppm PFA pH 5.91 | | | | 3.38 | 2.73 |
| 250 ppm PFA pH 5.82 | | | | 3.55 | 2.56 |
| 200 ppm PFA pH 5.81 | | | | >4.22 | <1.89 |

TABLE 22-continued

Micro Efficacy Test Parameters and Results

| Test Substance | Test Temperature | Exposure Time | Organic Soil | Log$_{10}$ Growth | Log$_{10}$ Reduction |
|---|---|---|---|---|---|
| | | | solution + sheep erythrocytes) | | |
| Test Mixture Inoculum Numbers (N$_o$) | | | | 6.11 | |
| *Aspergillus brasiliensis* ATCC 16404 Test Suspension Numbers (N) | | | | 7.11 | |

TABLE 23

Micro Efficacy Test Parameters and Results

| Test Substance | Test Temperature | Exposure Time | Organic Soil | Log$_{10}$ Growth | Log$_{10}$ Reduction |
|---|---|---|---|---|---|
| 350 ppm PFA Ester PFA pH | 35° C. | 5 minutes | Dirty Conditions (high concentration bovine albumin solution + sheep erythrocytes) | 2.23 | 3.91 |
| 300 ppm PFA Ester PFA pH | | | | 3.87 | 2.26 |
| Test Mixture Inoculum Numbers (N$_o$) | | | | 6.14 | |
| *Aspergillus brasiliensis* ATCC 16404 Test Suspension Numbers (N) | | | | 7.14 | |

Example 21. Sporicidal Activity of Ester PFA Versus POAA

*Bacillus* pathogens were used to evaluate the micro efficacy of ester PFA generated according to methods of the present invention in comparison to POAA. The test methods are shown in Table 24 and the results are shown in Table 25 and FIG. 17.

TABLE 24

Test Parameters

| | |
|---|---|
| Test Systems: | *Bacillus subitilis* ATCC 19659 |
| Test Substances: | PFA (5.45% PFA) |
| | POAA (14.89% POAA) |
| Test Substance Diluent: | EN Synthetic Hard Water, pH 7.03 |
| Test Substance Dilutions: | 300 ppm PFA pH 6.84 |
| | 400 ppm PFA pH 7.19 |
| | 368 ppm POAA (molar equivalent to 300 ppm PFA) pH 6.73 |
| | 490 ppm POAA (molar equivalent to 400 ppm PFA) pH 6.78 |
| Interferring Substance: | Dirty Conditions Bovine Albumin Solution (3 g/L) + sheep erythrocytes |
| Exposure Time(s): | 5 minutes, 10 minutes |
| Neutralizer: | 8 mL DE Broth + 1 mL sterile water |
| Test Temperature: | 20° C. |
| Plating Medium: | Oxoid TSA |
| Incubation: | 30° C. for 72 hours |

TABLE 25

Results

| Test Substance | Exposure Time | Organic Soil | Average CFU/mL | Log$_{10}$ Growth | Log$_{10}$ Reduction |
|---|---|---|---|---|---|
| 300 ppm PFA pH 6.84 | 5 minutes | Dirty Conditions (high concentration bovine albumin solution + sheep erythrocytes) | 3.25E+03 | 3.51 | 2.28 |
| | 10 minutes | | 4.50E+01 | 1.65 | 4.14 |
| 400 ppm PFA pH 7.19 | 5 minutes | | 3.45E+03 | 3.54 | 2.26 |
| | 10 minutes | | 1.30E+03 | 3.11 | 2.68 |
| 368 ppm POAA pH 6.73 | 5 minutes | | 7.50E+05 | 5.88 | 0.00 |
| | 10 minutes | | 5.00E+05 | 5.70 | 0.00 |

TABLE 25-continued

| | | Results | | | |
|---|---|---|---|---|---|
| Test Substance | Exposure Time | Organic Soil | Average CFU/mL | $\text{Log}_{10}$ Growth | $\text{Log}_{10}$ Reduction |
| 490 ppm POAA | 5 minutes | | 8.50E+05 | 5.93 | 0.00 |
| pH 6.78 | 10 minutes | | 4.00E+05 | 5.60 | 0.19 |
| Test Mixture Inoculum Numbers (N/10) | | | 6.23E+05 | 5.79 | |
| *Bacillus subtilis* ATCC 19659 | | | 6.23E+06 | 6.79 | |
| Test Suspension Numbers (N) | | | | | |
| Validation Test Suspension Numbers ($N_v$) | | | 1.90E+02 | | |
| Control Mixture Inoculum Numbers ($N_{vo}$) | | | 1.90E+01 | | |
| Control A | | Dirty Conditions | 1.60E+01 | | |
| Control B | | | 1.50E+01 | | |
| Control C - PFA | | Dirty | 1.70E+01 | | |
| Control C - POAA | | Conditions | 1.50E+01 | | |

Figure 17:
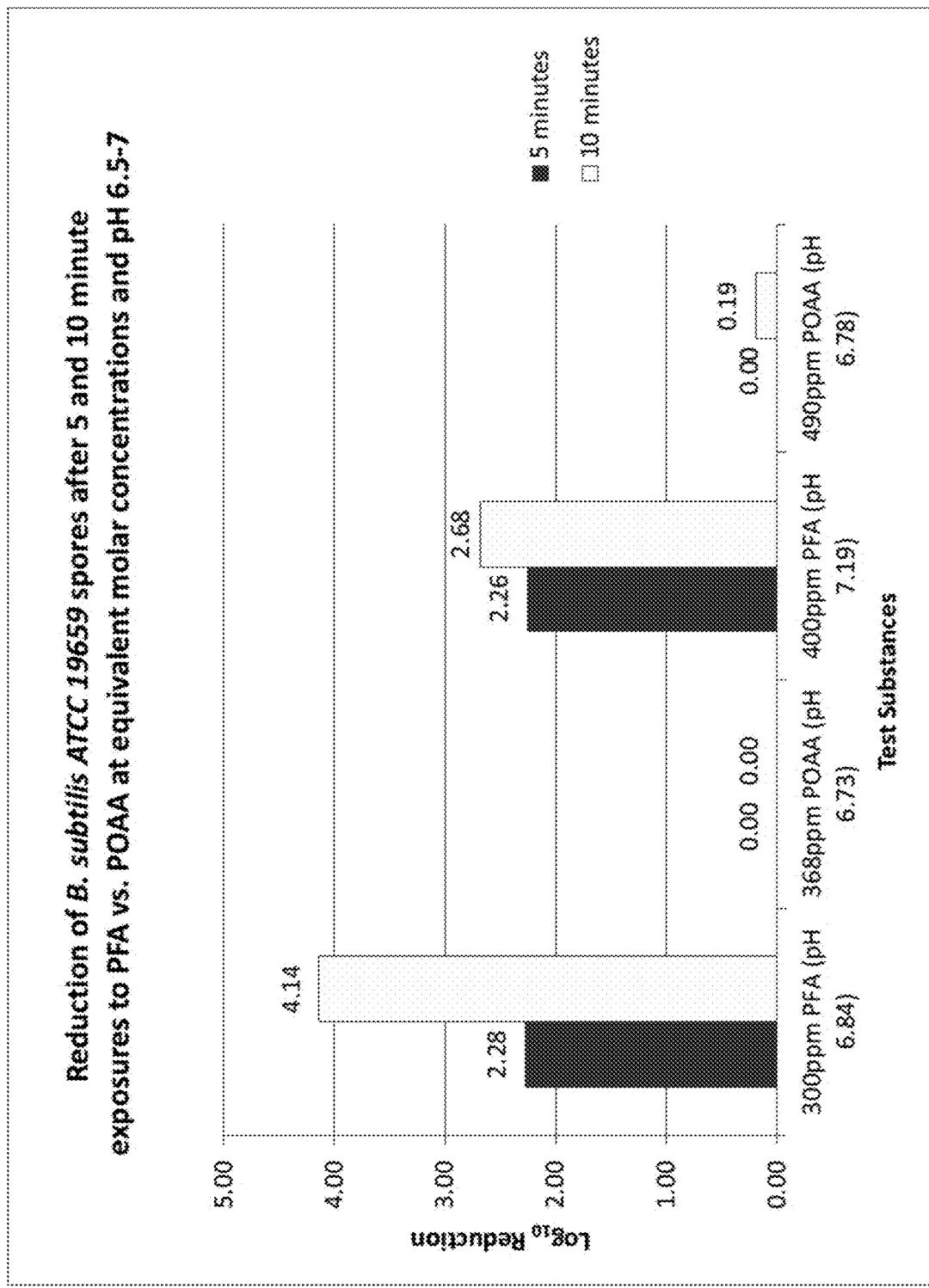
FIG. 17 illustrates improved micro efficacy (log reduction) achieved from peroxyformic acid compositions in comparison to peroxyacetic acid according to embodiments of the invention.

As shown in FIG. 17 the PFA compositions generated according to the methods of the invention provide increased reduction in *B. subtillis* spores at both 5 and 10 minutes and at lower concentrations than POAA chemistries.

Example 22. Fungicidal/Yeasticidal Activity of Ester PFA Versus POAA

*Canidia* and *Aspergillus* pathogens were used to evaluate the micro efficacy of ester PFA generated according to methods of the present invention in comparison to POAA. The test methods are shown in Table 26 and the results are shown in Tables 27-28 and FIGS. 18-19.

TABLE 26

| Test Parameters | |
|---|---|
| Test Systems: | *Candida albicans* ATCC 10231 |
| | *Aspergillus brasiliensis* ATCC 16404 |

TABLE 26-continued

| Test Parameters | |
|---|---|
| Test Substances: | PFA (9.48% PFA) |
| | POAA (14.95% POAA) |
| Test Substance Diluent: | EN Synthetic Hard Water, pH 7.04 |
| Test Substance Dilutions: | 200 ppm PFA pH 6.15 |
| | 300 ppm PFA pH 6.21 |
| | 245 ppm POAA (molar equivalent to 200 ppm PFA) pH 6.56 |
| | 368 ppm POAA (molar equivalent to 300 ppm PFA) pH 6.63 |
| Interfering Substance: | Dirty Conditions Bovine Albumin Solution (3 g/L) + sheep erythrocytes |
| Exposure Time(s): | 5 minutes, 10 minutes, 15 minutes |
| Neutralizer: | 8 mL DE Broth + 1 mL sterile water |
| Test Temperature: | 20° C. |
| Plating Medium: | Oxoid MEA |
| Incubation: | 30° C. for 48 hours |

TABLE 27

| | | Results (*Candida albicans*) | | | |
|---|---|---|---|---|---|
| Test Substance | Exposure Time | Organic Soil | Average CFU/mL | $\text{Log}_{10}$ Growth | $\text{Log}_{10}$ Reduction |
| 200 ppm PFA | 5 minutes | Dirty | <140 | <2.15 | >4.14 |
| pH 6.15 | 10 minutes | Conditions (high | <140 | <2.15 | >4.14 |
| | 15 minutes | concentration bovine | <140 | <2.15 | >4.14 |
| 300 ppm PFA | 5 minutes | albumin | <140 | <2.15 | >4.14 |
| pH 6.21 | 10 minutes | solution + sheep | <140 | <2.15 | >4.14 |
| 245 ppm POAA | 5 minutes | erythrocytes) | <140 | <2.15 | >4.14 |
| pH 6.56 | 10 minutes | | <140 | <2.15 | >4.14 |
| | 15 minutes | | <140 | <2.15 | >4.14 |
| 368 ppm POAA | 5 minutes | | <140 | <2.15 | >4.14 |
| pH 6.63 | 10 minutes | | <140 | <2.15 | >4.14 |
| Test Mixture Inoculum Numbers ($N_o$) | | | 1.94E+06 | 6.29 | |
| *Candida albicans* ATCC 10231 | | | 1.94E+07 | 7.29 | |
| Test Suspension Numbers (N) | | | | | |
| Validation Test Suspension Numbers ($N_v$) | | | 5.55E+02 | | |
| Control Mixture Inoculum Numbers ($N_{vo}$) | | | 5.55E+01 | | |
| Control A | | Dirty Conditions | 4.70E+01 | | |
| Control B | | | 5.20E+01 | | |
| Control C | | Dirty Conditions | 4.80E+01 | | |

TABLE 28

Results (*Aspergillus brasiliensis*)

| Test Substance | Exposure Time | Organic Soil | Average CFU/mL | $\text{Log}_{10}$ Growth | $\text{Log}_{10}$ Reduction |
|---|---|---|---|---|---|
| 200 ppm PFA pH 6.15 | 5 minutes | Dirty Conditions (high concentration bovine albumin solution + sheep erythrocytes) | 1.60E+04 | 4.20 | 1.54 |
|  | 10 minutes |  | 1.75E+03 | 3.24 | 2.50 |
|  | 15 minutes |  | 3.85E+02 | 2.59 | 3.16 |
| 300 ppm PFA pH 6.21 | 5 minutes |  | 4.10E+02 | 2.61 | 3.13 |
|  | 10 minutes |  | 1.20E+02 | 2.08 | 3.67 |
| 245 ppm POAA pH 6.56 | 5 minutes |  | >1.65E+05 | >5.22 | <0.53 |
|  | 10 minutes |  | >1.65E+05 | >5.22 | <0.53 |
|  | 15 minutes |  | >1.65E+05 | >5.22 | <0.53 |
| 368 ppm POAA pH 6.63 | 5 minutes |  | >1.65E+05 | >5.22 | <0.53 |
|  | 10 minutes |  | >1.65E+05 | >5.22 | <0.53 |
| Test Mixture Inoculum Numbers ($N_o$) |  |  | 5.59E+05 | 5.75 |  |
| *Aspergillus brasiliensis* ATCC 16404 Test Suspension Numbers (N) |  |  | 5.59E+06 | 6.75 |  |
| Validation Test Suspension Numbers ($N_v$) |  |  | 1.45E+02 |  |  |
| Control Mixture Inoculum Numbers ($N_{vo}$) |  |  | 1.45E+01 |  |  |

Figure 18:
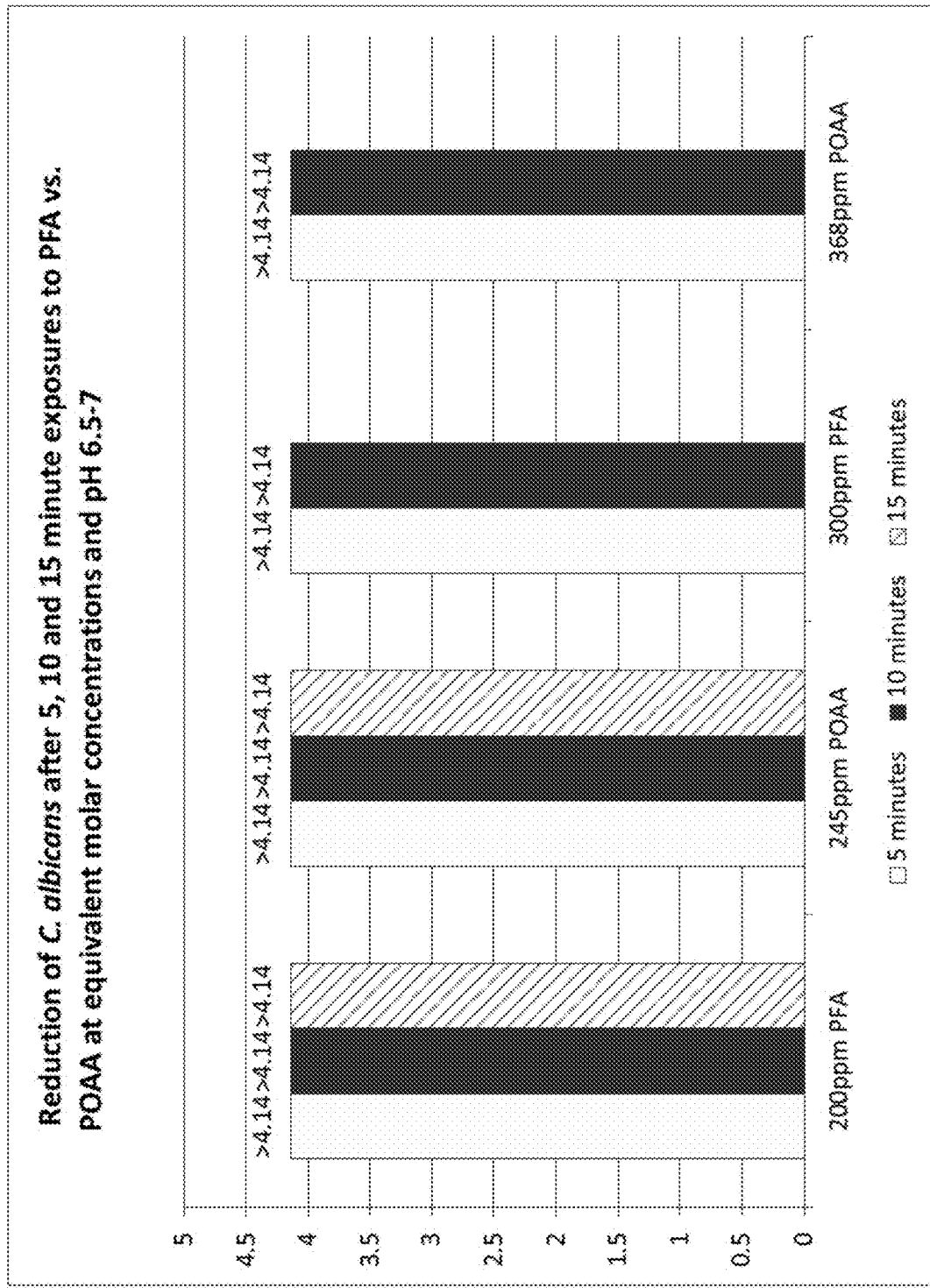
FIG. 18 illustrates equivalent micro efficacy (log reduction) achieved for spores from peroxyformic acid compositions in comparison to peroxyacetic acid (when dosed at lower actives) according to embodiments of the invention.

As shown in FIG. 18 the PFA compositions generated according to the methods of the invention provide equivalent reduction in *C. albicans* at 5, 10 and 15 minutes as POAA chemistries even when dosed at lower actives.

Figure 19:
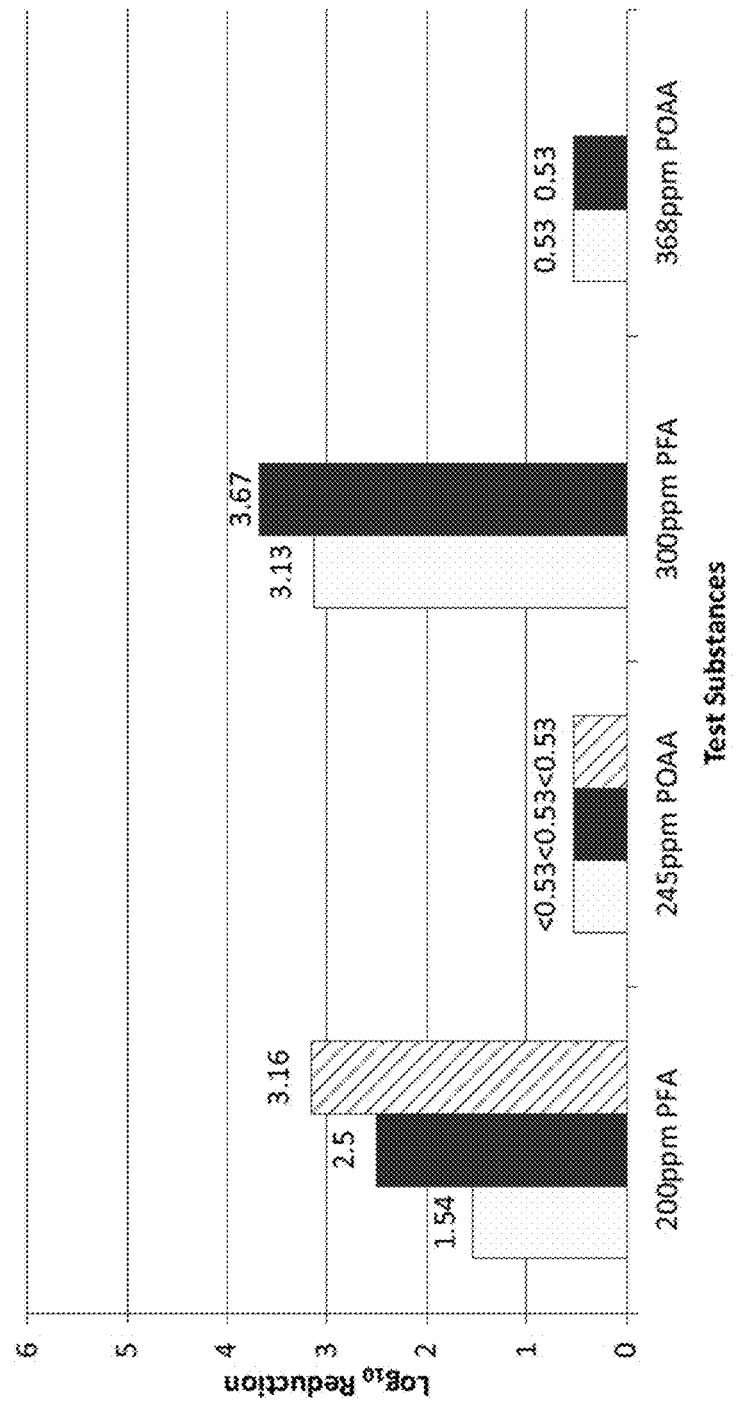
FIG. 19 illustrates improved micro efficacy (log reduction) achieved for spores from peroxyformic acid compositions in comparison to peroxyacetic acid according to embodiments of the invention.

As shown in FIG. 19 the PFA compositions generated according to the methods of the invention provide improved reduction in *A. brasiliensis* conidio spores at 5, 10 and 15 minutes as POAA chemistries even when dosed at lower actives.

Example 23. Sporicidal Activity of Ester PFA Versus POAA

Additional *Bacillus* pathogens were used to evaluate the micro efficacy of ester PFA generated according to methods of the present invention in comparison to POAA. The test methods are shown in Table 29 and the results are shown in Table 30.

TABLE 29

Test Parameters

| | |
|---|---|
| Test Systems: | *Bacillus subitilis* ATCC 19659 |
| Test Substances: | PFA (5.6% PFA) |
|  | POAA (14.98% POAA) |
| Test Substance Diluent: | EN Synthetic Hard Water, pH 7.09 |
| Test Substance Dilutions: | 300 ppm PFA pH 6.73 |
|  | 400 ppm PFA pH 6.95 |
|  | 368 ppm POAA (molar equivalent to 300 ppm PFA) pH 6.88 |
|  | 490 ppm POAA (molar equivalent to 400 ppm PFA) pH 6.65 |
| Interferring Substance: | Dirty Conditions Bovine Albumin Solution (3 g/L) + sheep erythrocytes |
| Exposure Time(s): | 5 minutes, 10 minutes |
| Neutralizer: | 8 mL DE Broth + 1 mL sterile water |
| Test Temperature: | 20° C. |
| Plating Medium: | Oxoid TSA |
| Incubation: | 30° C. for 72 hours |

TABLE 30

Results

| Test Substance | Exposure Time | Organic Soil | Average CFU/mL | $\text{Log}_{10}$ Growth | $\text{Log}_{10}$ Reduction |
|---|---|---|---|---|---|
| 300 ppm PFA pH 6.73 | 5 minutes | Dirty Conditions (high concentration bovine albumin solution + sheep erythrocytes) | >3.0E+05 | >5.48 | <2.26 |
|  | 10 minutes |  | 1.28E+05 | 5.11 | 2.63 |
| 400 ppm PFA pH 6.95 | 5 minutes |  | >3.0E+05 | >5.48 | <2.26 |
|  | 10 minutes |  | 7.50E+04 | 4.88 | 2.86 |
| 368 ppm POAA pH 6.88 | 5 minutes |  | >3.0E+06 | >6.48 | <1.26 |
|  | 10 minutes |  | >3.0E+05 | >5.48 | <2.26 |
| 490 ppm POAA pH 6.65 | 5 minutes |  | >3.0E+06 | >6.48 | <1.26 |
|  | 10 minutes |  | >3.0E+05 | >5.48 | <2.26 |
| *Bacillus subtilis* ATCC 19659 Test Suspension Numbers (N) |  |  | 5.45E+07 | >7.74 |  |
| Validation Test Suspension Numbers ($N_v$) |  |  |  |  |  |
| Control Mixture Inoculum Numbers ($N_{vo}$) |  |  |  |  |  |
| Control A |  | Dirty Conditions |  |  |  |
| Control B |  |  |  |  |  |
| Control C |  | Dirty Conditions |  |  |  |

Example 24. Bactericidal Activity of Ester PFA Versus POAA

Additional *Staphylococcus, Enterococcus* and *Pseudomonas* pathogens were used to evaluate the micro efficacy of ester PFA generated according to methods of the present invention in comparison to POAA. The test methods are shown in Table 31 and the results are shown in Tables 32-35 and FIG. 20.

TABLE 31

| Test Parameters | |
|---|---|
| Test Systems: | *Staphylococcus aureus* ATCC 6538 (0.217 A @ 620 nm) |
| | *Enterococcus hirae* ATCC 10541 (0.184 A @ 620 nm) |
| | *Pseudomonas aeruginosa* ATCC 15442 (0.191 A @ 620 nm) |
| Test Substances: | PFA (9.86% PFA) |
| | POAA (14.95% POAA) |
| Test Substance Diluent: | EN Synthetic Hard Water, pH 7.04 |
| Test Substance Dilutions: | 20 ppm PFA      pH 6.61 |
| | 30 ppm PFA      pH 6.74 |
| | 50 ppm PFA      pH 6.60 |
| | 25 ppm POAA (molar equivalent to 20 ppm PFA) pH 6.73 |
| | 38 ppm POAA (molar equivalent to 30 ppm PFA) pH 6.74 |
| | 62 ppm POAA (molar equivalent to 50 ppm PFA) pH 6.98 |
| Interferring Substance: | Dirty Conditions Bovine Albumin Solution (3 g/L) + sheep erythrocytes |
| Exposure Time(s): | 5 minutes |
| Neutralizer: | 8 mL DE Broth + 1 mL sterile water |
| Test Temperature: | 20° C. |
| Plating Medium: | Oxoid TSA |
| Incubation: | 35° C. for 48 hours |

TABLE 32

| Results | | | | | |
|---|---|---|---|---|---|
| Test Substance | Exposure Time | Organic Soil | Average CFU/mL | $Log_{10}$ Growth | $Log_{10}$ Reduction |
| 20 ppm PFA pH 6.61 | 5 minutes | Dirty Conditions (High concentration Bovine Albumin Solution + sheep erythrocytes) | <140 | <2.15 | >5.15 |
| 30 ppm PFA pH 6.74 | | | <140 | <2.15 | >5.15 |
| 50 ppm PFA pH 6.60 | | | <140 | <2.15 | >5.15 |
| 24.8 ppm POAA pH 6.73 | | | 1.77E+05 | 5.25 | 2.05 |
| 37.6 ppm POAA pH 6.90 | | | <140 | <2.15 | >5.15 |
| 62.4 ppm POAA pH 6.98 | | | <140 | <2.15 | >5.15 |
| Test Mixture Inoculum Numbers ($N_o$) | | | 1.97E+07 | 7.30 | |
| *S. aureus* ATCC 6538 | | | 1.97E+08 | | |
| Test Suspension Numbers (N) | | | | | |
| Validation Test Suspension Numbers ($N_v$) | | | 5.70E+02 | | |
| Control Mixture Inoculum Numbers ($N_{vo}$) | | | 5.70E+01 | | |
| Control A | | Dirty Conditions | 5.60E+01 | | |
| Control B | | | 7.40E+01 | | |
| Control C-A | | Dirty Conditions | 5.90E+01 | | |
| Control C-B | | | 6.00E+01 | | |

TABLE 33

| Results | | | | | |
|---|---|---|---|---|---|
| Test Substance | Exposure Time | Organic Soil | Average CFU/mL | $Log_{10}$ Growth | $Log_{10}$ Reduction |
| 20 ppm PFA pH 6.61 | 5 minutes | Dirty Conditions (High concentration Bovine Albumin | 6.30E+03 | 3.80 | 3.46 |
| 30 ppm PFA pH 6.74 | | | 2.15E+02 | 2.33 | 4.92 |
| 50 ppm PFA pH 6.60 | | | <140 | <2.15 | >5.10 |

TABLE 33-continued

| | | Results | | | |
|---|---|---|---|---|---|
| Test Substance | Exposure Time | Organic Soil | Average CFU/mL | $Log_{10}$ Growth | $Log_{10}$ Reduction |
| 24.8 ppm POAA pH 6.73 | | Solution + sheep erythrocytes) | >3.30E+05 | >5.52 | <1.74 |
| 37.6 ppm POAA pH 6.90 | | | 9.25E+03 | 3.97 | 3.29 |
| 62.4 ppm POAA pH 6.98 | | | <140 | <2.15 | >5.10 |
| Test Mixture Inoculum Numbers ($N_o$) | | | 1.80E+07 | 7.26 | |
| *E. hirae* ATCC 10541 Test Suspension Numbers | | | 1.80E+08 | | |
| Validation Test Suspension Numbers ($N_v$) | | | 4.30E+02 | | |
| Control Mixture Inoculum Numbers ($N_{vo}$) | | | 4.30E+01 | | |
| Control A | | Dirty Conditions | 7.70E+01 | | |
| Control B | | | 6.60E+01 | | |
| Control C-A | | Dirty Conditions | 4.60E+01 | | |
| Control C-B | | | 5.30E+01 | | |

TABLE 34

| | | Results | | | |
|---|---|---|---|---|---|
| Test Substance | Exposure Time | Organic Soil | Average CFU/mL | $Log_{10}$ Growth | $Log_{10}$ Reduction |
| 20 ppm PFA pH 6.61 | 5 minutes | Dirty Conditions | <140 | <2.15 | >5.22 |
| 30 ppm PFA pH 6.74 | | (High concentration | <140 | <2.15 | >5.22 |
| 50 ppm PFA pH 6.60 | | Bovine Albumin | <140 | <2.15 | >5.22 |
| 24.8 ppm POAA pH 6.73 | | Solution + sheep erythrocytes) | <140 | <2.15 | >5.22 |
| 37.6 ppm POAA pH 6.90 | | | <140 | <2.15 | >5.22 |
| 62.4 ppm POAA pH 6.98 | | | <140 | <2.15 | >5.22 |
| Test Mixture Inoculum Numbers ($N_o$) | | | 2.35E+07 | 7.37 | |
| *P. aeruginosa* ATCC 15442 Test Suspension Numbers | | | 2.35E+08 | | |
| Validation Test Suspension Numbers ($N_v$) | | | 5.05E+02 | | |
| Control Mixture Inoculum Numbers ($N_{vo}$) | | | 5.05E+01 | | |
| Control A | | Dirty Conditions | 8.40E+01 | | |
| Control B | | | 9.00E+01 | | |
| Control C-A | | Dirty Conditions | 5.50E+01 | | |
| Control C-B | | | 4.30E+01 | | |

TABLE 35

| | Passing Requirements & Results | | |
|---|---|---|---|
| Passing Requirements per EN 1276: | *S. aureus* | *E. hirae* | *P. aeruginosa* |
| N is between $1.5 \times 10^8$ CFU/mL and $5.0 \times 10^8$ CFU/mL | N = $1.97 \times 10^8$ | N = $1.80 \times 10^8$ | N = $2.35 \times 10^8$ |
| $N_{vo}$ is between 30 and 160 CFU/mL | $N_{vo}$ = 57 | $N_{vo}$ = 43 | $N_{vo}$ = 51 |
| Controls A, B, C are equal to or greater than $0.5 \times N_{vo}$ | YES | YES | YES |
| A greater than 5 $log_{10}$ reduction (R) is achieved within the 5 minute contact time: | 20 ppm PFA-R = >5.15 | 20 ppm PFA-R = 3.46 | 20 ppm PFA-R = >5.22 |
| | 30 ppm PFA-R = >5.15 | 30 ppm PFA-R = 4.92 | 30 ppm PFA-R = >5.22 |
| | 50 ppm PFA-R = >5.15 | 50 ppm PFA-R = >5.10 | 50 ppm PFA-R = >5.22 |
| | 25 ppm POAA-R = 2.05 | 25 ppm POAA-R = <1.74 | 25 ppm POAA-R = >5.22 |

TABLE 35-continued

| Passing Requirements & Results | | | |
|---|---|---|---|
| Passing Requirements per EN 1276: | S. aureus | E. hirae | P. aeruginosa |
| | 38 ppm POAA-R = >5.15 | 38 ppm POAA-R = 3.29 | 38 ppm POAA-R = >5.22 |
| | 62 ppm POAA-R = >5.15 | 62 ppm POAA-R = >5.10 | 62 ppm POAA-R = >5.22 |

Figure 20:
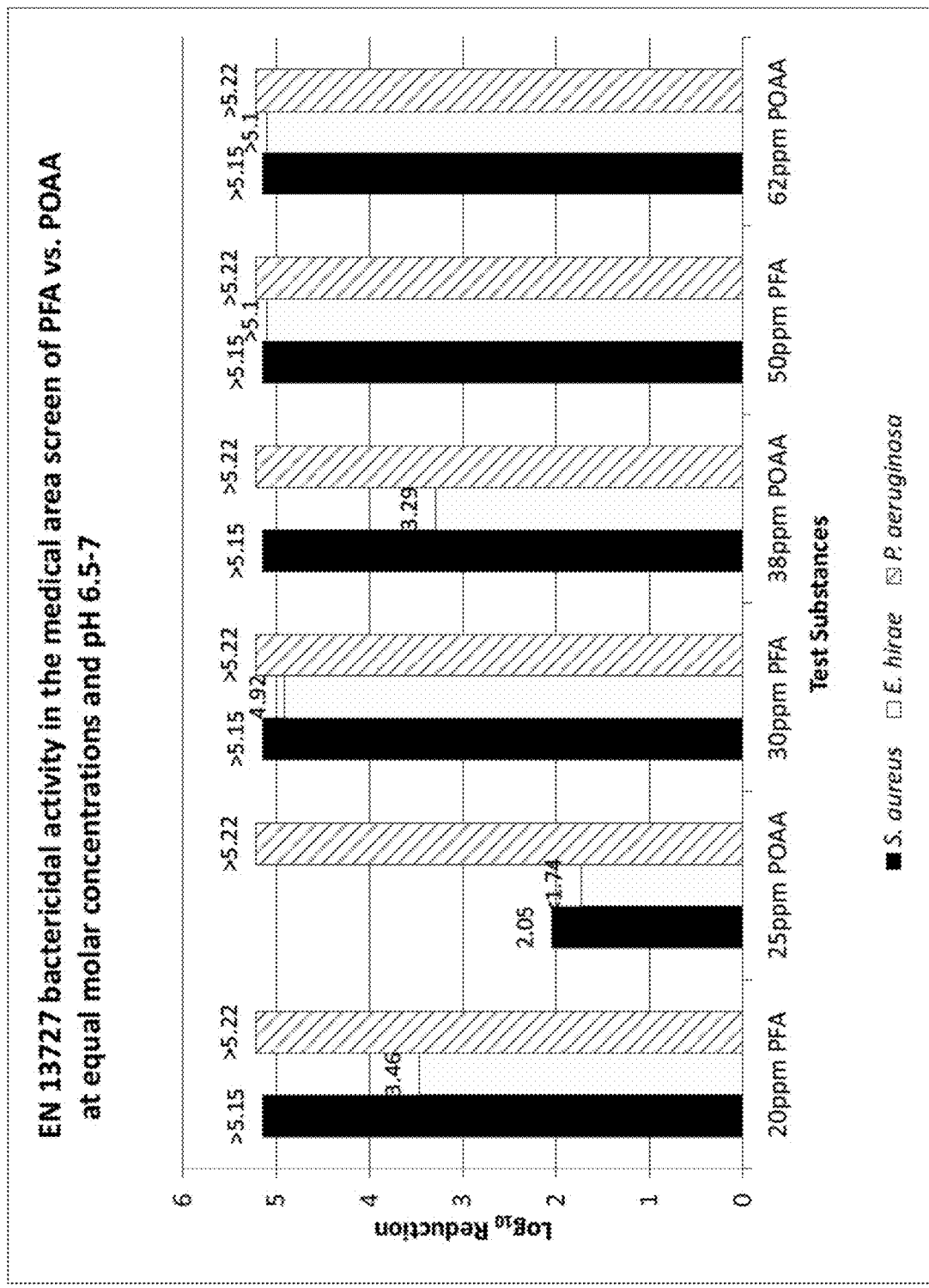
FIG. 20 illustrates micro efficacy of peroxyformic acid compositions in comparison to peroxyacetic acid according to embodiments of the invention.

As shown in FIG. 20 the PFA compositions generated according to the methods of the invention provided at least substantially similar or improved reduction in bactericidal activity against various pathogens, including medical pathogens and those related to skin disinfection.

Example 25. Summary of Fungicidal and Sporicidal Activity of Ester PFA

Various pathogens were used to evaluate the broad micro efficacy spectrum of ester PFA generated according to methods of the present invention. The test method, substance and results are shown in Table 36.

TABLE 36

Micro Efficacy Test Parameters and Results

| Test Method | Test Substance | Test Organisms | Passing Requirement | Result |
|---|---|---|---|---|
| EN 13727 | 450 ppm PFA pH 6-7 | P. aeruginosa ATCC 15442 | 5 log reduction | PASS |
| | | Staph. Aureus ATCC 6538 | | PASS |
| | | Enterococcus hirae ATCC 10541 | | PASS |
| EN 13624 | | Canidia albicans ATCC 10231 | 4 log reduction | PASS |
| | | Aspergillus brasiliensis ATCC 1604 | | PASS |
| EN 13704 | | Bacillus subtilis ATCC 6633 | 3 log reduction | PASS |
| EN 14476 | | Poliovirus | 4 log reduction | PASS |

Example 26. Hard Surface Testing with POAA and PFA from Ester Formate

Various pathogens were used to evaluate the broad micro efficacy spectrum of ester PFA generated according to methods of use for hard surface disinfection. The test method, substance and results are shown in Table 37.

Example 27. Laundry Bleaching Efficacy of PFA

TABLE 37

Micro Efficacy Test Parameters and Results

| | Test Substance | Exposure Time |
|---|---|---|
| Test Results | 850 ppm POAA + 1% Ester pH 4.44 | 3 minutes |

TABLE 37-continued

Micro Efficacy Test Parameters and Results

| | Test System | Plate Count | | |
|---|---|---|---|---|
| Culture Counts | P. aeruginosa | 27 | | |
| | | 31 | | |
| | S. aureus | 60 | | |
| | | 69 | | |

| | Test System | Plate Count | Average CFU/mL | Average CFU/Carrier* |
|---|---|---|---|---|
| New Carrier Counts | P. aeruginosa | 48 | 4.53E+05 | 4.53E+06 |
| | | 42 | | |
| | | 46 | | |
| | S. aureus | 55 | 4.87E+05 | 4.87E+06 |
| | | 35 | | |
| | | 56 | | |

Figure 21:
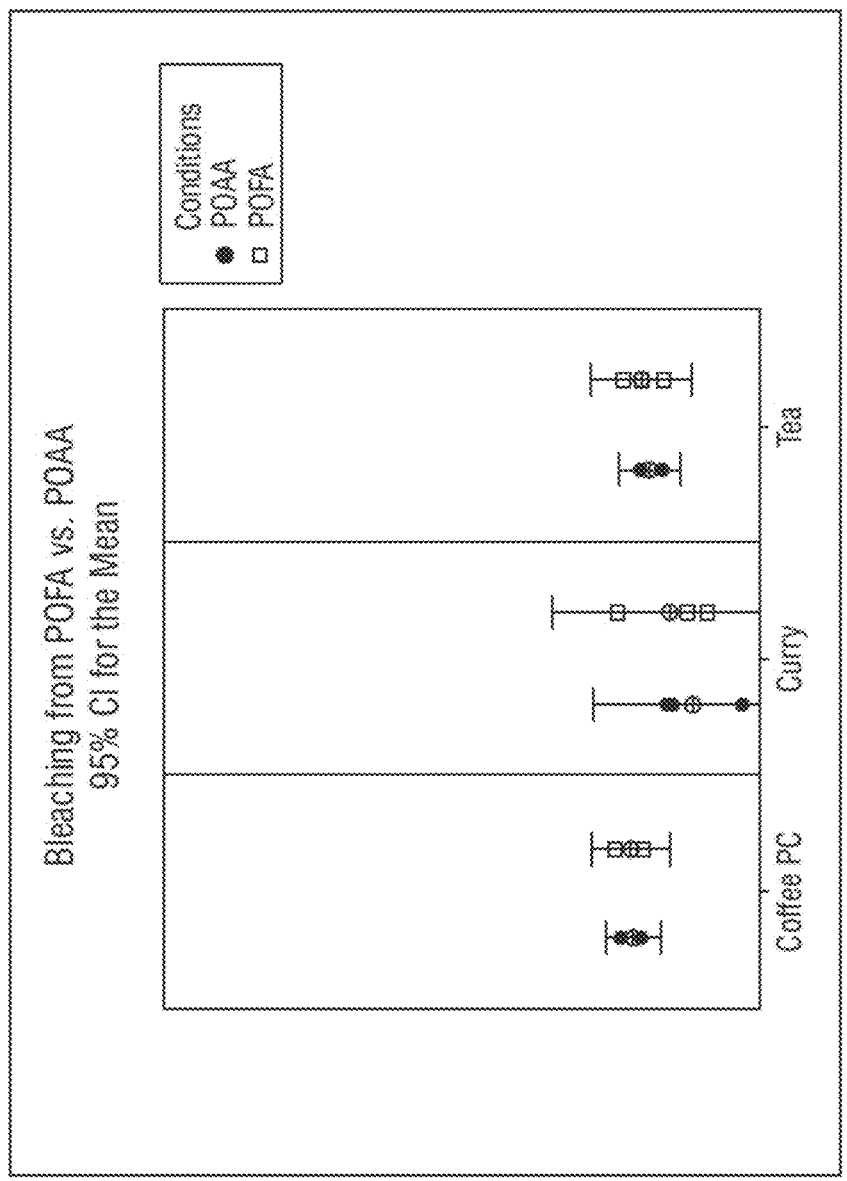
FIG. 21 illustrates the bleaching efficacy of performic acid generated according to embodiments of the invention.

Laundry bleach testing to compare performance of performic acid and peracetic acid was performed with three different stains (coffee, curry and tea known to require bleaching actives for removal) on polyester fibers at 40° C. for 10 minutes. A 15% peroxyacetic acid was compared at 3 oz/cwt laundry dosing) to a peroxyformic acid on a equi-molar basis. In comparison, the performance of peracetic acid was also tested under the same conditions with equal molar concentration. The result are shown in FIG. 21 comparing the percent of stain removal (bleaching efficacy) on the various stains. Beneficially, the peroxyformic acid is as efficient as peracetic acid as laundry bleach agent under the same conditions.

Example 27. Laundry Disinfection Efficacy of PFA

The microbial efficacy of peroxyformic acid was also tested following the EPA protocol on 100% cotton carriers against a water control. The test conditions were pH 7.7, 500 ppm hard water, 40° C. and 5 minute exposure time. In comparison, the performance of peracetic acid was also tested under the same conditions. The results are summarized in Table 38.

TABLE 38

| | | Staphylococcus aureus ATCC 6538 | | Klebsiella pneumoniae ATCC 4352 | |
|---|---|---|---|---|---|
| Test microorganism | | | Log | | Log |
| Test substance | Conc. (ppm) | Log survivors (CFU/carrier) | reduction | Log survivors (CFU/carrier) | reduction |
| Water control | | 6.85 | n/a | 6.12 | n/a |
| Peracetic acid | 42 | <1.00 | >5.85 | 3.66 | 2.46 |
| Performic acid | 18 | 1.63 | 5.22 | <1.00 | >5.12 |

As shown, despite peroxyformic acid being less than half of the dose of peracetic acid, it delivers significant better kill than peracetic acid.

Example 28. Stability of PFA in Use Solution in the Presence of Soils

Figure 22:
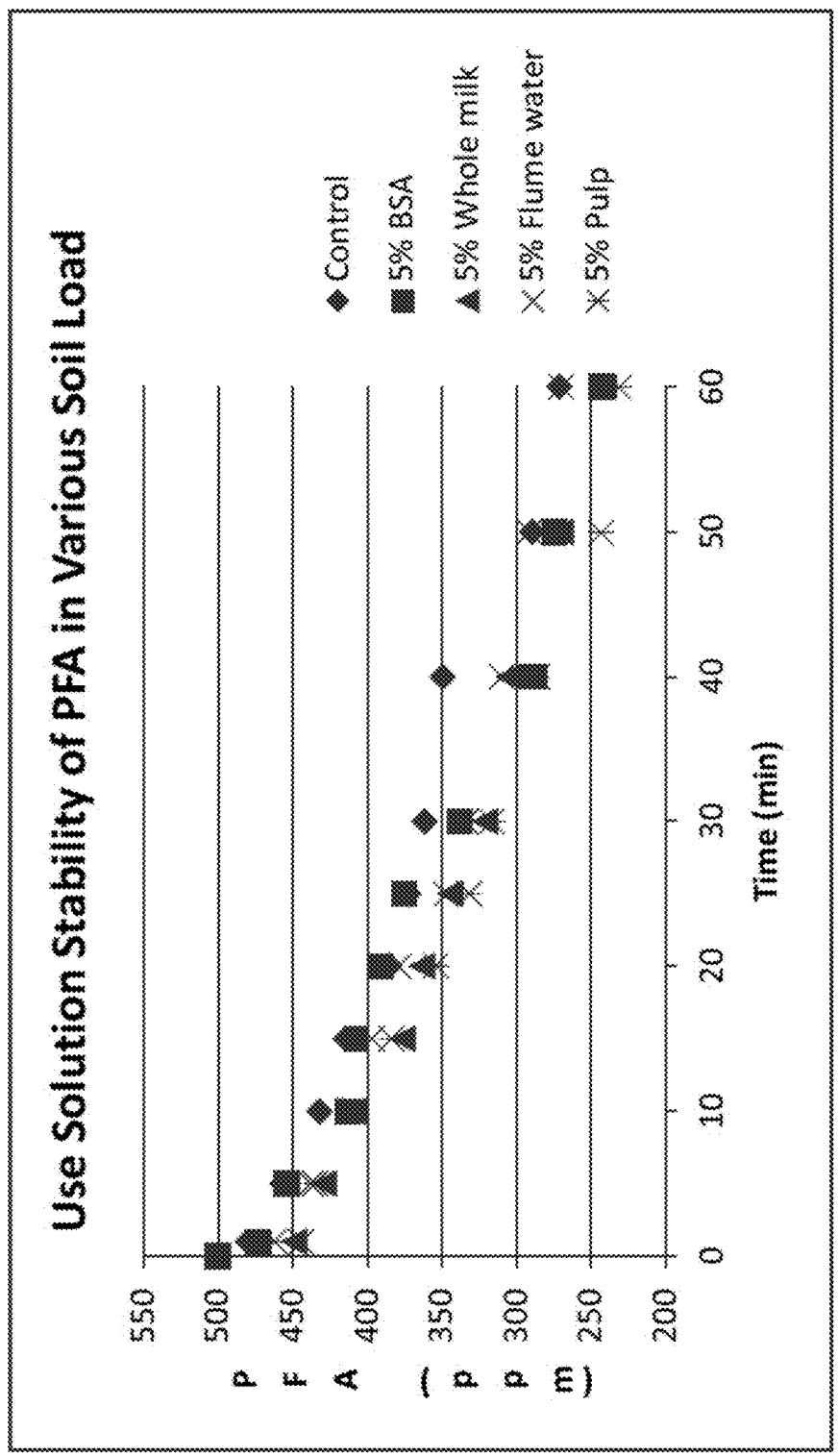
FIG. 22 illustrates the stability of peroxyformic acid in high soil loads according to embodiments of the invention.

To 200 g of 500 ppm hard water containing individual soil load at the desired concentration, was added PFA stock solution to target PFA concentration of 500 ppm. The resulting solution was stored under ambient conditions, and the level of PFA was monitored by iodometric titration at the specific time point. The results are shown in FIG. 22 demonstrating that despite the unstable nature of performic acid (shown by decrease in PFA concentration of the control), the soils tested had no impact on the stability of PFA.

Example 29. Optimizing the Ratio of Glycerol Formate and an Acid Peroxide Premix for Performic Acid Generation An ester of a polyhydric alcohol and formic acid (glycerol formate), hydrogen peroxide and an acid catalyst were combined without any additional water (outside of RM) added. Glycerol formate was preweighed into a sample container. Acid premix (peroxide, sulfuric acid, and deionized water) were preweighed into a second sample container. The second sample container was poured into the first sample container and started timer followed by a brief period (<30 seconds of gentle mixing). At the time points noted in the data tables below, titrated mixture to quantitate performic acid and hydrogen peroxide content.

TABLE 39

Ratios evaluated

| Sample | % by wt Glycerol Formate | % by wt Acid Premix |
|---|---|---|
| 1-1 | 64% | 36% |
| 1-2 | 60% | 40% |
| 1-3 | 56% | 44% |
| 1-4 | 45% | 55% |
| 1-5 | 35% | 65% |

TABLE 40

Acid Premix Composition

| Raw Material | % by wt | % active |
|---|---|---|
| Peroxide (50%) | 31.11 | 15.56 |
| H2SO4 (50%) | 66.67 | 33.34 |
| DI Water | 2.22 | 2.22 |

TABLE 41

Titration Results

| Sample | Time (min) | % PFA | H2O2% |
|---|---|---|---|
| 1-1 | 5 | 5.87% | 2.17% |
| 1-1 | 10 | 5.83% | 2.18% |
| 1-1 | 20 | 5.80% | 2.17% |
| 1-1 | 122 | 5.67% | 2.13% |
| 1-2 | 5 | 6.10% | 2.71% |
| 1-2 | 10 | 6.21% | 2.65% |
| 1-2 | 20 | 6.15% | 2.70% |
| 1-2 | 60 | 6.08% | 2.65% |
| 1-3 | 5 | 6.16% | 3.23% |
| 1-3 | 10 | 6.33% | 3.20% |
| 1-3 | 20 | 6.43% | 3.21% |
| 1-4 | 1 | 2.57% | 6.40% |
| 1-4 | 3 | 5.51% | 5.11% |
| 1-4 | 5 | 5.83% | 4.89% |
| 1-4 | 10 | 6.00% | 5.12% |
| 1-4 | 23 | 5.87% | 0.00% |
| 1-5 | 3 | 5.57% | 6.51% |
| 1-5 | 5.5 | 6.16% | 6.19% |
| 1-5 | 10 | 6.12% | 6.15% |
| 1-5 | 20 | 6.14% | 6.19% |
| 1-5 | 90 | 5.91% | 6.15% |

Figure 23:
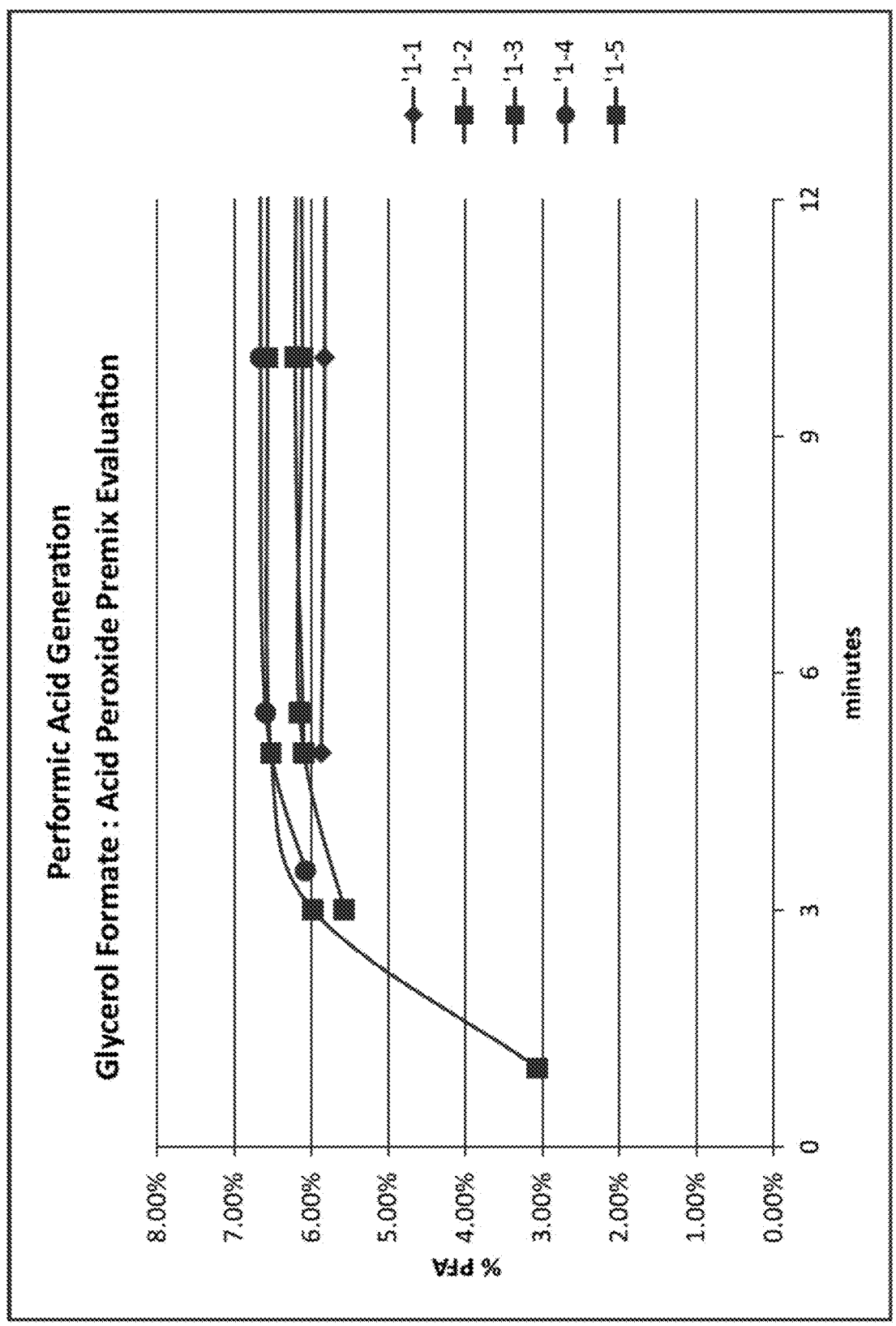
FIG. 23 shows the generation of peroxyformic acid using a concentrate glycerol formate and acid peroxide premix according to embodiments of the invention.
Figure 24:
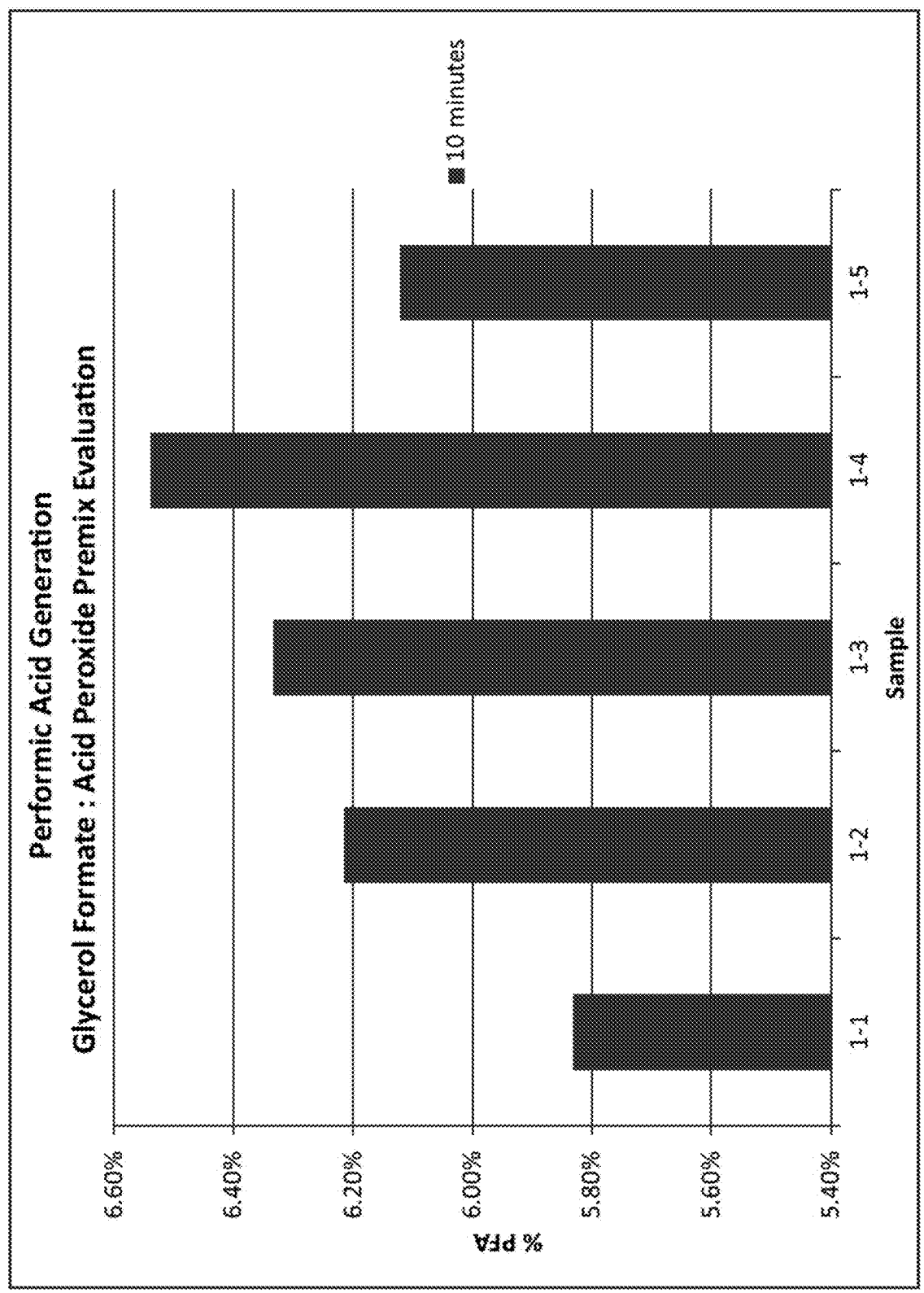
FIG. 24 shows the impact of the ratio of the glycerol formate and acid peroxide premix for maximizing peroxyformic acid yield according to embodiments of the invention.

Results are further shown in FIG. 23 depicting the peroxyformic acid generation using the glycerol formate and acid peroxide premix showing generated peak performic acid content achieved by 5 minutes. As depicted from about 5.5% to about 7% peroxyformic acid was generated in the 5 minutes. The optimal ratio of the glycerol formate and acid peroxide premix for maximizing peroxyformic acid yield is further depicted in FIG. 24.

Example 30. Optimizing the Composition of the Acid Peroxide Premix for Performic Acid Generation The methods of Example 29 were followed using the formulations shown in the following tables to combine different ratios of an ester of a polyhydric alcohol and formic acid (glycerol formate), hydrogen peroxide and an acid catalyst.

TABLE 42

Ratios Evaluated

| Material | Sample 2-1 | Sample 2-2 | Sample 2-3 | Sample 2-4 |
|---|---|---|---|---|
| Glycerol Formate | 64.00 | 64.00 | 64.00 | 64.00 |
| Acid Peroxide Premix A | 36.00 | 0.00 | 0.00 | 0.00 |
| Acid Peroxide Premix B | 0.00 | 36.00 | 0.00 | 0.00 |
| Acid Peroxide Premix C | 0.00 | 0.00 | 36.00 | 0.00 |
| Acid Peroxide Premix D | 0.00 | 0.00 | 0.00 | 36.00 |

TABLE 43

Acid Premix Composition

| Material | wt % of H2O2 premix A | wt % of H2O2 premix B | wt % of premix C | wt % of premix D |
|---|---|---|---|---|
| Peroxide (50%) | 31.11 | 62.00 | 31.11 | 62.00 |
| H2SO4 (50%) | 66.67 | 33.45 | 16.67 | 16.67 |
| DI | 2.22 | 4.55 | 52.22 | 21.33 |

TABLE 44

| Compositions (Active %) | | | | |
|---|---|---|---|---|
| | Sample | | | |
| | 2-1 | 2-2 | 2-3 | 2-4 |
| Glycerol Formate | 64.00 | 64.00 | 64.00 | 64.00 |
| Peroxide | 5.60 | 11.16 | 5.60 | 11.16 |
| H2S04 | 12.00 | 6.02 | 3.00 | 3.00 |
| DI | 18.40 | 18.82 | 27.40 | 21.84 |

TABLE 45

Titration Results

| Premix | Time (min) | % PFA |
|---|---|---|
| 2-2 | 1 | 1.25% |
| 2-2 | 3 | 3.94% |
| 2-2 | 5 | 7.14% |
| 2-2 | 10 | 9.00% |
| 2-2 | 30 | 9.68% |
| 2-2 | 60 | 9.69% |
| 2-2 | 120 | 9.50% |
| 2-2 | 180 | 9.41% |
| 2-2 | 240 | 9.08% |
| 2-2 | 5760 | 3.88% |
| 2-2 | 10080 | 2.03% |
| 2-3 | 1 | 0.23% |
| 2-3 | 4.5 | 0.41% |
| 2-3 | 10 | 1.02% |
| 2-3 | 40 | 3.64% |
| 2-3 | 50 | 3.79% |
| 2-3 | 60 | 3.73% |
| 2-3 | 5760 | 1.61% |
| 2-3 | 10080 | 0.87% |
| 2-4 | 1 | 0.21% |
| 2-4 | 3 | 0.94% |
| 2-4 | 6 | 1.89% |
| 2-4 | 8 | 3.37% |
| 2-4 | 10.5 | 3.75% |
| 2-4 | 15 | 5.40% |
| 2-4 | 20 | 6.73% |
| 2-4 | 30 | 7.89% |
| 2-4 | 64 | 8.05% |
| 2-1 | 5 | 5.87% |
| 2-1 | 10 | 5.83% |
| 2-1 | 20 | 5.80% |
| 2-1 | 122 | 5.67% |

Figure 25:
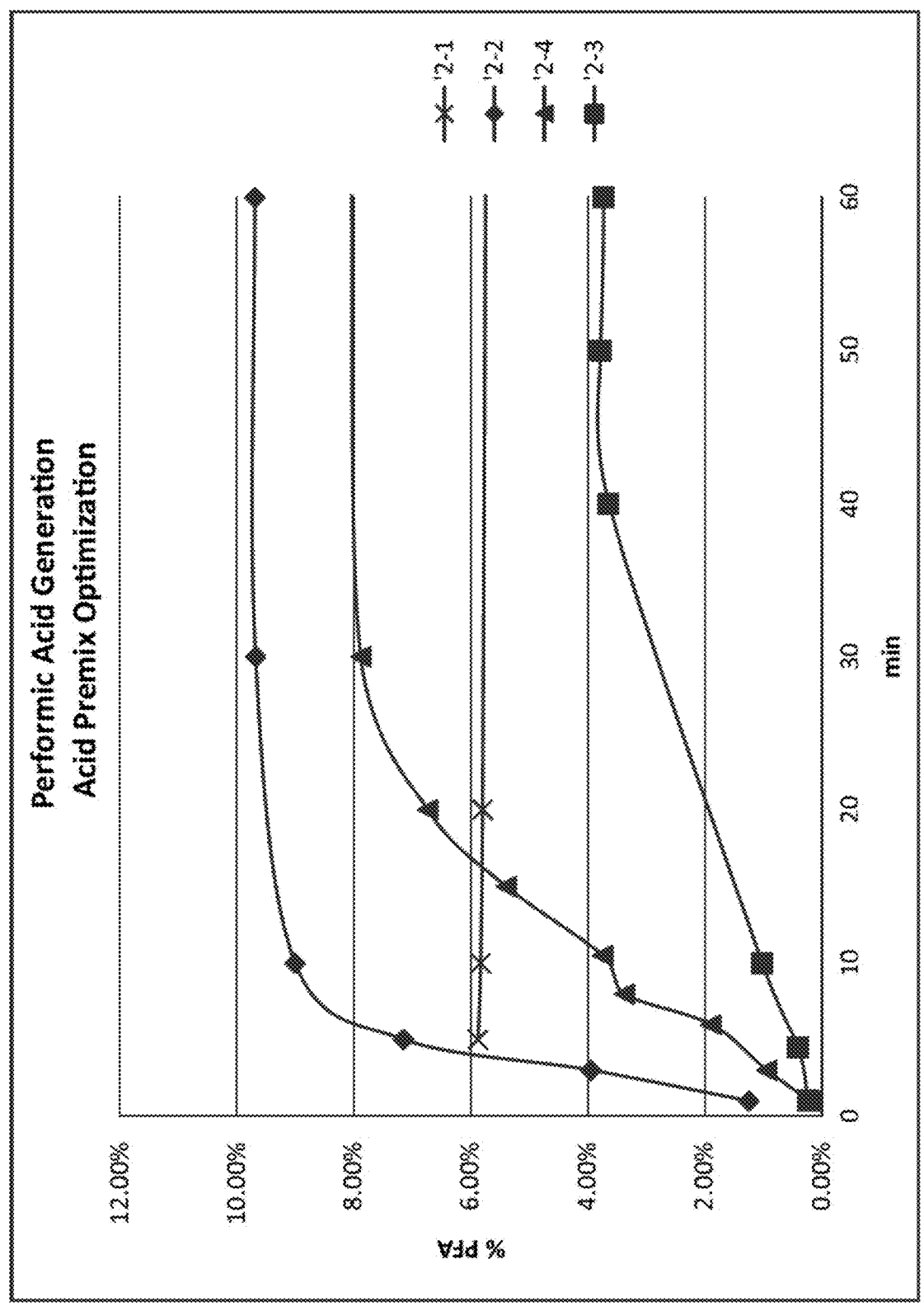
FIG. 25 shows the peroxyformic acid generation with the acid premix concentrate according to embodiments of the invention.

Results are further shown in FIG. 25 depicting the peroxyformic acid generation with the acid premix optimization, demonstrating sample 2-2 provides the highest yield of peroxyformic acid within 10 minutes. The results of this Example yielded a higher percentage (about 10%) peroxyformic acid at a slower reaction than that of Example 29. The results illustrate the impact of the acid catalyst and pH of the formulations impact on the yield of peroxyformic acid.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

The claimed invention is:

1. A method for forming peroxyformic acid comprising:
  contacting a first reagent that comprises an ester of a polyhydric alcohol and formic acid, and a second reagent that comprises hydrogen peroxide or a substance that generates hydrogen peroxide to form peroxyformic acid,
  wherein the formed peroxyformic acid comprises at least about 1 ppm peroxyformic acid within about 1 minute, and
  wherein the pH of said formed peroxyformic acid becomes about 8 or lower within about 1 minute after the contact between said first reagent and said second reagent and
  wherein the method for forming peroxyformic acid does not include an enzyme catalyst.

2. The method of claim 1, wherein the ester of a polyhydric alcohol and formic acid comprises glycerol formates, ethylene glycol formates, pentaerythritol formates, mannitol formates, propylene glycol formates, sorbitol formates and sugar formates, and wherein the sugar formates are sucrose formates, dextrin formates, maltodextrin formates, or starch formates.

3. The method of claim 1, wherein the first reagent and the second reagent are contacted with each other to form a solution of peroxyformic acid that has a pH ranging from about 2 to about 8.

4. The method of claim 1, wherein said first reagent and said second reagent are kept separately prior to said contacting.

5. The method of claim 1, wherein the first reagent and the second reagent are contacted to form a solution of peroxyformic acid that comprises at least about 1 ppm peroxyformic acid within about 30 seconds or less.

6. The method of claim 1, wherein the first reagent and the second reagent are contacted to form a solution of peroxyformic acid that comprises at least about 1 ppm peroxyformic acid within about 15 seconds or less.

7. The method of claim 1, wherein the first reagent and the second reagent are contacted to form a solution of peroxyformic acid that comprises at least about 100 ppm peroxyformic acid within about 5 minutes or less.

8. The method of claim 1, wherein the first reagent and the second reagent are contacted to form a solution of peroxyformic acid that comprises at least about 500 ppm peroxyformic acid within about 5 minutes or less.

9. The method of claim 1, wherein the first reagent and the second reagent are contacted to form a solution of peroxyformic acid that comprises peroxyformic acid under temperatures from about 0° C. to about 60° C.

10. The method of claim 1, which further comprises using a stabilizing agent for peroxyformic acid, a stabilizing agent for hydrogen peroxide, and/or a pH buffering agent.

11. The method of claim 10, wherein (i) the first reagent comprises the stabilizing agent for peroxyformic acid and/or a pH buffering agent, (ii) the second reagent comprises the stabilizing agent for hydrogen peroxide, and/or (iii) a third reagent comprises the stabilizing agent for peroxyformic acid, the stabilizing agent for hydrogen peroxide, and/or a pH buffering agent.

12. The method of claim 1, which is used to form a solution that comprises from about 0.1 ppm to about 100,000 ppm of peroxyformic acid.

13. The method of claim 1, which is used to form a solution that comprises from about 100 ppm to about 1,000 ppm of peroxyformic acid.

14. The method of claim 1, which further comprises forming a C2-C22 percarboxylic acid in the liquid comprising peroxyformic acid.

15. The method of claim 14, wherein the second reagent is an equilibrium C2-C22 percarboxylic acid composition providing the hydrogen peroxide.

16. A method for forming peroxyformic acid comprising:
contacting a first reagent that comprises an ester of a polyhydric alcohol and formic acid, and a second reagent that comprises hydrogen peroxide or that comprises a substance that generates hydrogen peroxide when in contact with a liquid, to form a liquid that comprises from about 0.1 ppm to about 100,000 ppm of peroxyformic acid and wherein the pH of said formed liquid becomes about 8 or lower within about 1 minute after the contact between said first reagent and said second reagent; and
wherein the first reagent and the second reagent are contacted to form a solution that comprises at least about 1 ppm peroxyformic acid within about 1 minute of the contact time; and
wherein the method for forming peroxyformic acid does not include an enzyme catalyst.

17. The method of claim 16, wherein the first reagent and the second reagent are kept separately prior to said contacting.

18. The method of claim 16, wherein the first reagent and the second reagent are contacted with each other to form a solution that has a pH ranging from about 4 to about 8.

19. The method of claim 16, wherein the first reagent and the second reagent are contacted to form a solution that comprises at least about 1 ppm peroxyformic acid within about 30 seconds or less.

20. The method of claim 16, wherein the first reagent and the second reagent are contacted to form a solution that comprises at least about 1 ppm peroxyformic acid within about 15 seconds or less.

* * * * *

UNITED STATES PATENT AND TRADEMARK OFFICE
CERTIFICATE OF CORRECTION

PATENT NO. : 10,542,751 B2
APPLICATION NO. : 15/967077
DATED : January 28, 2020
INVENTOR(S) : Li et al.

It is certified that error appears in the above-identified patent and that said Letters Patent is hereby corrected as shown below:

On the Title Page

Item (56), OTHER PUBLICATIONS, Column 2, Line 1:
DELETE: "Hyrolase"
INSERT: --Hydrolase--

Signed and Sealed this
Twenty-fourth Day of March, 2020

Andrei Iancu
*Director of the United States Patent and Trademark Office*